(12) United States Patent
Miller et al.

(10) Patent No.: US 7,399,959 B2
(45) Date of Patent: Jul. 15, 2008

(54) METHOD AND APPARATUS FOR ENHANCED ION BASED SAMPLE FILTERING AND DETECTION

(75) Inventors: Raanan A. Miller, Bedford, MA (US); Erkinjon G. Nazarov, Lexington, MA (US); C. James Morris, Norfolk, MA (US); Stephen Coy, Wayland, MA (US); Edward Bullister, Weston, MA (US)

(73) Assignee: Sionex Corporation, Bedford, MA (US)

( * ) Notice: Subject to any disclaimer, the term of this patent is extended or adjusted under 35 U.S.C. 154(b) by 403 days.

(21) Appl. No.: 11/293,651

(22) Filed: Dec. 2, 2005

(65) Prior Publication Data

US 2006/0222562 A1    Oct. 5, 2006

Related U.S. Application Data

(60) Provisional application No. 60/632,896, filed on Dec. 3, 2004.

(51) Int. Cl.
  *B01D 59/44* (2006.01)
  *H01J 49/00* (2006.01)
(52) U.S. Cl. .................. 250/287; 250/281; 250/282; 250/286; 250/288; 250/290; 250/292; 250/293; 250/294; 422/50; 422/83
(58) Field of Classification Search ................ 250/281, 250/282, 286, 287, 288, 290, 292, 293, 294; 422/50, 83
See application file for complete search history.

(56) References Cited

U.S. PATENT DOCUMENTS

| | | | |
|---|---|---|---|
| 2,615,135 A | 10/1952 | Glenn | |
| 2,818,507 A | 12/1957 | Britten | |
| 2,919,348 A | 12/1959 | Bierman | |
| 3,511,986 A | 5/1970 | Llewellyn | |
| 3,619,605 A | 11/1971 | Cook et al. | |
| 3,621,240 A | 11/1971 | Cohen et al. | |
| 3,931,589 A | 1/1976 | Aisenberg et al. | |
| 4,019,989 A | 4/1977 | Hazewindus et al. | |
| 4,025,818 A | 5/1977 | Giguere et al. | |
| 4,136,280 A | 1/1979 | Hunt et al. | |
| 4,163,151 A | 7/1979 | Bayless et al. | |
| 4,201,921 A | 5/1980 | McCorkle | |

(Continued)

FOREIGN PATENT DOCUMENTS

RU    1412447 A1    6/1998

(Continued)

OTHER PUBLICATIONS

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

(Continued)

*Primary Examiner*—Jack I. Berman
*Assistant Examiner*—Meenakshi S Sahu
(74) *Attorney, Agent, or Firm*—Ropes & Gray LLP

(57) ABSTRACT

The invention provides, in various embodiments, systems and methods relating to enhancing the filtering and detection capability of ion mobility based systems by various techniques to counteract a charge buildup in the ion mobility based system.

30 Claims, 36 Drawing Sheets

U.S. PATENT DOCUMENTS

| | | | |
|---|---|---|---|
| 4,315,153 | A | 2/1982 | Vahrenkamp |
| 4,517,462 | A | 5/1985 | Boyer et al. |
| 4,761,545 | A | 8/1988 | Marshall et al. |
| 5,144,127 | A | 9/1992 | Williams et al. |
| 5,218,203 | A | 6/1993 | Eisele et al. |
| 5,298,745 | A | 3/1994 | Kernan et al. |
| 5,420,424 | A | 5/1995 | Carnahan et al. |
| 5,455,417 | A | 10/1995 | Sacristan |
| 5,492,867 | A | 2/1996 | Kotvas et al. |
| 5,536,939 | A | 7/1996 | Freidhoff et al. |
| 5,541,408 | A | 7/1996 | Sittler |
| 5,654,544 | A | 8/1997 | Dresch |
| 5,723,861 | A | 3/1998 | Carnahan et al. |
| 5,763,876 | A | 6/1998 | Perinarides et al. |
| 5,789,745 | A | 8/1998 | Martin et al. |
| 5,801,379 | A | 9/1998 | Kouznetsov |
| 5,811,059 | A | 9/1998 | Genovese et al. |
| 5,834,771 | A | 11/1998 | Yoon et al. |
| 5,838,003 | A | 11/1998 | Bertsch et al. |
| 5,965,882 | A | 10/1999 | Megerle et al. |
| 5,998,788 | A | 12/1999 | Breit |
| 6,051,832 | A | 4/2000 | Bradshaw |
| 6,055,151 | A | 4/2000 | Tormey et al. |
| 6,066,848 | A | 5/2000 | Kassel et al. |
| 6,107,624 | A | 8/2000 | Doring et al. |
| 6,107,628 | A | 8/2000 | Smith et al. |
| 6,124,592 | A | 9/2000 | Spangler |
| 6,200,539 | B1 | 3/2001 | Sherman et al. |
| 6,323,482 | B1 | 11/2001 | Clemmer et al. |
| 6,479,815 | B1 | 11/2002 | Goebel et al. |
| 6,495,823 | B1 | 12/2002 | Miller et al. |
| 6,504,149 | B2 | 1/2003 | Guevremont et al. |
| 6,512,224 | B1 | 1/2003 | Miller et al. |
| 6,621,077 | B1 | 9/2003 | Guevremont et al. |
| 6,639,212 | B1 | 10/2003 | Guevremont |
| 6,653,627 | B2 | 11/2003 | Guevremont |
| 6,690,004 | B2 | 2/2004 | Miller |
| 6,703,609 | B2 | 3/2004 | Guevremont |
| 6,713,758 | B2 | 3/2004 | Guevremont |
| 6,753,522 | B2 | 6/2004 | Guevremont |
| 6,770,875 | B1 | 8/2004 | Guevremont |
| 6,774,360 | B2 | 8/2004 | Guevremont |
| 6,787,765 | B2 | 9/2004 | Guevremont |
| 6,799,355 | B2 | 10/2004 | Guevremont |
| 6,806,466 | B2 | 10/2004 | Guevremont |
| 6,998,608 | B2 | 2/2006 | Guevremont et al. |
| 7,122,794 | B1 * | 10/2006 | Miller et al. ............. 250/294 |
| 2001/0030285 | A1 | 10/2001 | Miller et al. |
| 2002/0070338 | A1 | 6/2002 | Lododa |
| 2002/0134932 | A1 | 9/2002 | Guevremont et al. |
| 2003/0020012 | A1 | 1/2003 | Guevremont |
| 2003/0038235 | A1 | 2/2003 | Guevremont et al. |
| 2003/0052263 | A1 | 3/2003 | Kaufman et al. |
| 2003/0070913 | A1 | 4/2003 | Miller et al. |
| 2003/0089847 | A1 | 5/2003 | Guevremont et al. |
| 2003/0132380 | A1 | 7/2003 | Miller et al. |
| 2004/0094704 | A1 | 5/2004 | Miller et al. |

FOREIGN PATENT DOCUMENTS

| | | |
|---|---|---|
| RU | 1485808 A1 | 6/1998 |
| SU | 966583 | 10/1982 |
| SU | 1337934 A2 | 9/1987 |
| SU | 1627984 A2 | 2/1991 |
| WO | WO-96/19822 A1 | 6/1996 |
| WO | WO-00/08454 | 2/2000 |
| WO | WO-00/08455 | 2/2000 |
| WO | WO-00/08456 | 2/2000 |
| WO | WO-00/08457 | 2/2000 |
| WO | WO-01/08197 A1 | 2/2000 |
| WO | WO-01/22049 A2 | 3/2001 |
| WO | WO-01/35441 A1 | 5/2001 |
| WO | WO-01/69217 A2 | 9/2001 |
| WO | WO-01/69220 A2 | 9/2001 |
| WO | WO-01/69647 A2 | 9/2001 |
| WO | WO-02/071053 A2 | 9/2002 |
| WO | WO-03/005016 A1 | 1/2003 |
| WO | WO-2004/097396 A1 | 11/2004 |

OTHER PUBLICATIONS

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05, Nov. 26, 1999.

Barnett et al., "Isotope Separation Using High-Field Asymmetric Waveform Ion Mobility Spectrometry," Nuclear Instruments & Methods in Physics Research, vol. 450, No. 1, pp. 179-185 (2000).

Buryakov et al., "A New Method of Separation of Multi-Atomic Ions by Mobility at Atmospheric Pressure Using a High-Frequency Amplitude-Asymmetric Strong Electric Field," International Journal of Mass Spectrometry and Ion Processes, vol. 128 pp. 1433-148 (1993).

Buryakov et al., "Drift Spectrometer for the Control of Amine Traces in the Atmosphere," J. Anal. Chem., vol. 48, No. 1, pp. 112-121 (1993).

Buryakov et al., "Separation of Ions According to Mobility in a Strong AC Electric Field," Letters to Journal of Technical Physics, vol. 17, pp. 11-12 (1991).

Buryakov et al., "Device and Method of Gas Electrophoresis, Chemical Analysis of Environment," ed. Prof. V.V. Malakhov, Novosibirsk: Nauka, pp. 113-127 (1991).

Carnahan et al., "Field Ion Spectrometry—A New Analytical Technology for Trace Gas Analysis," ISA, vol. 51, No. 1, pp. 87-96 (1996).

Carnahan et al., "Field Ion Spectrometry—A New Technology for Cocaine and Heroin Detection," SPIE, vol. 2937, pp. 106-119 (1997).

Eiceman, et al., Miniature radio-frequency mobility analyzer as a gas chromatographic detector for oxygen-containing volatile organic compounds, pheromones and other insect attractants, Journal of Chromatography, vol. 917, pp. 205-217 (2001).

Guevremont et al., "Atmospheric Pressure Ion Focusing in a High-Field Asymmetric Waveform Ion Mobility Spectrometer," Review of Scientific Instruments, vol. 70, No. 2, pp. 1370-1383 (1999).

Guevremont et al., "Calculation of Ion Mobilities from Electrospray Ionization High-Field Asymmetric Waveform Ion Mobility Spectrometry Mass Spectrometry," Journal of Chemical Physics, vol. 144, No. 23, pp. 10270-10277 (2001).

Guevremont et al., "High Field Asymmetric Waveform Ion Mobility Spectrometry-Mass Spectrometry: An Investigation of Leucine Enkephalin Ions Produced by Electrospray Ionization," J. Am. soc. Mass. Spectrom., vol. 10, pp. 492-501 (1999).

Handy et al., "Determination of Nanomolar Levels of Perchlorate in Water by ESI-FAIMS-MS," J. Anal. At. Spectrometry, vol. 15, pp. 907-911 (2000).

Javahery et al., "A segmented radiofrequency-only quadrupole collision cell for measurements of Ion Collision cross section on a triple quadrupole mass spectrometer," J. Am. Soc. for Mass Spectrometry vol. 8, pp. 697-702, 1997.

Krylov, "A Method of Reducing Diffusion Losses in a Drift Spectrometer," Technical Physics, vol. 4d, No. 1, pp. 113-116 (1999).

Krylov, "Pulses of Special Shapes Formed on a Capacitice Load," Instruments and Experimental Techniques, vol. 40, No. 5, (1997). Also cited in Database Nauka/Interperiodika 'Online!, International Academic Publishing Company (IAPC), Russia, E. Krylov.

Miller et al., "A MEMS Radio-Frequency Ion Mobility Spectrometer for Chemical Agent Detection," Proceedings of the 2000 Solid State Sensors and Actuators Workshop (Hilton Head, SC, Jun. 2000).

Miller et al., "A MEMS radio-frequency ion mobility spectrometer for chemical vapor detection," Sensors and Actuators, vol. 91, pp. 301-312 (2001).

Miller et al., "A Novel Micromachined High-Field Asymmetric Waveform-Ion Mobility Spectrometer," Sensors and Actuators B, vol. B67, No. 3, pp. 300-306 (2000).

Pilzecker et al., "On-Site Investigations of Gas Insulated Substations Using Ion Mobility Spectrometry for Remote Sensing of SF6 Decomposition," IEEE, pp. 400-403 (2000).

Riegner et al., "Qualitative Evaluation of Field Ion Spectrometry for Chemical Warfare Agent Detection," Proceedings of the ASMS Conference on Mass Spectrometry and Allied Topics, pp. 473A-473B (1997).

Scheider et al., "High Sensitivity GC-FIS for Simultaneous Detection of Chemical Warfare Agents," Journal of Process Analytical Chemistry, vol. 5, Nos. 3, 4, pp. 124-136 (2000).

Verenchikov et al., "Analysis of Ionic Composition of Solutions Using An Ion Gas Analyzer Chemical Analysis of Environmental," edit. Prof. V.V. Malakhov Novosibirsk: Nauka pp. 127-134 (1991).

* cited by examiner

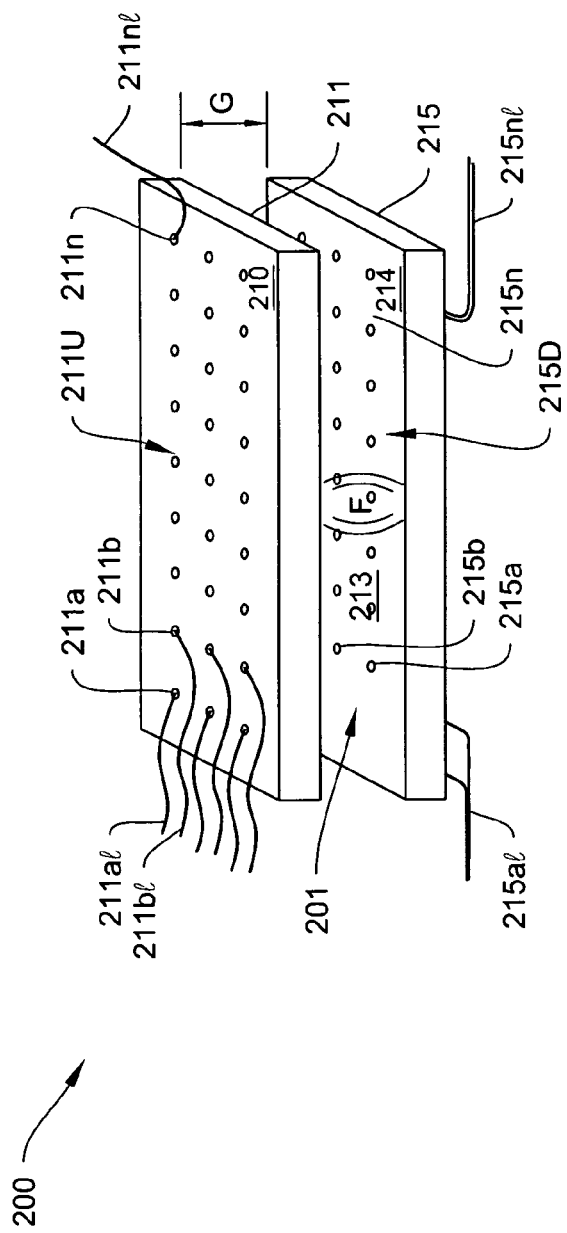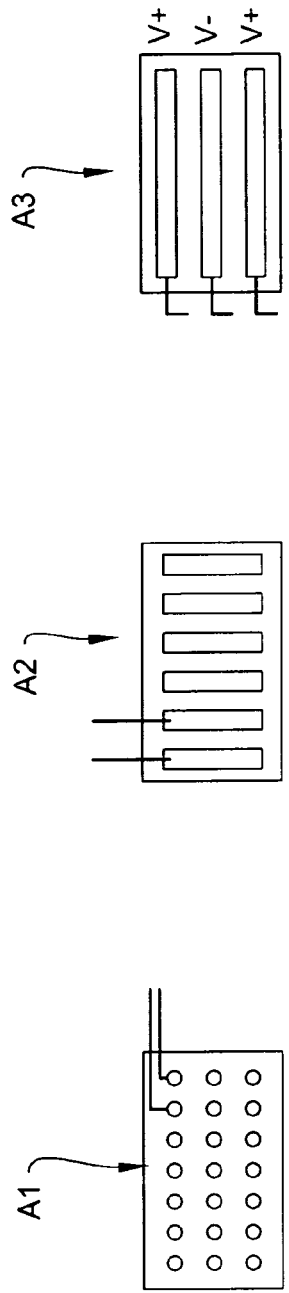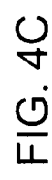
FIG. 4A
FIG. 4B
FIG. 4C
FIG. 4D

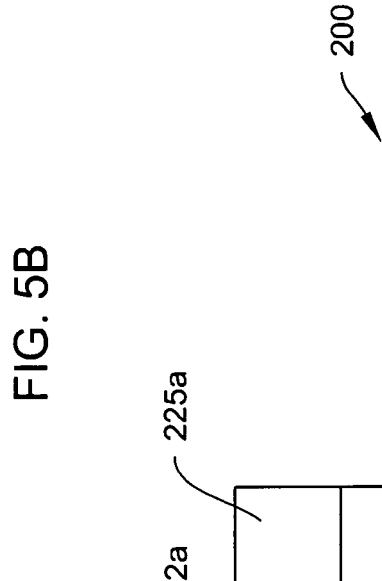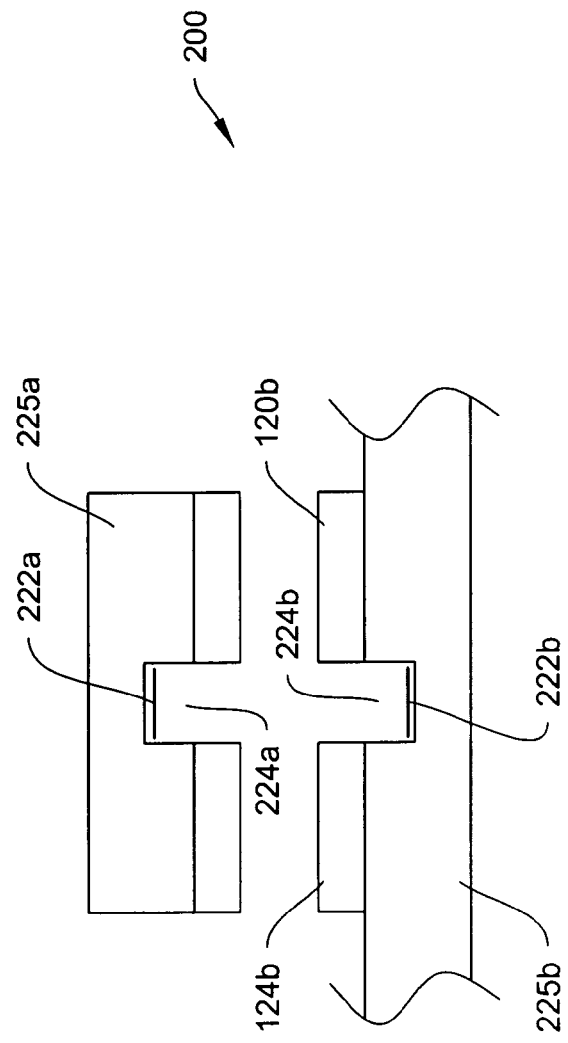

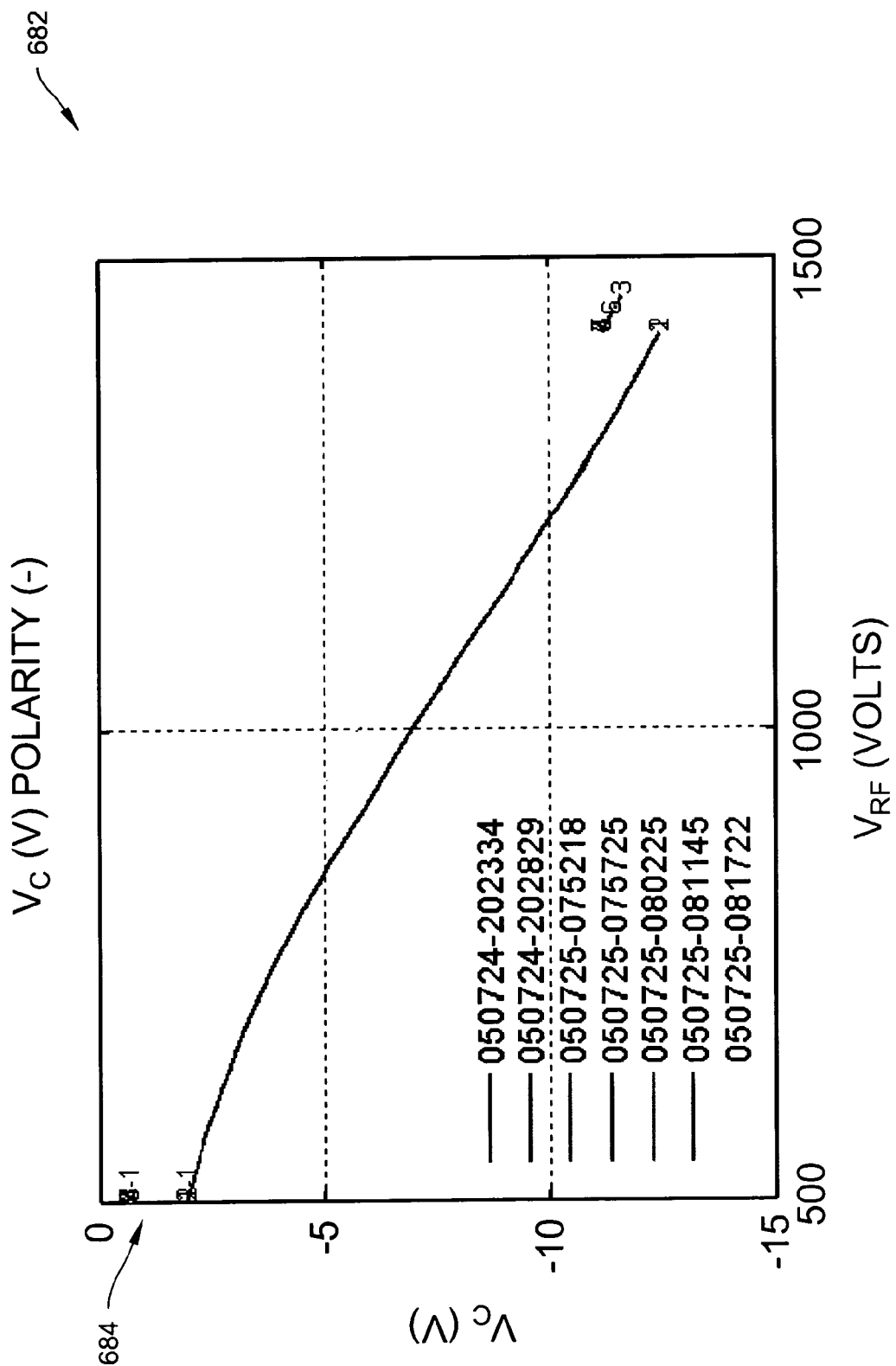

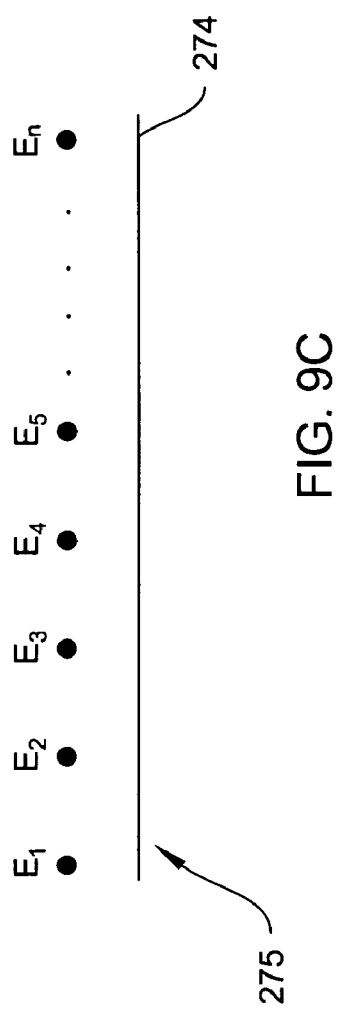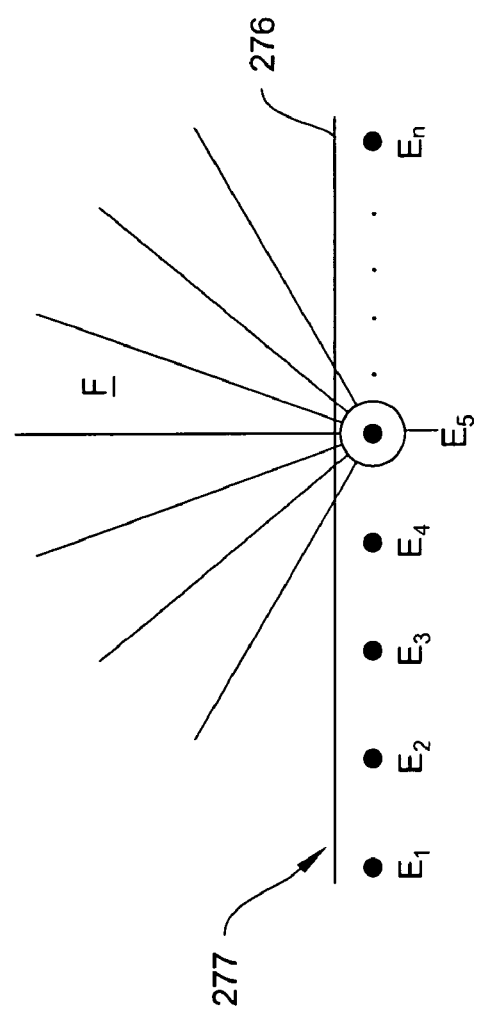

METHOD AND APPARATUS FOR ENHANCED ION BASED SAMPLE FILTERING AND DETECTION

REFERENCE TO RELATED APPLICATIONS

This application claims the benefit of and priority to U.S. Provisional Application No. 60/632,896, filed on Dec. 3, 2004, the entire teachings of which are incorporated herein by reference.

This application also incorporates by reference the entire contents of the following co-pending U.S. patent applications: U.S. Ser. No. 10/187,464, filed on 28 Jun. 2002; U.S. Ser. No. 10/215,251, filed on 7 Aug. 2002; U.S. Ser. No. 10/462,206, filed on 13 Jun. 2003; U.S. Ser. No. 10/684,332, filed on 10 Oct. 2003; U.S. Ser. No. 10/734,499, filed on 12 Dec. 2003; U.S. Ser. No. 10/738,967, filed on 17 Dec. 2003; U.S. Ser. No. 10/797,466, filed on 10 Mar. 2004; U.S. Ser. No. 10/821,812, filed on 8 Apr. 2004; U.S. Ser. No. 10/824,674, filed on 14 Apr. 2004; U.S. Ser. No. 10/836,432, filed on 30 Apr. 2004; U.S. Ser. No. 10/840,829, filed on 7 May 2004; U.S. Ser. No. 10/866,645, filed on 10 Jun. 2004; U.S. Ser. No. 10/887,016, filed on 8 Jul. 2004; U.S. Ser. No. 10/894,861, filed on 19 Jul. 2004; U.S. Ser. No. 10/903,497, filed on 30 Jul. 2004; U.S. Ser. No. 10/916,249, filed on 10 Aug. 2004; U.S. Ser. No. 10/932,986, filed on 2 Sep. 2004; U.S. Ser. No. 10/943,523, filed on 17 Sep. 2004; U.S. Ser. No. 10/981,001, filed on 4 Nov. 2004; U.S. Ser. No. 10/998,344, filed 24 Nov. 2004; U.S. Ser. No. 11/015,413, filed on 17 Dec. 2004; U.S. Ser. No. 11/035,800, filed on 13 Jan. 2005; U.S. Ser. No. 11/119,048, filed on 2 Feb. 2005; and U.S. Ser. No. 11/050,288, filed on 28 Apr. 2005.

FIELD OF THE INVENTION

The invention relates generally to mobility-based systems, methods and devices for analyzing samples. More particularly, in various embodiments, the invention relates to improving the filtering and detection capability of ion mobility based systems using charge building compensation techniques.

BACKGROUND

Several approaches to chemical identification are based on the recognition that ion species have different ion mobility characteristics under different electric field conditions at atmospheric pressure. These approaches include time-of-flight Ion Mobility Spectrometry (IMS) and differential mobility spectrometry (DMS), the latter also known by other names such as field asymmetric ion mobility spectrometry (FAIMS). Atmospheric-pressure chemical ionization enables these identification processes (including radioactive, ultraviolet and electrospray ionization, for example).

In a conventional IMS device, a weak DC field gradient is established between an upstream electrode and a downstream collector electrode and then an ionized sample is released into the DC field. The ionized sample flows toward the collector electrode. Ion species are identified based on the time of flight of the ions to the collector. The DC field is weak where ion mobility is constant.

A typical DMS device includes a pair of opposed filter electrodes defining an analytical gap between them in a flow path (also known as a drift tube or flow channel). Ions flow into the analytical gap. A compensated high-low varying asymmetric RF field (sometimes referred to as a filter field, a dispersion field or a separation field) is generated between the electrodes transverse the ion flow in the gap. Field strength varies as the applied RF voltage (sometimes referred to as dispersion voltage, separation voltage, or RF voltage) and size of the gap between the electrodes. Such systems typically operate at atmospheric pressure.

Ions are displaced transversely by the DMS filter field, with a given species being displaced a characteristic amount transversely toward the electrodes per cycle. DC compensation is applied to the electrodes to compensate or offset the transverse displacement generated by the applied RF for a selected ion species. The result is zero or near-zero net transverse displacement for that species, which enables that species to pass through the filter for downstream processing such as detection and identification. Other ions undergo a net transverse displacement toward the filter electrodes and will eventually undergo collisional neutralization on one of the electrodes.

One limitation of convention DMS systems is that the compensation voltage applied to the filter electrodes typically generates fringe fields that force ions to impact and deposit charge along the flow path of the system adjacent to the filter. As the ions deposit their charge, a charge build up occurs that counteracts the influence of the fringe fields and allows for subsequent stable ion detection. Unfortunately, the period of time in which the DMS system reaches stable ion detection introduces response time delays, especially in a system performing multiple sample detections, which may reduce the speed and responsiveness of current DMS systems. Also, the dependence on a charge build up to enable stable ion detection may adversely effect the stability and sensitivity of the DMS system where the charge build up is dependent on other variable factors such as surrounding environmental conditions.

Another is issue is that ions near an ion filter tend to be distributed in a fire-hose pattern based on the compensation voltage setting and the fringe fields when the compensation voltage is scanned over a range of voltages. Thus, the ions exiting the ion filter are sprayed onto the surfaces adjacent to the filter where charge builds up or accumulates.

SUMMARY

Systems and methods of the invention generally relate to processing a sample in an ion flow path of a ion mobility based analyzer. In various embodiments, the processing includes ion filtering and/or ion separating. In various other embodiments, the invention also includes ion species detection and identification.

Ion behavior within the flow path of an ion-based chemical analysis device can be controlled and manipulated to improve or even optimize system performance. Practices of the invention include using control structures to improve DMS ion species analysis. These control surfaces are variously employed for dissipating charge and/or for forming a controlling electric field.

More particularly, the invention compensates for the adverse effects of compensation voltage fringe fields and charge buildup in the flow path that may exist both upstream and downstream of a DMS filter. By counteracting or compensating for these fringe fields and the charge buildup in the flow path, the sensitivity, stability, and responsiveness of a DMS system is enhanced. The systems described herein may employ numerous techniques to counteract the effects of compensation voltage fringe fields including: removing portions of the substrate that define the flow path through a DMS system, utilizing porous and/or permeable materials along the flow path that enable the introduction of gas flow into the flow path for controlling the flow of ions, and employing control electrodes capable of redirecting compensation voltage fringe fields substantially away from the ions in the flow path of a DMS system.

The system may employ additional techniques to counteract and/or compensated for charge buildup in the flow path including controlling the range of compensation voltages used by the DMS system. For example, by scanning compensation voltages over a range of positive and negative voltages, the compensation field is reversed for a portion of the filter process which distributes the ion flow more evenly and reduces an accumulation of charge at certain locations in the DMS system. Also, the DMS system may identify an offset or bias which may be introduced by charge buildup or by electronic noise within the DMS, and then report or compensate for the offset when producing a spectrum output.

In one practice of the invention, an influencing structure and/or an influencing field influences the analytical environment within the analyzer such as to enhance stability of the analyzer. According to one feature, the influencing structure and field counteracts or overcomes various local effects that impact ion behavior. According to other features, the invention enables stabilizing ion analysis, as well as enabling focusing, trapping, confining, translating, selecting, steering, concentrating and/or filtering ions in the flow path of an ion mobility-based analytical system, such as an IMS or DMS system.

In one embodiment, the invention is integrated into a DMS system, which may be a spectrometer, filter, detector, separator, assembly, apparatus or the like. A flow path is defined that enables ionized sample to flow into the analytical gap defined between facing DMS filter electrodes in the flow path. Ion species are separated in the filter field and selected species are passed for downstream processing, such as for detection and identification, according to ion behavior in the compensated asymmetric RF filter field. Ion control is exercised within such device. In a further embodiment, the RF field is not compensated and ion control is implemented at control surfaces of the flow path.

In one embodiment, a control material in the flow path provides charge dissipating surfaces or structures that prevent or control charge buildup as impacts ion behavior in the system. In such embodiment, this material provides a discharge path for charges deposited on such surfaces, reducing or eliminating surface charges in the flow path, to control effect upon or interaction with the intended ion analysis.

In another embodiment, we provide active control structures for controlling various fields, artifacts, or the like, such as fringing effects at the filter electrode edges. In another embodiment, we achieve ion control (such as focusing or concentrating ions by field control), wherein electrodes, such as a grid or array of electrodes, are driven to selectively generate a non-uniform field. The non-uniform field is used to position ions in the ion flow. This positioning may include focusing and/or concentrating all ions in a flow to a specific flow path location or into a specific flow profile, or may include concentrating only a selection of ions in the flow which separate from other ions in the flow. This same set of electrodes can be driven to gate ion flow, such as for time of flight analysis.

The invention has other aspects, such as enabling ion steering and ion flow compensation, including selective changes of ion flow from one flow path to another flow path. This innovation may be placed within one device or may assist coupling from one system to another system (e.g., from a DMS to a mass spectrometer).

In a further embodiment, the flow path includes control surfaces in contact with a plurality (i.e., an array, grid, or set) of control electrodes. This "control array" may passively (e.g., by using a dissipative surface) or actively (e.g., by applying a control field) affect ion behavior in the flow path. This control function may be performed along a flow path structure, layer, surface, covering, coating, substrate, region, or the like.

In several embodiments, the invention employs a control structure that is generally described herein as "partially conducting", which refers to having some capacity to conduct a charge, but without impairing function of neighboring electrodes. This control structure may also include use of a plurality of control elements whose combined effect is to be partially conducting, although individual elements may be fully conductive.

In a charge dissipating embodiment of the invention, the overall effect of being "partially conducting" can be understood in the sense of being conductive enough to enable bleeding off or neutralizing of charge as it is being built-up on flow path surfaces but sufficiently resistive so as to be able to support a voltage gradient. Charge build-up can interfere with stability of an ion-based analytical system and therefore removal of the effect of charge buildup is a benefit of an embodiment of the invention.

Partially conducting material may include resources such as semiconductor material, resistive paint, doped glass, use of ion implantation, or the like applied to a substrate. The resistance of the material overall may be governed by selected geometry and voltage, as well as material properties. In various embodiments of the invention, a range of resistance is about $10^2 \leq$ ohms/square $\leq$ about $10^{14}$, and in other embodiments, is within a range of about $10^7 \leq$ ohms/square $\leq$ about $10^{11}$.

In one practice of the invention, a DMS device has a structure that defines a flow path. The flow path includes facing partially conducting layers of control material with a plurality of control electrodes to form facing control arrays. The control arrays are addressed and driven to control motion of ions in the flow path. Such control layers enable conveying, controlling, separating, neutralizing, processing, and/or passing, selected ions and ion species. These arrays can provide the filter electrode function or can be isolated from the ion filter electrodes. These arrays may be used for charge dissipation as well as other ion flow control and separation functions.

According to various embodiments of the systems and methods for controlling ion behavior in an ion-based analysis system, described herein, the control can be static or dynamic, such as by supplying a constant or time-varying field. One embodiment includes an ion source, an ion flow path, an ion controller including surfaces facing the flow path, an ion filter including electrodes separated by an analytical gap, and a control system for controlling ion behavior between various electrodes. In one example, the control system generates at least one electric field, for example, for concentrating ions in the flow path, and/or increasing or decreasing density of particular ions in the flow path. In another embodiment, the concentrated ions are filtered according to ion-mobility-based behavior in the filter. Some advantages of achieving this level of field control are improved ion flow behavior, higher ion filtering efficiency and increased detection capabilities.

In one aspect, the invention includes a system for analyzing ions of a sample. The system includes a flow path for flowing ions of a sample and an ion filter for generating an asymmetric field and a compensation field in the flow path which passes through selected ions. The system also includes a controller for counteracting a charge buildup within the flow path.

In one configuration, the system counteracts the charge buildup by applying a set of compensation voltages to the ion filter to generate a set of compensation fields where a first portion of the compensation voltages are positive and a second portion of the compensation voltages are negative. The first portion and second portion of the compensation voltages may be substantially equal in number. The first portion and second portion of the compensation voltages may not be substantially equal in number.

In one feature, the system includes a detector for collecting a portion of the ions in the flow path. In another feature, the system counteracts the charge buildup by: measuring a first compensation voltage associated with a first ion intensity peak of ions collected at the detector for a selected ion species when a first asymmetric RF voltage is applied to the ion filter, measuring a second compensation voltage associated with a second ion intensity peak of the ions collected at the detector for a selected ion species when the an asymmetric RF voltage is substantially not applied to the ion filter, and then determining a zero-peak offset by subtracting the second compensation voltage from the first compensation voltage.

In another feature, the system counteracts the charge buildup by reporting the zero-peak offset. In a further feature, the system counteracts the charge buildup by correcting the position of an ion intensity peak with respect to a compensation voltage value based on the zero-peak offset. In one configuration, the system includes at least one control electrode that is positioned outside the flow path. The system counteracts the charge buildup by applying a bias voltage to at least one the control electrodes to direct a portion of the compensation field substantially away from the flow path.

In another configuration, the system includes at least one recess along the flow path that is substantially adjacent to the ion filter. The system may include at least one dissipation electrode within a recess. In one feature, the system counteracts the charge buildup by applying a bias voltage to the dissipation electrode(s) for removing charge build up within the recess.

In another configuration, the system includes at least one gas inlet located substantially adjacent to the ion filter. The system may counteract the charge buildup by introducing a gas flow into the flow path to direct the ion flow within the flow path to a substantially center position. In another feature, the gas inlet includes a separator. The separator may be include a porous material or a permeable material.

Thus, in various embodiments, the systems and methods of the invention provide better sensitivity, higher resolution and better performance for an ion-mobility based analytical device.

The following description sets forth details of various illustrative advantages, features, implementations and applications of the invention. More particularly, the illustrative embodiments of the invention are described with regard to a DMS device, a mass producible DMS chip assembly, and further innovations in ion control in a DMS device. It should be noted that the systems and methods of the invention are not limited to DMS applications, and that these descriptions are by way of illustration only and not intended to limit the scope of the invention.

BRIEF DESCRIPTION OF THE DRAWINGS

The foregoing and other objects, features and advantages of the invention will be apparent from the following illustrative description, along with the accompanying drawings, in which like reference characters refer to the same parts throughout the different views. The drawings are not necessarily to scale, emphasis instead being placed on illustrating the principles of the invention.

FIG. 4A is a side perspective view of a pair of partially conducting control material layers according to an illustrative embodiment of the invention.

FIGS. 4B-4D show electrode configurations according to illustrative embodiments of the invention.

FIG. 5A is a conceptual diagram of a portion of a DMS system where the filter electrode and shielding electrode are located on a substrate separated by a charge dissipation layer according to an illustrative embodiment of the invention.

FIG. 5B is a conceptual diagram of a portion of a DMS system where a charge dissipating electrode (or collection or array of electrodes) performs the charge dissipating function between a shielding electrode and filter electrode according to and illustrative embodiment of the invention.

FIG. 5C is a conceptual diagram of a portion of an analytical system where the dielectric material of the substrates at the DMS filter exit are removed to reduce the adverse effects of charge build up according to an illustrative embodiment of the invention.

FIG. 6E is a plot of compensation voltage versus field asymmetric RF voltage (for negative compensation voltages) that illustrates how the charging affects RF-on and RF-off peak positions nearly identically according to an illustrative embodiment of the invention.

FIGS. 9A-9D show alternative field effects according to illustrative embodiments of the invention.

DESCRIPTION OF ILLUSTRATIVE EMBODIMENTS

The invention, in various illustrative embodiments, enables improved ion mobility-based chemical analysis. One embodiment includes DMS ion species separation, detection and identification. The invention may be practiced with various systems where ion control is useful. One illustrative embodiment is implemented in a DMS chemical ionizer.

In practices of the invention, a DMS system receives a sample in a fluid flow, filters the ionized fluid flow, and passes ion species of interest for downstream processing. According to one practice, the ions are carried by a gas stream (sometimes referred to as a carrier gas) through stages of the system (e.g., into a DMS filter and toward a detector), as taught in U.S. Pat. No. 6,495,823, incorporated herein by reference. Alternatively, the sample may be conveyed via an electric propulsion field, with or without carrier gas, as taught in U.S. Pat. No. 6,512,224, also incorporated herein by reference.

Figure 1:
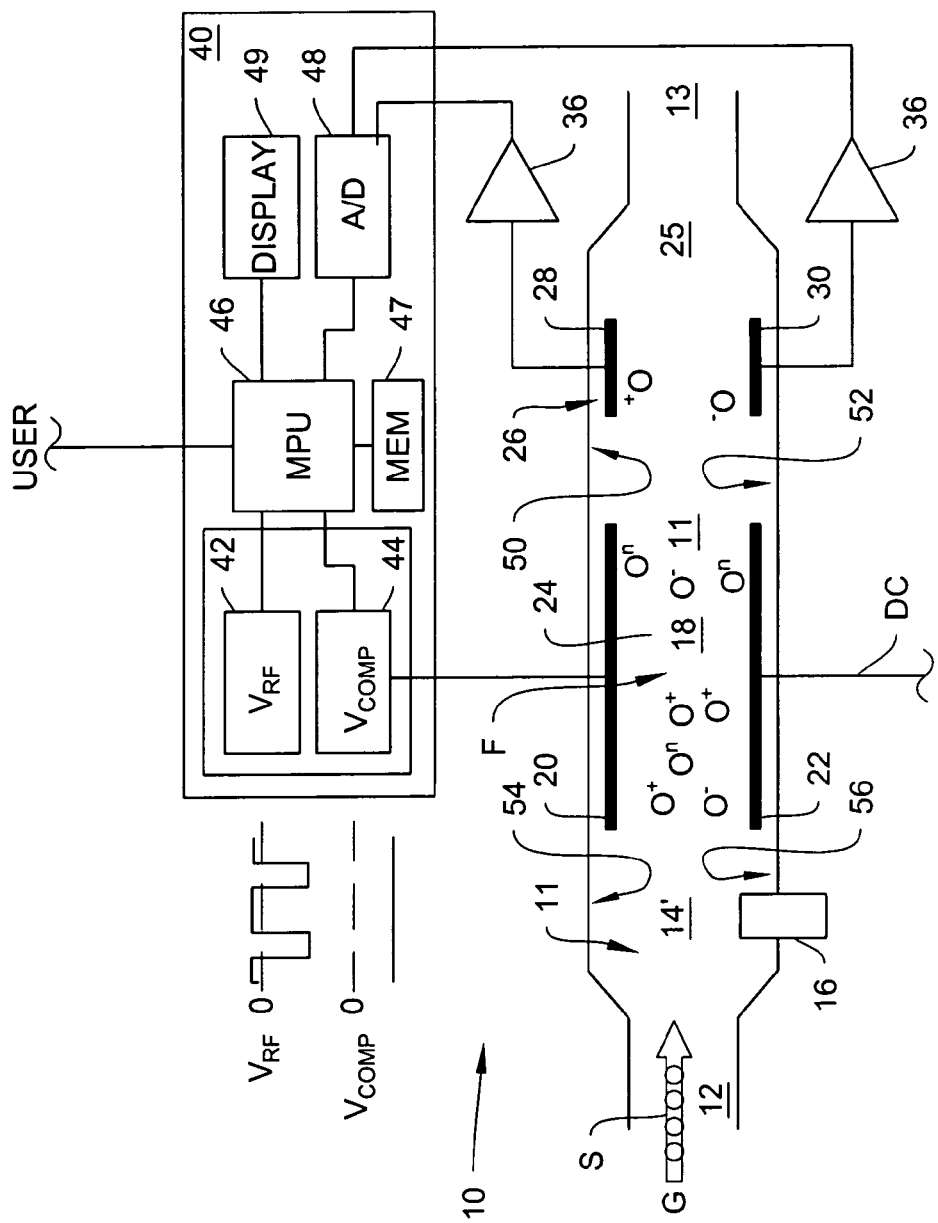
FIG. 1 is a schematic of a field asymmetric ion mobility spectrometer.

In an illustrative DMS assembly 10, as shown in FIG. 1, flow path 11 has inlet 12 for receipt of carrier gas flow G carrying sample S into the device. The sample is drawn from the environment or received from a front-end device, such as a gas chromatograph (GC), and flows from inlet 12 to ionization region 14 along the flow path 11. In one embodiment, portions of the flow path 11 are defined by dielectric (or insulator) substrate portions 50, 52, 54, and 56 that are positioned substantially adjacent to the filter electrodes 20 and 22.

Compounds in the sample are ionized by an ionization source 16 as the sample flows through ionization region 14, creating a set of ionized molecules ++, -- accompanied by some neutral molecules n, of various chemical species. According to one embodiment, ionized monomers and/or dimers, etc. are created during such ionization. Also, clusters of ions may be created when a monomer combines with water molecules or other background molecules.

In the embodiment of FIG. 1, carrier gas G carries the ions into analytical gap 18 (e.g., 0.5 mm) between filter electrodes 20 and 22 of ion filter 24. A compensated asymmetric RF filter field F is developed between the ion filter electrodes in the analytical gap. The strength of the field varies according to the applied RF voltage ($V_{RF}$). The RF field may be compensated, such as by application of a DC offset (Vcomp). Compensation may also be implemented by varying other aspects of the filter field, and is applied on a species-specific basis.

A detector 26 is incorporated into system 10, and takes the form of at least one electrode, and preferably includes a plurality of electrodes, such as, without limitation, opposed electrodes 28 and 30, associated with the flow path downstream of filter 24. However, alternatively, systems of the invention may include detecting the filter output with a mass spectrometer (MS) or other external detection system. In one embodiment, the invention improves species separation as a front-end device to enhance MS detection.

Control unit 40 performs a number of important actions in accordance with the invention, and may incorporate various devices or functions for this purpose. These may include RF voltage generator 42, an optional compensation voltage generator 44, a microprocessor unit (MPU) 46, memory 47, an analog-to-digital (A/D) converter 48, and display 49.

The microprocessor 46 provides digital control signals to the RF voltage generator 42 and the compensation voltage generator 44 to generate the desired compensated drive voltages for the filter 24. These devices may also include digitalto-analog (D/A) converters and the like, although not shown in detail. In the embodiment of FIG. 1, the control unit 40 biases and monitors the electrodes 28 and 30 of the detector 26. The microprocessor 46 correlates applied compensation and RF voltages with observed responses at the detector 26, via the analog-to-digital (A/D) converter 48. Matching of this detection data against stored detection data in the memory 47 enables identification of detected species. The system may be preprogrammed or may accommodate intervention by a "user".

According to various illustrative embodiments of the invention, applied peak RF voltages can range from less than about 1,000 V/cm to about 30,000 V/cm. The frequency may range from less than about 1 MHz to beyond about 20 MHz, depending upon species. In one embodiment, a duty cycle of about 30% is employed at higher frequencies for good effect, although other operating ranges, voltages, field strengths, duty cycles, wavelengths and frequencies may be employed in other illustrative embodiments of the invention.

In a DMS, ions are separated based on mobility differences in the filter field F in the analytical gap 18 according to the filter field conditions. Field F can be held at a fixed periodic value, where the system is dedicated to detecting particular ion species at a single data point, or the field conditions can be varied for generating a plurality of data points.

Additionally, at least one field parameter (such as DC compensation or RF duty cycle) can be scanned to generate a mobility scan. The field conditions are set to a particular value, except for at least one of such mobility-affecting parameters, which is swept through a range to generate a mobility spectrum for the sample under test. According to the illustrative embodiment, this is performed under direction and control of the control unit 40.

Figure 2A:
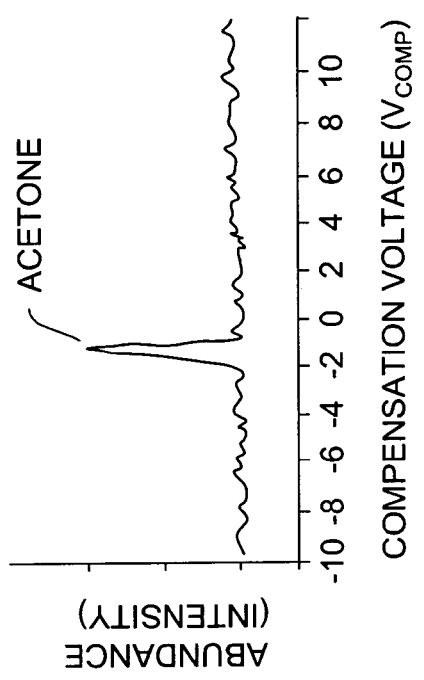
FIGS. 2A-2B show mobility scans plotting detection intensity versus compensation voltage for a given field strength in a DMS, for acetone alone, FIG. 2A, and for a combination of o-xylene and acetone, FIG. 2B.
Figure 2B:
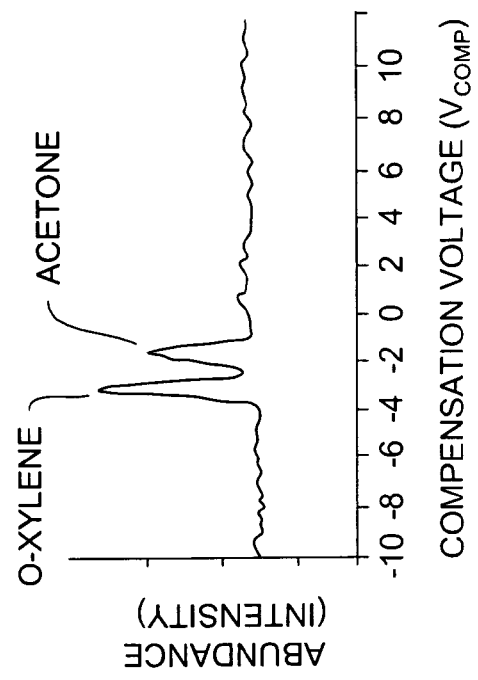

Illustrative examples of mobility scans based on the output from a DMS device are shown in FIGS. 2A-2B. In FIG. 2A a single compound, acetone, was submitted to a DMS analyzer. The illustrated plot is typical of the observed response of the DMS device, with detected acetone ions in this example forming a peak intensity at a compensation voltage of about −1.5 volts. This is useful information, such that future detections of a peak at this compensation in this device is indicative of acetone detection.

In FIG. 2B, the analyzed sample consisted of acetone and an isomer of xylene (o-xylene). FIG. 2B demonstrates unique detection peaks according to ion mobility characteristics for the different ion species, o-xylene and acetone. The acetone peak appears at about −2.5 volts while o-xylene appears at about −4 volts. Data representing these detection peaks can be compared against stored data for known compounds for this device and the applied RF field and compensation, and identification is made based upon a data match.

As can be seen, the above-described system 10 of the invention provides a stable DMS device capable of repeatable test results. In one practice, the invention uses a library of information for identifying detected species, in view of compensation, RF and other field conditions. It is also within the scope of the invention to calibrate the system using the reactant ion peak (RIP) and/or a dopant peak, for example, among other techniques.

Figure 3A:
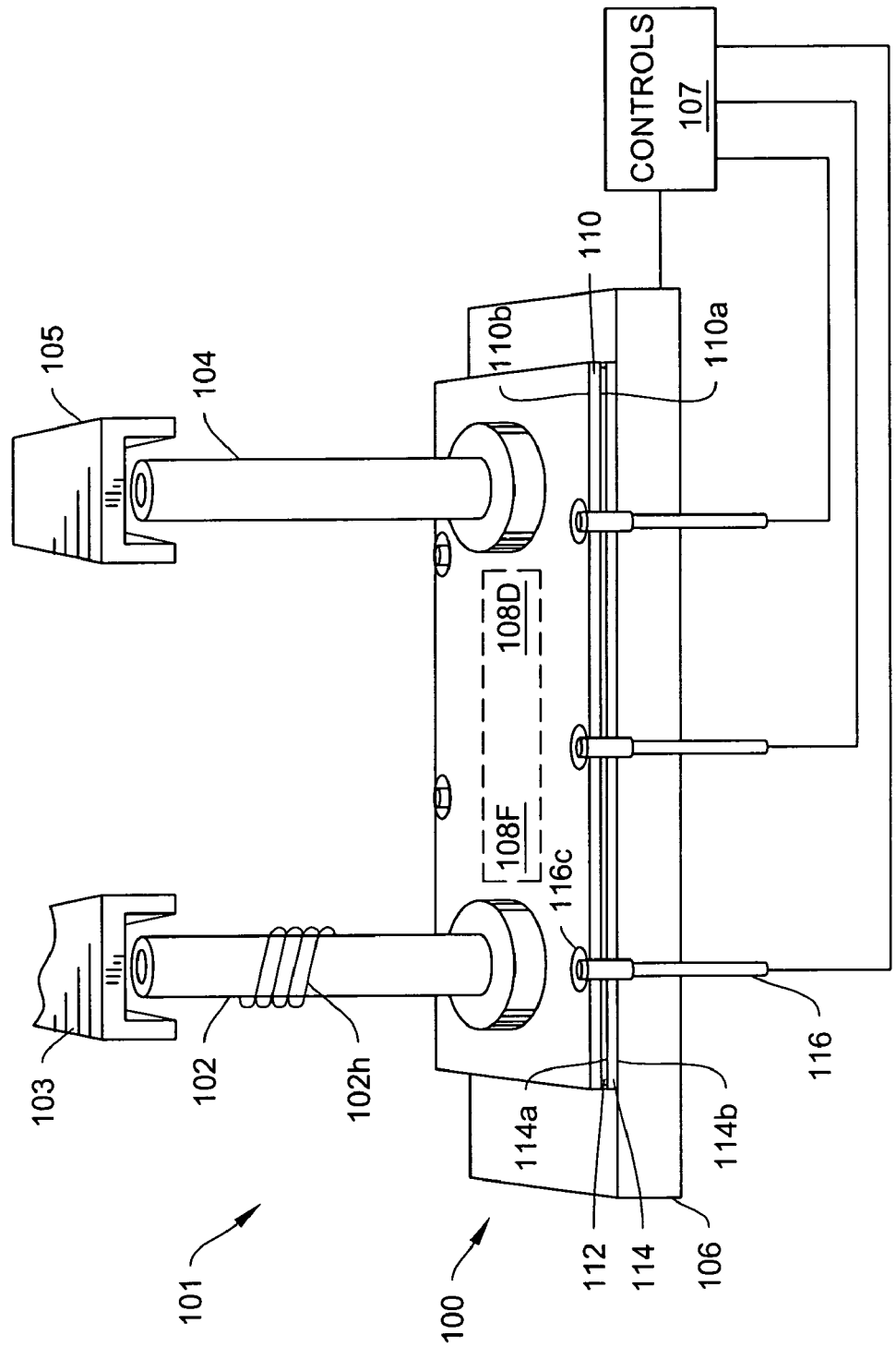
FIG. 3A is a side perspective view of a DMS system according to an illustrative embodiment of the invention.

In certain embodiments, improvements may be incorporated into a mass producible DMS chip 100, formed into an analytical assembly 101, as shown in FIG. 3A. In an exemplary embodiment, chip 100 includes components shown in FIGS. 3B-3D. In another embodiment, a portion or all of the components of the assembly 101 are integrated in a monolithic structure including plastic, ceramic, and alumina. Additional, portion or all of the supporting electronics for a DMS system may be incorporated into the monolithic structure. Assembly 101 performs an I/O function, a processing function, and a control function. According to the embodiment depicted by FIG. 3A, the I/O function includes an inlet tube 102 for receipt of a gas sample from the environment (or from a GC output 103 or the like), and an outlet tube 104, which may be coupled to a pump 105 for exhaust of gas flow. (While inlet and outlet tubes are shown, alternative passages, pathways, orifices, openings, apertures, or other mechanisms of connection, ingress and egress, are within the scope of the invention.)

Chip 100 is preferably mounted into socket 106, which may be a conventional DIP or a custom socket, for off-board connection of the chip, such as for communication with off-board drive and control electronics 107. In one embodiment, all components of the assembly 101 are integrated, assembled, and/or formed onto a the same substrate or substrates wherein some or all of the filter electrodes, detector electrodes, control electronics, and other supporting electronics share the same substrates and/or assembly. Spectrometer system 101 functions in a manner similar to the system 10 described above, wherein the flowing sample is ionized and is filtered in the filter section preferably according to the DMS techniques.

An illustrative chip 100 includes filter 108F and detector 108D (indicated by dotted outline on the face of chip 100 in FIG. 3A). The system is controlled and ion detection signals are evaluated and reported by the controller section 107. Controller 107 may be on-board or off-board. According to this embodiment, the chip 100 has electrical connectors, such as leads 116, bonding pads 116c, or other connection arrangements, enabling connection to off-board systems, controls and the like.

Figure 3B:
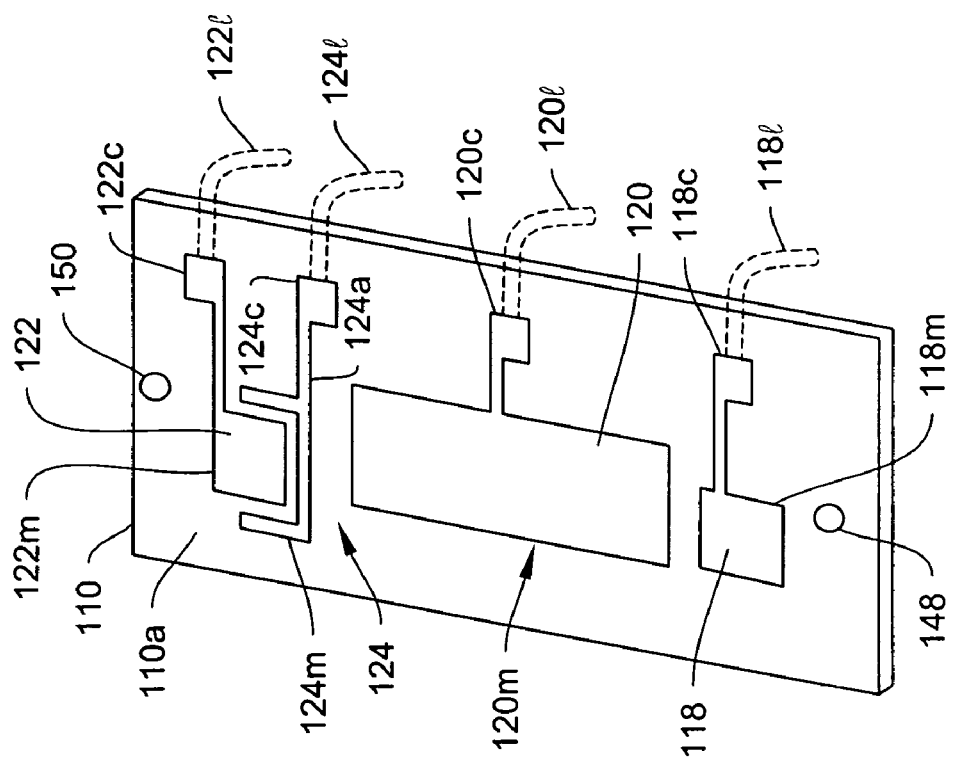
FIGS. 3B-3C are perspective views of substrates with electrodes in practice of the embodiment of FIG. 3A.
Figures 3C, 3D:
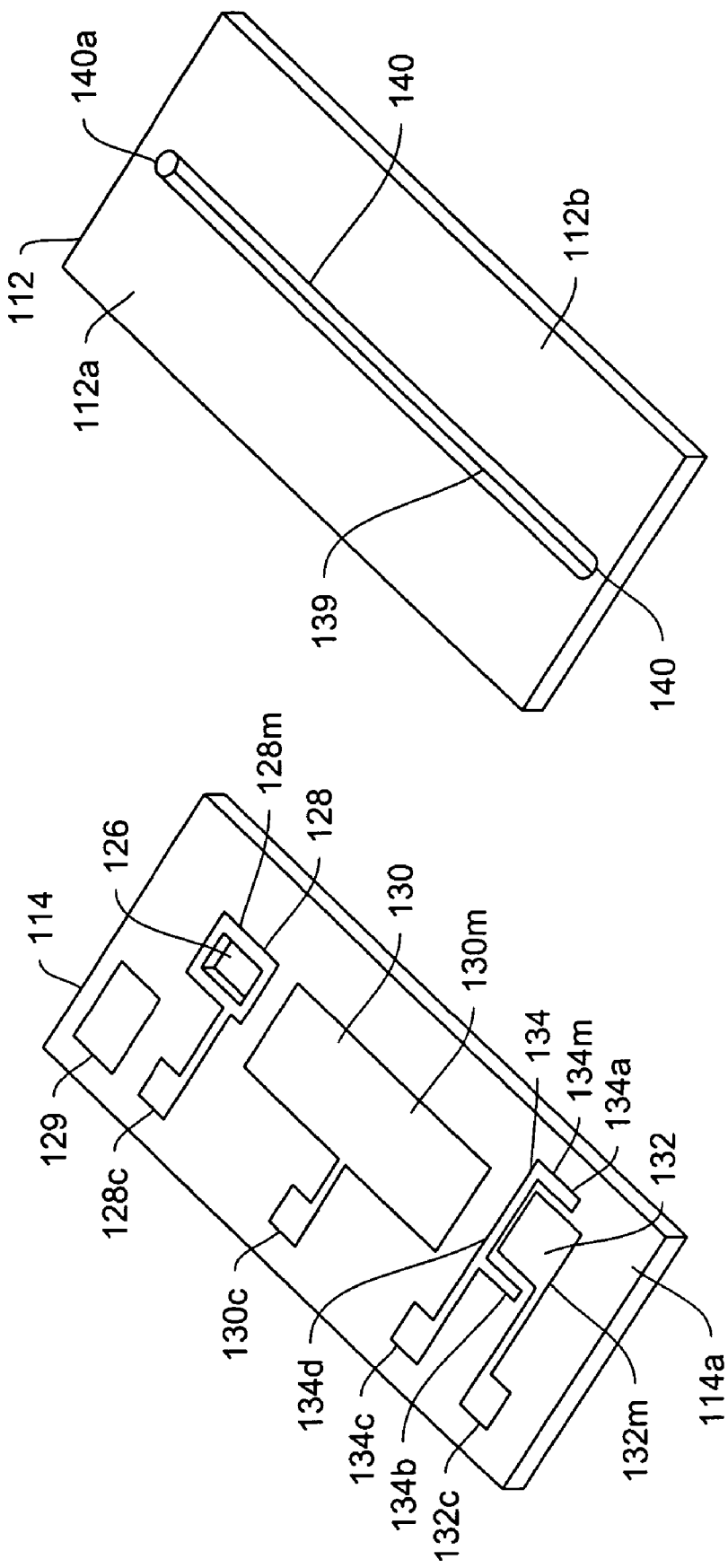
FIG. 3D is a perspective view of an exemplary spacer frame illustrative of the type that may be employed in the embodiment of FIG. 3A.
Figure 3E:
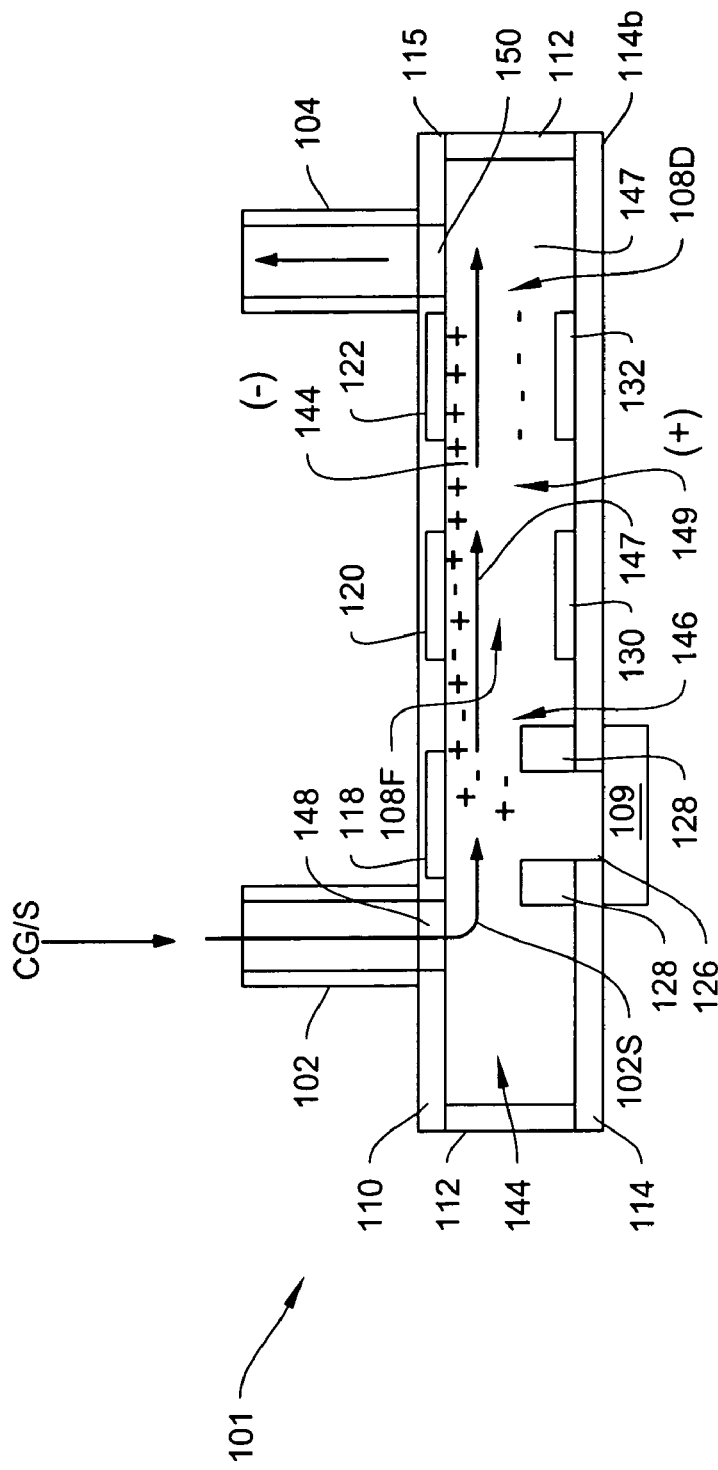
FIG. 3E is a side schematic view of a DMS device according to an illustrative embodiment of the invention.

According to one practice, the chip 100 includes substrate 110 (see FIGS. 3A and 3B) and substrate 114 (see FIGS. 3A and 3C). These substrates are separated by a spacer frame 112 (see FIGS. 3A and 3D). Substrates 110 and 114 and spacer frame 112 are sealed together to form an enclosed flow path (with an enclosed channel 140) while forming a sealed housing 115 (FIG. 3E). The inlet tube 102, outlet tube 104, ion source 109 and electrical leads 116 are mounted on the housing. In one embodiment, the inlet tube is provided with an optional heater 102h (FIG. 3A), for heating the sample input.

Ionization of chemical sample in practice of the invention may be achieved by various techniques. Ionization source 109 may be an ultraviolet photo-ionization lamp, a plasma or radioactive source, ESI arrangement, laser ionization, or the like, and provides a mixture of ions corresponding to chemicals in the gas sample. The ionized sample is then passed to ion filter 108F where the applied compensated RF field between the filter electrodes selects and enables a particular ion species to pass through the filter. Once through the filter, the ion species is detected in detector 108D. If the filter field is scanned, then a detection spectrum can be generated for the sample.

In the embodiment of FIG. 3E, an ionization source 109 is integrated into chip 100 to ionize the sample in the gas flow from inlet 102, which is drawn through the DMS filter 108F by pump 105, under direction of drive and control electronics 107, similar to the function described above for chemical sensor system 10.

In the embodiment of FIG. 3A, inlet tube 102 and outlet tube 104 are mounted to the back surface 110b of substrate 110. As shown in FIGS. 3B-3E, the inner surface 10a of substrate 110 and inner surface 114a of substrate 114 include metallization patterns for defining an illustrative DMS system. As shown in FIGS. 3A-3E, an illustrative system of the invention includes substrate 110 having first metallization portion 118m (FIG. 3B) that defines attraction electrode 118 and its extension that forms bonding pad 118c to which a lead 118l is attached. In one embodiment, the controls 107 are integrated with the substrate 114, substrate 110, and/or socket 106. Substrate 110 further includes a second metallization portion 120m that defines filter electrode 120, and its extension that forms bonding pad 120c to which a lead 120l is attached. Substrate 110 also includes third metallization portion 122m that defines detector electrode 122 and its extension that forms bonding pad 122c to which a lead 122l is attached.

First substrate 110 includes fourth metallization portion 124m that defines shielding electrode 124 and its extension that forms bonding pad 124c (to which a lead 124l will be attached). Shielding electrode 124 further defines shield 124a which shields detector electrode 122 from the RF filter signals, thus reducing leakage between the ion filter 108F and detector electrode 122 of detector 108D, and thus reducing noise in the ion detection signal.

As shown in FIGS. 3C and 3E, ionization access port 126 (a via or through hole) is defined in either or both substrates to enable ionization sources 109 to interact with the sample. Source 109 is shown mounted on the back side 114b of substrate 114 in FIG. 3E.

As shown in FIG. 3C, the front side 114a of substrate 114 includes first metallization portion 128m, through which port 126 extends, and defines a guiding electrode 128 and its extension that forms bonding pad 128c to which a lead (not shown) is attached.

As shown in FIG. 3C, substrate 114 further includes second metallization portion 130m that defines filter electrode 130 and its extension that forms bonding pad 130c to which a lead can be attached. Substrate 114 also includes third metallization portion 132m that defines detector electrode 132 and its extension that forms bonding pad 132c to which a lead can be attached.

Substrate 114 of FIG. 3C also includes fourth metallization portion 134m that defines shielding electrode 134 and its extension that forms bonding pad 134c to which a lead can be attached. Segment 134m further defines shields 134a, 134b, 134d which shield detector electrode 132 from the filter signals, thus reducing leakage current between filter 108F and detector electrode 132 and thus reducing noise in the ion detection signal. The substrate 114 may also include electronics section 129. In one embodiment, electronics section 129 includes all or a portion of the electronics for a DMS system. For example, the electronics section 129 may include a controller such as controller 40, amplifiers such as amplifiers 36, asymmetric voltage generation circuit(s), compensation voltage generation circuit(s), one or more microprocessors, one or more memory components, one or more analog-to-digital converters, power supply components, and any other supporting electronics for the DMS system such as DMS system 10. In another embodiment, the electronic components of the electronic section 129 are distributed throughout various locations and/or positions of the substrate 114.

Spacer (or spacer frame) 112 is preferably a strip of insulating material (which itself may be semi-conductive or otherwise static or charge dissipative) with a central through-slot 139 that cooperates with the substrates 110, 114 to define the drift channel 140. The sides of drift channel 140 are contained within the spacer frame 112 extensions 112a and 112b. Substrate 110 is placed on one side of spacer 112 and substrate 114 is placed on the other side of spacer 112. The workpiece is processed to set and form a sealed structure.

Illustratively, this structure, shown in FIG. 3E, forms the basic chip assembly 100 and defines an enclosed and sealed flow path 144 with access for fluid introduction into the flow path. The flow path is accessed at one end 140a (as shown in FIG. 3D) of channel 140 by, and is in fluid communication with, inlet tube 102 mounted over port (or through hole) 148 in substrate 110. The flow path 144 is vented at the other end 140b (as shown in FIG. 3D) by, and is in fluid communication with, outlet tube 104 mounted over port (or through hole) 150 in substrate 110.

In operation, a carrier gas including a chemical sample (CG/S) to be detected, is introduced as flow 102s into flow path 144 via inlet tube 102, and then passes into ionization region 146 and is subjected to the ionization source 109. In one embodiment, source 109 emits ions that pass through port 126, guided by a bias applied to guiding electrode 128 (e.g., a positive bias for a positive ion) and attracted by attraction electrode 118 into the flowing sample 102s. The attraction electrode is driven by an attraction bias (e.g., a negative bias for a positive ion). The ions ionize compounds in sample flow 102s creating ions ("+", "−") that are carried in the flow between electrodes 120, 130 of filter 108F, where the ions are subjected to the compensated high field asymmetric waveform ion mobility techniques (as described earlier), and filtered (selected) ions pass through the filter. Ion species are detected at electrodes 122, 132 of detector 108D. The carrier gas flow then vents from the flow path 144 at outlet 104.

The flow path 144 may be at, above or below ambient pressure. In some applications, the carrier gas and sample flow is generated by a higher pressure at the inlet, such as produced when eluting samples from a GC, and the sample is carried along the flow path thereby. In another application, the flow is generated by a pressure gradient at the detector, such as at the inlet of an MS and the gas is drawn thereby. As depicted by FIG. 3A, the gas flow may also be generated by a pump 105 at outlet 104. This enables operation at different pressures as selected for specific species identifications.

Figure 3F:
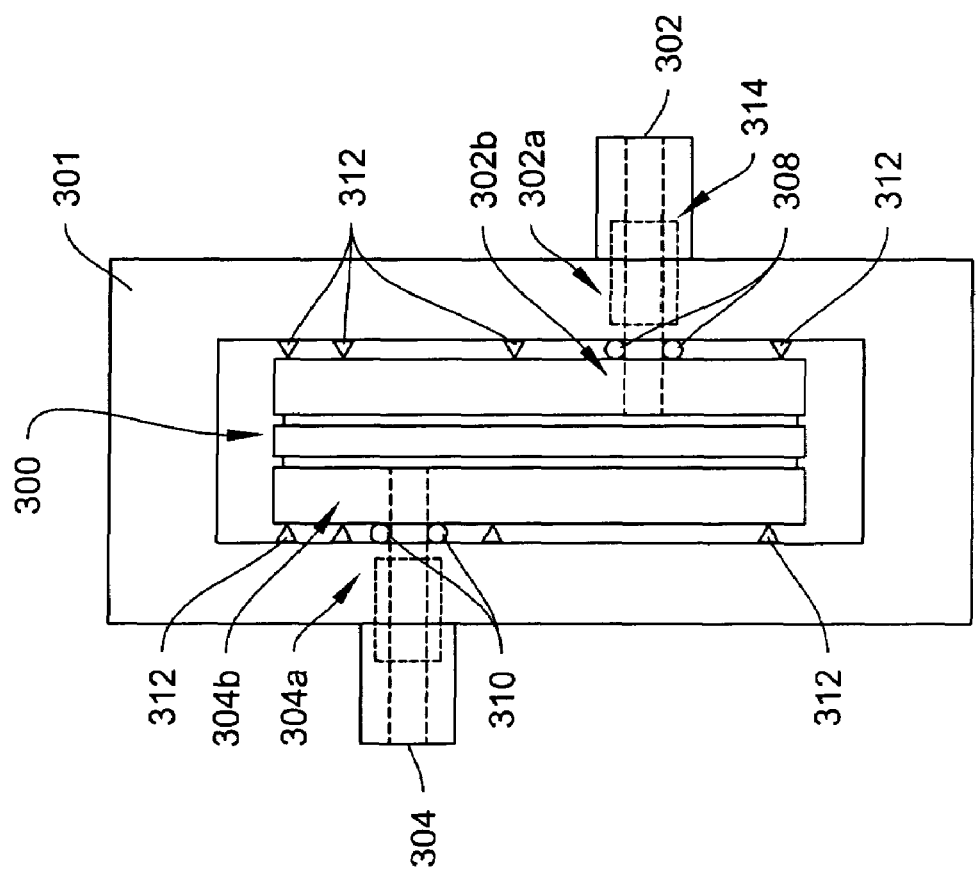
FIG. 3F is a schematic of a disposable DMS device with socket according to an illustrative embodiment of the invention.

It is further noted that while a particular pinout is shown in FIG. 3A for mounting chip 100 in socket 106, alternative configurations are possible, all within the scope of the invention. For example, as shown in FIG. 3F, a DMS chip assembly 300 embodiment of the invention is mounted into a socket 301, wherein an inlet 302 on the socket provides input flow into chip 300 via ports 302a and 302b and an exhaust is provided at outlet 304 via ports 304a and 304b. In this embodiment, sealing elements 308 and 310, such as o-rings, ensure a substantially leak-free coupling of the chip 300 to the socket 301 and between cooperating ports 302a-302b and 304a-304b. An ionization source is preferably encompassed within chip 300. In one illustrative embodiment, source 314 is formed associated with inlet 302, wherein a flow of ions is supplied to the internal flow path. The chip and socket combination enable implementation of a system such as shown herein, and may be provided with connectors 312 for communication with the electronic drive and control part 40 (of, for example, FIG. 1).

Ion Control

Illustrative embodiments of the invention feature ion charge dissipative and/or controlling aspects. In one embodiment, charge dissipative parts of the flow path prevent charge buildup that otherwise can impact ion behavior. In another embodiment, electronic control of ion behavior provides optimization of mobility-based ion species filtering and control.

The charge dissipative and electronic control aspects may be implemented from the same surfaces or structures or may be separately implemented.

In an illustrative practice, the invention employs a structure of partially-conducting control material supporting a plurality of control electrodes in the ion flow path. These supported control electrodes are laid out as an addressable array (which may be a grid of electrodes). Controlled voltages are applied to such addressable array to affect and control local ion behavior in the flow path. This control function of the invention may be achieved using a material element or elements (in the flow path) having the capacity to conduct a charge while simultaneously maintaining sufficient electric separation between electrodes in conductive contact with that material to avoid excessive or unwanted current flows.

Such control material is generally described herein as "partially conducting," which may also include materials that are somewhat "resistive." As well, several partly- or fully-conductive elements may be gathered in an area to perform a control or a charge dissipating function.

In illustrative embodiments, the partially conducting control material may be a structure, layer, surface, covering, coating, substrate, region, or the like. In one embodiment, the control material is associated with control of an addressable array of electrodes. In one illustrative embodiment, resistive paint (used in electronic circuit applications) is applied to a non-conducting substrate with an array of electrodes formed thereon. In another illustration of such control material, a sheet of semi-conducting material is used as a partially-conducting member and as a support member (e.g., a substrate) for the array of electrodes that are used for such control function. Illustratively, the partially-conducting control material is tied to a potential or ground to dissipate the charge build-up threat.

FIG. 4A shows DMS chip 200 in which electronic control of ion behavior is obtained. This electronic control is implemented via partially-conducting control material which forms surfaces of chip 200. In particular, flow path 201 is defined between structures 210 and 214. The structures 210 and 214 are formed as, using, or in cooperation with, partially-conducting control material layers 211 and 215, respectively, and in a one illustrative embodiment, such arrangement also provides substrate support.

Each of the partially-conducting control material layers 211 and 215 includes an electrode, or, as shown, includes an array of electrodes 211U and 215D, respectively. The arrangement of electrodes for a particular array may be chosen for particular purposes. For example, the arrays may be driven to concentrate or focus ions in the ion flow in the filter.

In one embodiment, the arrayed electrodes are used for charge dissipation. In another embodiment, they are used for ion flow control. In another embodiment, they are used for both functions. Illustrative array patterns are shown in FIGS. 4A-4D. The arrays may be formed on an insulating surface or directly on charge-dissipating surfaces in a practice of the invention.

In an illustrative embodiment, the arrays face each other and enable forming and controlling the DMS filter field F across the flow path. Such arrangement enables forming a non-uniform filter field which enables focusing or concentrating desired ion flow (such as focusing toward the center of the ion in the flow path). In one practice of the invention, at least one array is employed, which faces at least one electrode but preferably faces an opposed array of electrodes on opposed sides of flow path 201, and which are driven to create the non-uniform field to achieve such concentrating effect. It should be noted that a uniform field may not achieve such ion focusing.

Referring to the illustrative embodiment of FIG. 4A, arrays 211U and 215D, are formed on partially-conducting control material layer 211 and 215, respectively. These arrays include a plurality of electrodes, such as electrodes 211a-211n of array 211U and electrodes 215a-215n of array 215D, in the pattern shown in FIG. 4B. For ease of illustration, layer 211 is treated as if transparent, wherein it will be understood that electrodes 211a-211n forming array 211U are, in fact, on the inner face of layer 211. Also included are leads 211al-211nl for communication therewith. A like configuration is applied to layer 215 with electrodes 215a-215n of array 215U and leads 215al-215nl. The arrays face each other across flow path 201.

Figure 4E:
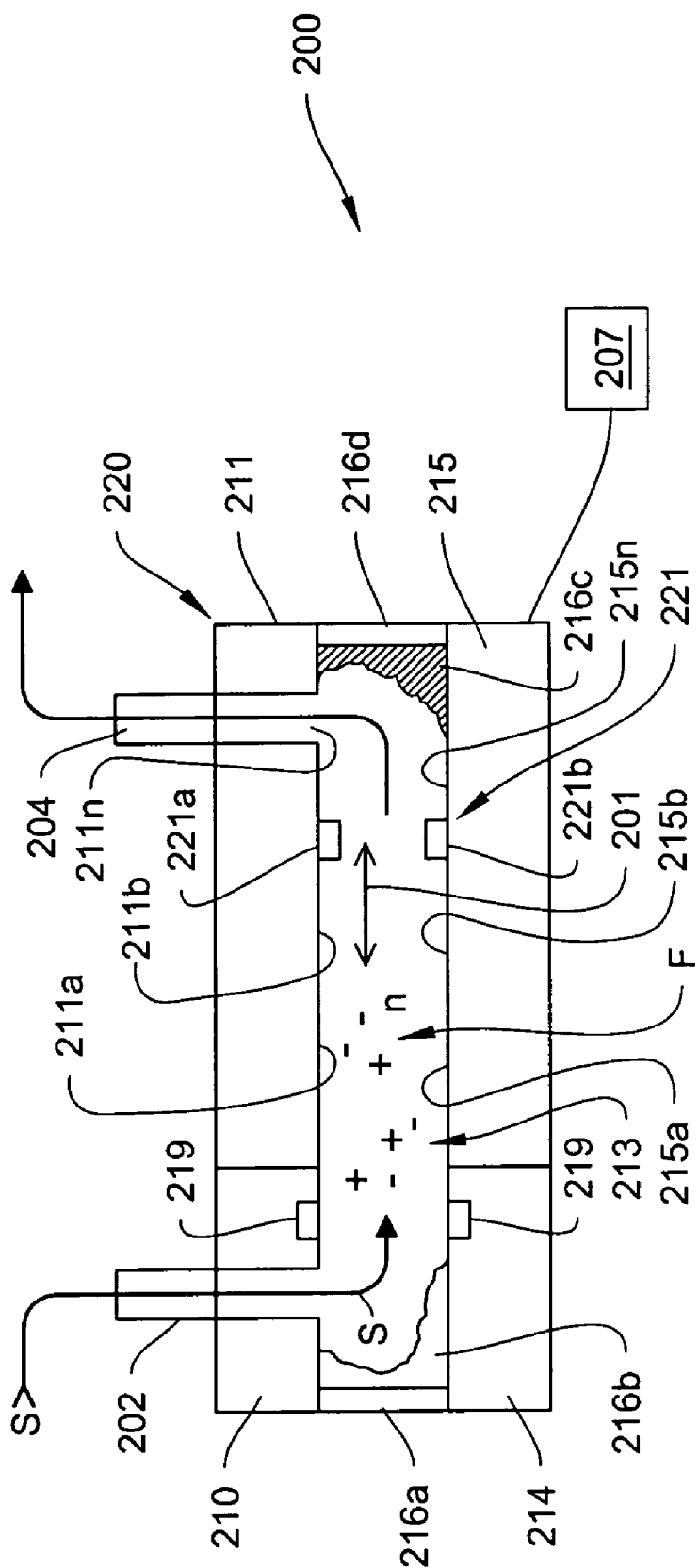
FIG. 4E is a side view of a DMS system according to an illustrative embodiment of the invention.

As shown in FIG. 4E, structures 210 and 214 act as support members (e.g., like substrates) and cooperate with spacing sidewalls 216a-216d, to form a housing or package 220 for DMS chip 200. Sidewalls 216b and 216c are shown in partial view for clarity. These sidewalls may be formed in various manners and may form all or several sides of the chip. For example, sidewalls 216 may be discrete such as by using a spacer frame 112, as earlier set forth, or may be formed as extensions of the structures 210 and 214, as shown in FIG. 4E.

Sidewalls 216a-216d may be used as confining electrodes or for charge dissipation, and may include conducting or partially-conducting surfaces. These sidewalls may be tied to a potential or to ground or may be driven as per the other electrodes of the invention.

In one illustrative embodiment, the sidewalls are defined by spacer frame 112 (FIG. 3D) which is formed of a dielectric material. In one illustration, a negative potential is applied to the spacer frame such that the sidewalls act as concentrating electrodes to concentrate ions toward the center of the flow path, which intensifies the analyte for downstream analysis.

Returning to FIG. 4E, the I/O function of chip 200 includes an inlet tube 202 for receipt of a gas sample from the environment (or from a GC outlet or the like), and an outlet tube 204 which may be coupled to a pump (not shown) for exhaust of air flow and/or delivery of filtered ions for further downstream processing. An ionization source 219 may also be provided which may include UV, Ni63, ESI, corona discharge, atmospheric pressure chemical ionization (APCI), matrix-assisted laser desorption ionization (MALDI), plasma, or the like.

As shown in FIG. 4E, the chip 200 includes ion filter 213, which functions similarly to filter 108F of chip 100, and preferably also includes a detector 221, similar in function to detector 108D of chip 100. Electronic ion control is provided by a controller 207, similar to controller 107 associated with chip 100 (FIG. 3A), or controller 40 associated with apparatus 10 (FIG. 1). The system is controlled and ion detection signals are evaluated and reported by the controller 207. Chip 200 has electrical connectors, such as leads 211al-211nl and 215al-215nl, enabling connection to the controller 207, whether it is situated on or off-board of chip 200.

In operation, sample S is drawn in through inlet 202 and flows along flow path 201. If the sample flow is not yet ionized then it is being subjected to ionization source 219. In any event, ions ++, −−, and n flow along the flow path toward outlet 204 and into filter 213. Electrodes 211a-211n, and 215a-215n, of the respective control arrays 211U, 215D are addressed, and controlled DMS voltages are applied to such electrodes, to create a compensated RF field F to affect ion behavior in ion filter 213. Ion species of interest are thus passed through filter 213. Illustratively, the passed ions are detected at on-board detector electrodes 221a and 221b of detector 221 (FIG. 4E), which function in the manner discussed above with respect to DMS system embodiments 10 (FIG. 1) and 100 (FIG. 3A).

FIGS. 5A and 5B show several further illustrative charge dissipating applications of the invention, implemented on substrate 110. Spacer 112 and the other substrate 114 are not shown, but may also be adapted accordingly.

As shown in FIG. 5A, filter electrode 120 and shielding electrode 124 are located on substrate 110 separated by a charge dissipation layer 222. In FIG. 5B, a charge dissipating electrode (or collection or array of electrodes) 223 performs the charge dissipating function between electrodes 120 and 124. In these embodiments, charge dissipation reduces, or in some instances minimizes, charge buildup and facilitates an improved ion analysis by conducting charge away from the ion flow and from the analytical region of the flow path.

FIG. 5C is a diagram of a portion of an ion-based analytical system 200 where the dielectric material of the substrates 225a and 225b at the DMS filter 124b exit are removed to reduce the adverse effects of charge build up. In FIG. 5C, an ion-based analytical system 200 includes cooperating substrates 225a and 225b. Relief from charge buildup is provided by recesses 224a and 224b located where the charge might otherwise build and interfere with the ion flow. More particularly, and referring to substrate 225b (it being understood that cooperating substrate 225a is similar and therefore is not shown in detail), it will be seen that recess 224b is formed to effectively relocate the area where charge buildup might otherwise occur along the flow path between electrodes 120b and 124b. The effect is to lessen or prevent unwanted charge buildup from interfering with local ion flow. The result is improved stability of ion-based analytical system 200.

Optionally a charge dissipating layer 222b also is formed at the bottom and/or sides of recess 224b to further ensure reduction, or in some instances minimization, of charge buildup. The result is improved stability of ion-based analytical system 200. In FIG. 5C, the effects of charge buildup are reduced by recessing the charge building surfaces away from local electrodes, such as achieved with recesses 224a and 224b.

Figure 5D:
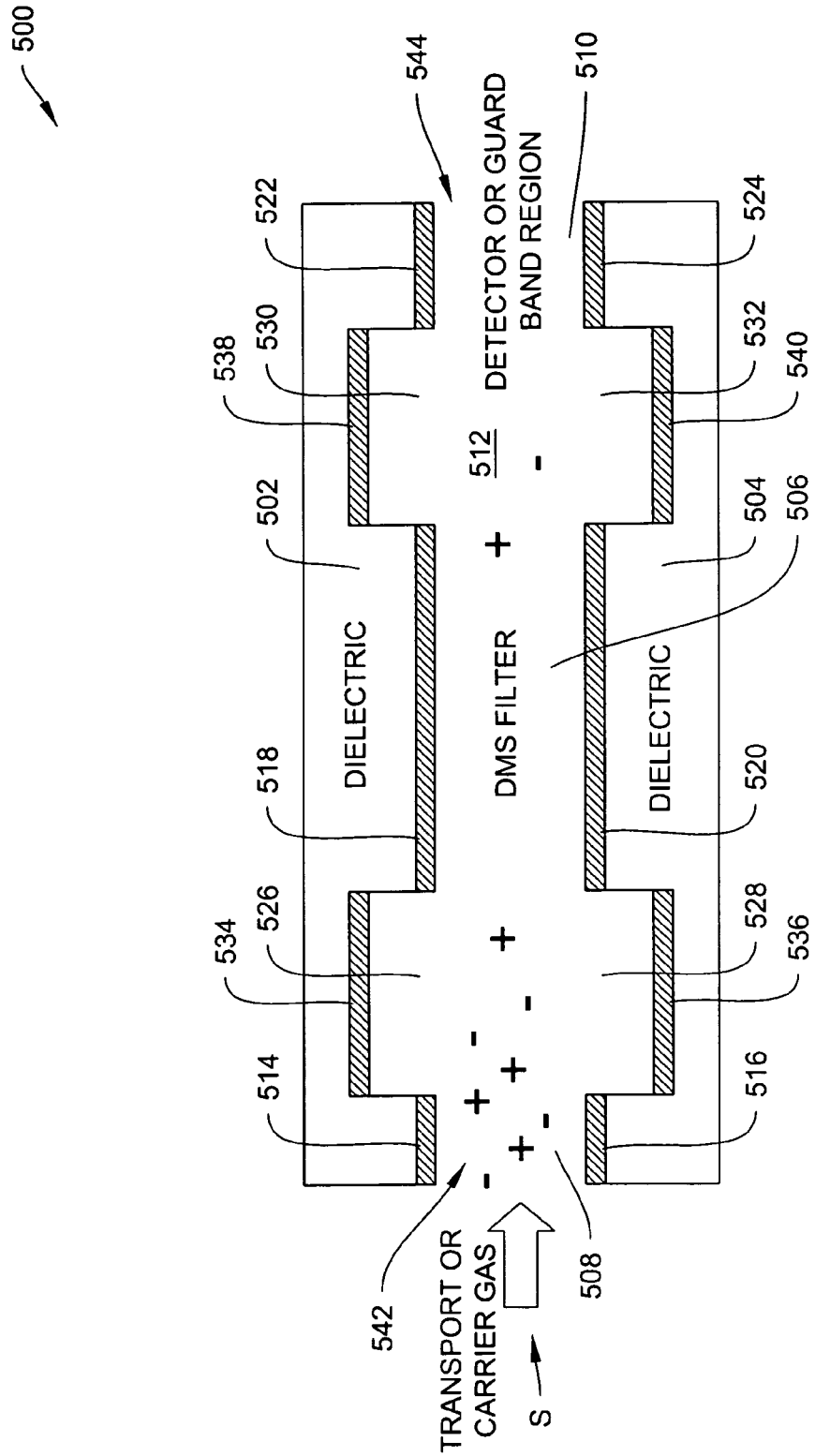
FIG. 5D is a conceptual diagram of DMS system where the dielectric material of the substrates adjacent to filter, ionization source, and detector are removed to reduce the adverse effects of charge build up according to an illustrative embodiment of the invention.

FIG. 5D is a diagram of DMS system 500 where the dielectric material of the substrates 502 and 504 adjacent to DMS filter 506, ionization region 508, and detector 510 are removed to reduce the adverse effects of charge build up along the flow path 512 according to an illustrative embodiment of the invention. The DMS system 500 includes ion source electrodes 514 and 516; DMS filter electrodes 518 and 520; DMS detector electrodes 522 and 524; substrate recesses 526, 528, 530, and 532; charge dissipation electrodes 534, 536, 538, and 540; sample inlet 542; and outlet 544. One or both of the detector electrodes 522 and 524 may function as guard band electrodes. Alternatively, the ionization region 508 may include one or more ion sources.

In operation, the DMS system 500 draws a sample S through the inlet 542 into the ionization region 508 where at least a portion of the sample S is ionized into either or both positive and negative ions. The ions then flow along the flow path 512 through the DMS filter 506 where selected ions are passed through to the detector 510. The recesses 526 and 528, which may be substantially proximate and/or adjacent to the entrance of the DMS filter 506, prevent the build up of charge along the flow path 512 preceding and/or upstream of the DMS filter 506. The charge dissipation electrodes 534 and 536 may be connected to a controller such as controller 40 of FIG. 1 and, depending on the bias voltage applied, counteract the effect of fringe fields immediately preceding the DMS filter 506. The recesses 530 and 532, which may be substantially proximate and/or adjacent to the exit of the DMS filter 506, prevent the build up of charge along the flow path 512 following and/or downstream of the DMS filter 506. The charge dissipation electrodes 538 and 540 may be connected to a controller such as the controller 40 of FIG. 1 and, depending on the bias voltage applied, counteract the effect of fringe fields immediately following the DMS filter 506. The charge dissipation electrodes 534, 536, 538, and 540 may include conducting and/or partially conducting materials. The charge dissipation electrodes 534, 536, 538, and 540 may be biased to conduct charge otherwise deposited by ions away from the flow path 512.

By removing the substrate and/or dielectric material proximate to the DMS filter 506, the DMS system 500 prevents or reduces the build up of charge along the flow path 512 before and/or after (upstream and/or downstream) the DMS filter 506. The charge dissipation electrodes 534, 536, 538, and 540 may also compensate for and/or counteract the fringe fields generated by the compensation voltage difference between DMS filter electrodes 518 and 520. For example, the dissipation electrodes 538 and 540 may cooperate to establish an electric field in a substantially opposite direction of the compensation voltage fringe field to cancel out, or reduce, the compensation voltage fringe field. A static and/or time varying voltage may be applied to the dissipation electrodes 538 and 540 to generate electric fields that compensate for and/or counteract the influence to the fringe fields. Each dissipation electrodes, such as dissipation electrodes 538 and 540, may be an array of electrodes, conducting elements, and/or partially conducting elements. Other electrodes, conductive surfaces, and/or materials may be employed to generate electric fields that counteract a compensation voltage fringe field. The charge dissipation electrodes 534, 536, 538, and 540 may also conduct or dissipate charge deposited by ions away from the flow path 512. By removing and/or minimizing charge build up along the flow path 512 and counteracting the fringe fields, the sensitivity, selectivity, repeatability, and/or stability of the DMS system 500 is improved with respect to other DMS systems such as DMS system 10.

Figure 5E:
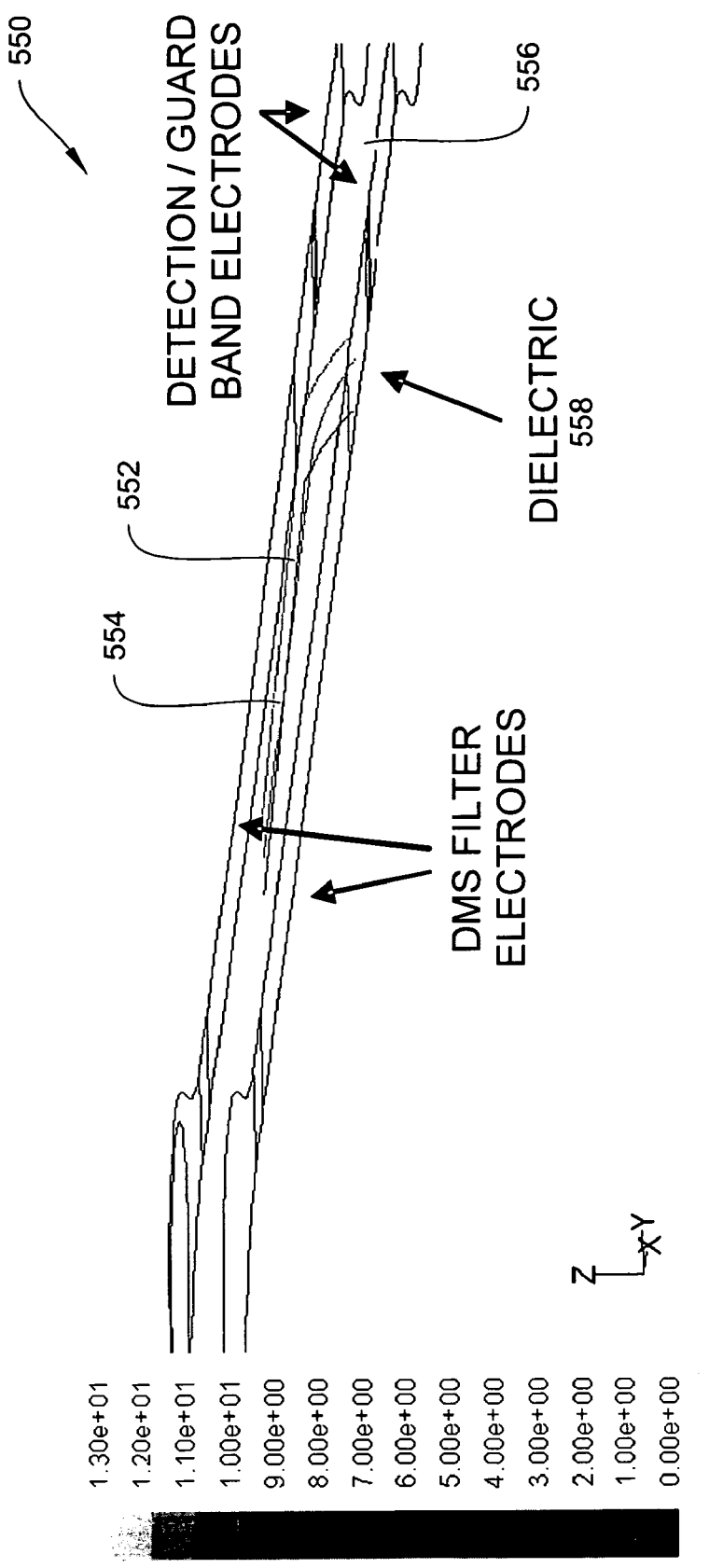
FIG. 5E shows a plot of the modeled trajectory of ions in a DMS system due to unbalanced asymmetric and compensation fields at the DMS filter exit where there is no charge build up on the surface of the dielectric substrate portion proximate to the filter exit.

FIG. 5E shows a plot 550 of the modeled trajectory of ions in a DMS system due to unbalanced asymmetric and compensation voltage fields at the DMS filter 554 exit where there is no charge build up on the surface of the dielectric substrate portion 558 proximate to the DMS filter 554 exit. Because the plot 550 of the modeled trajectory of ions excludes a charge build up on the substrate 558, the ions 552 are deflected to the dielectric substrate 558. Therefore, most ions do not reach and are not detected by the detector 556. The plot 550 of the modeled trajectory illustrates that the fringe field created by unbalanced asymmetric and compensation voltage fields can reduce the sensitivity of a DMS system.

Referring to FIG. 1, many of the ions that exit the DMS filter 24 defined by electrodes 20 and 22 are deflected to one of the exposed insulating substrates where they land and charge the surface at, for example, substrate portions 50 and 52. The ions are deflected to one of the substrates portions 50 and 52 due to the imbalance between the net ion motion produced by the asymmetric field (also known as the differential mobility RF field) and the compensation voltage field. The influence of the asymmetric field drops off much more rapidly beyond the electrodes 20 and 22 of the DMS filter 24 than the influence of the compensation voltage field. Away from the DMS filter electrodes 20 and 22, the asymmetric field intensity drops off such that the ions effectively do not experience a difference in mobility between the high field condition and the low field condition. In other words, the high field condition is not high enough to induce a change in the mobility of the ion relative to the low field condition.

Because the compensation voltage field is a DC field that is constantly applied to the ions exiting the DMS filter 24, the compensation voltage field produces a net deflection of the ion towards a particular substrate portion such as the substrate portions 50 and 52. As the charge builds up on the insulating surfaces and/or substrate portions 50 and 52, an electric field is developed which counters, counteracts, and/or compensates for the imbalance in the asymmetric (RF) fields and compensation voltage fields. The counter electric field reduces subsequent deflections of ions to the insulating substrate portions 50 and 52. However, there is a transient period associated with the buildup or decrease in charge on the substrates portions 50 and 52 which may cause transients in the ion intensity response of the DMS system 10. This transient effect may be undesirable for an ion based analyzer such as a quantitative analyzer because of the delay in achieving a stable detection signal. For example, during a scan over a range of compensation voltages, the cumulative delay at each measuring point may significantly reduce the speed and/or response time of a DMS system such as DMS system 10. The deflection of ions to a substrate may also occur in the region or substrate portions 54 and 56 prior to the DMS filter electrodes 20 and 22.

Figure 5F:
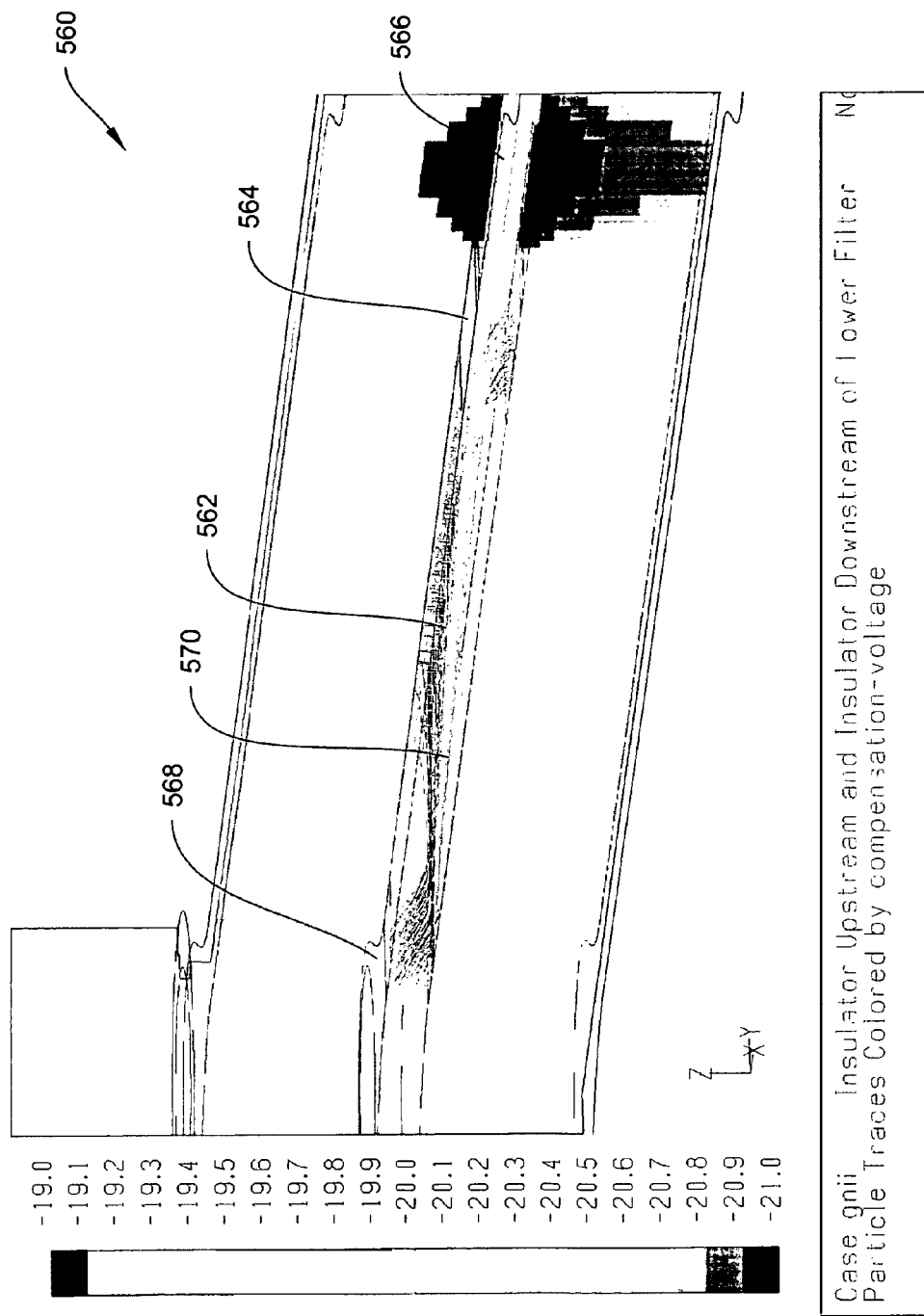
FIG. 5F shows a plot of the modeled trajectory of ions in a DMS system due to unbalanced asymmetric and compensation fields at the DMS filter entrance and exit where there is no charge build up on the surface of the upstream and downstream dielectric substrates proximate to the filter.

FIG. 5F shows a plot 560 of the modeled trajectory of ions in a DMS system due to unbalanced asymmetric and compensation voltage fields at the DMS filter 562 entrance and exit where there is no charge build up on the surface of the upstream dielectric substrate portion 568 and the downstream dielectric substrate portion 564. Because the plot 560 of the modeled trajectory of ions excludes a charge build up on the substrate portions 564 and 568, the ions 570 are deflected to the upstream and downstream dielectric substrates 564 and 568. Therefore, most ions do not reach and are not detected by the detector 566. The plot 560 of the modeled trajectory illustrates that the fringe field created by unbalanced asymmetric and compensation voltage fields can significant reduce the sensitivity of a DMS system.

Figure 5G:
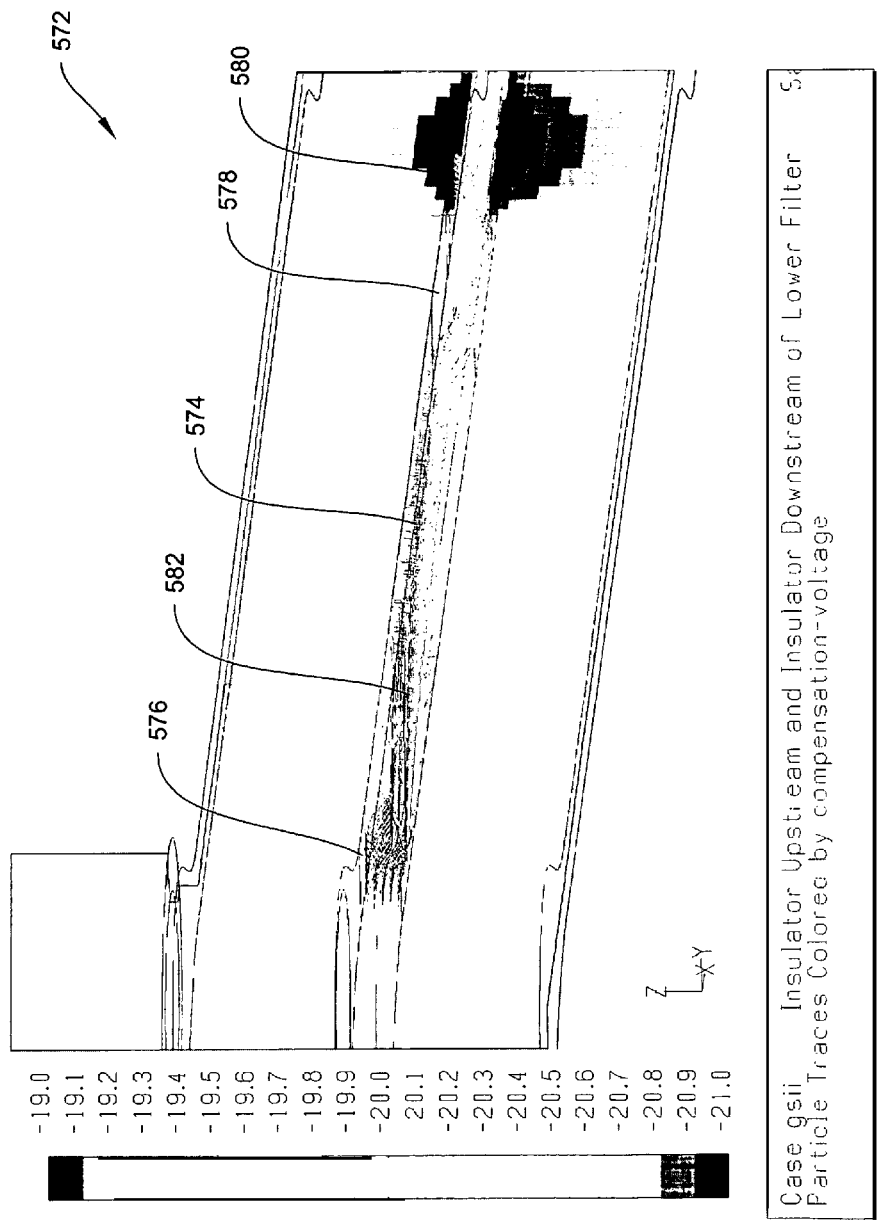
FIG. 5G shows a plot of the modeled trajectory of ions in a DMS system due to unbalanced asymmetric and compensation fields at the DMS filter entrance and exit where there is charge build up on the surface of the upstream and downstream dielectric substrates proximate to the filter.

FIG. 5G shows a plot 572 of the modeled trajectory of ions in a DMS system due to unbalanced asymmetric and compensation fields at the DMS filter entrance and exit where there is charge build up on the surface of the upstream dielectric substrate 576 and downstream dielectric substrate 578 proximate to the filter 574. Because the plot 572 of the model trajectory of ions 582 includes a charge build up on the substrate portions 576 and 578, the ions 582 are deflected away from the upstream and downstream dielectric substrates 576 and 578. Therefore, most ions do reach and are detected by the detector 580. The plot 572 of the modeled trajectory illustrates that the charge build up at dielectric substrate portions 576 and 578 counteracts the fringe field created by unbalanced asymmetric and compensation voltage fields, allowing the ions 582 to be detected at the detector 580 after a transient and/or stabilization period.

As described above, the charge buildup occurs on the dielectric surface up to a saturated steady state condition. The buildup of charge acts to counter the effect of the DMS filter fields extending beyond the filter and allows the ions to reach the detector and/or guard band electrodes.

Thus, in certain embodiments, having the charge buildup on portions of the substrate in a DMS system is beneficial. However, the charge buildup appears dependent on many parameters, such as, without limitation, environmental conditions which affect the surface conductivity of the dielectric, the amount of charge build up, and the type of sample flowing through the device, among other conditions. Referring to FIG. 5D, the recesses 526, 528, 530, and 532 along with the charge dissipation electrodes 534, 536, 538, and 540 enable a DMS system such as DMS system 500 to be less sensitive to these parameters. However, there are other features and/or designs capable of reducing the effects of the external and/or fringe DMS filter fields that allow more efficient ion transport through the DMS filter in a more controlled manner.

Figure 6A:
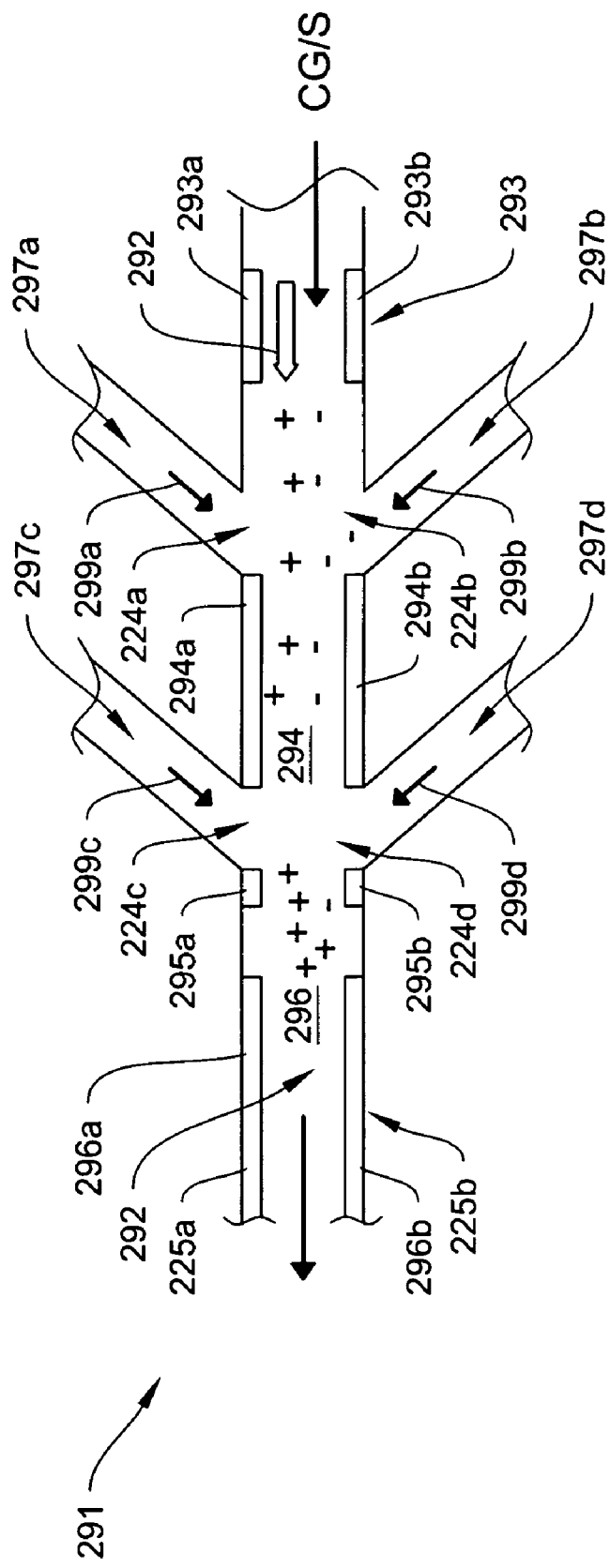
FIG. 6A shows a system having multiple flow paths that reduce charge build-up and enable ion concentration according to an illustrative embodiment of the invention.

FIG. 6A shows a DMS system 291 having multiple flow paths that reduce charge build-up and enable ion concentration according to an illustrative embodiment of the invention. The DMS system 291 includes recesses 224a-224d that are provided to reduce, or in some instances minimize, the likelihood of charge buildup interfering with the analytical flow. More specifically, analytical device 291 receives a flow, such as a carrier gas CG with sample S, into flow path 292 and into ionizer 293, the latter illustrated having electrodes 293a and 293b. Ions ++, -- are generated and flow into DMS ion filter 294 between filter electrodes 294a and 294b. A selected ion species ++ is passed through filter 294 according to the filter field, flowing past guard electrodes 295a and 295b and into detector 296 to be detected by a detector electrode 296a or 296b, according to polarity.

Recesses 224a-224d are respectively defined by the mouth of a respective flow path 297a-297d joining flow path 292. Flow paths 297a-297d permit a gas inflow or outflow. In a further embodiment, the respective flow paths 297a-297d enable introduction of containment gas flows 299a-299d. For example, flow 299d from path 297d flows into flow path 292. The flow 299d joins the ion flow ++, -- at an angle which enables the flow 299d to drive the ion flow ++, -- toward the center of flow path 292. Preferably flow 299d cooperates with containment flows 299a-299c to achieve ion concentration toward the center of flow path 292. Thus, in addition to controlling charge build-up, in this embodiment, an ion-concentrating function is provided to concentrate the ion flow and to further improve system performance.

Figure 6B:
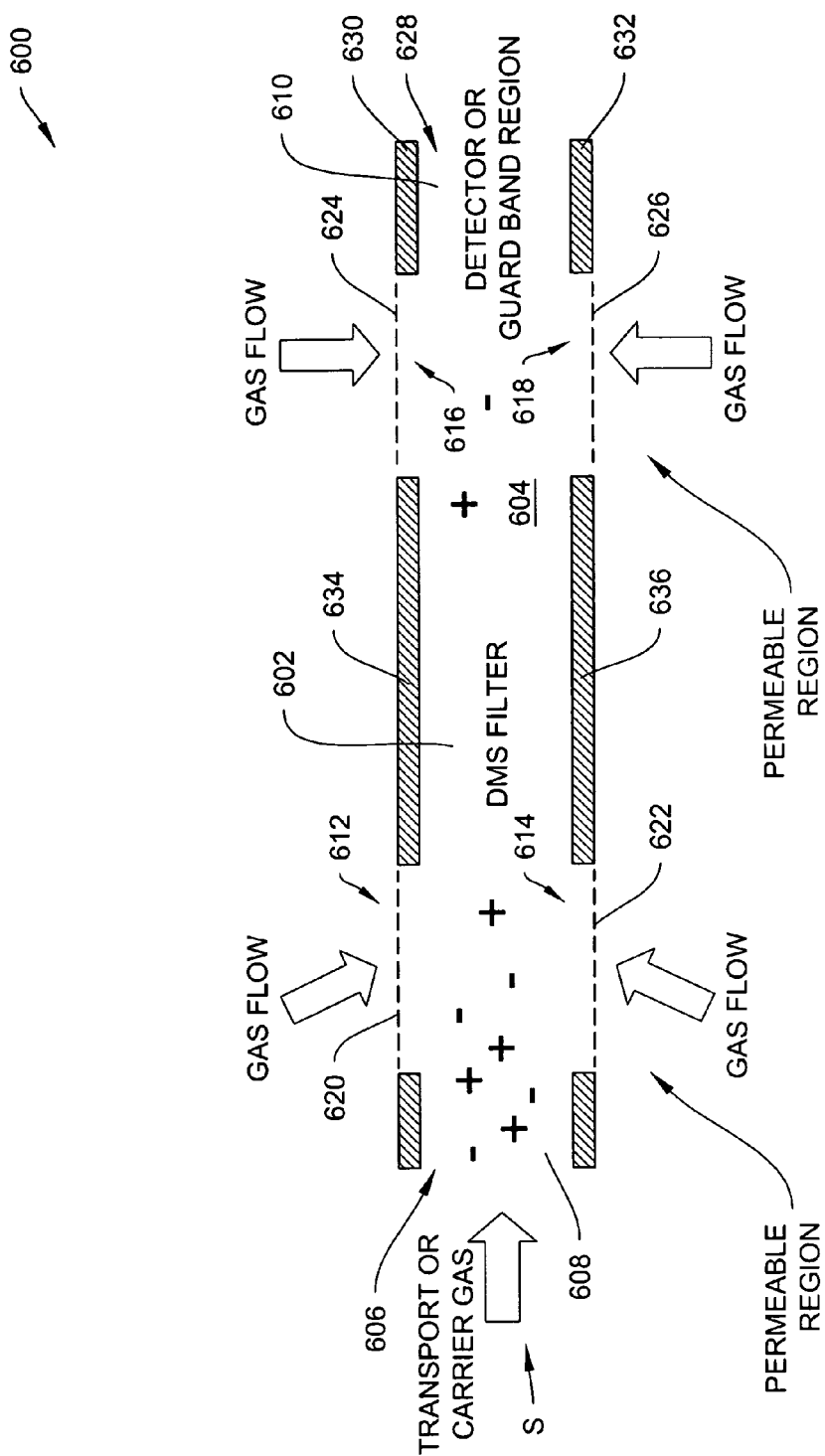
FIG. 6B is a conceptual diagram of a DMS system including permeable substrate regions adjacent to the DMS filter that enable gas flow for confining and/or focusing ion in the DMS flow channel according to an illustrative embodiment of the invention.

FIG. 6B is a conceptual diagram of a DMS system 600 including permeable substrate materials adjacent to the DMS filter 602 that enable gas flow from at least one external channel for confining and/or focusing ions in the DMS flow channel 604 according to an illustrative embodiment of the invention. The DMS system 600 includes sample S inlet 606, ionization region 608, detector 610, gas inlets 612, 614, 616, and 618, gas inlet separators 620, 622, 624, and 626, and outlet 628. The detector 610 includes detector electrodes 630 and 632. The DMS filter 602 includes filter electrodes 634 and 636. The gas inlet separators 620, 622, 624, and 626 may include a permeable and/or porous material that enables one or more gases to flow to or from the flow path 604. The permeable and/or porous material may include a mesh of conductive or non-conductive material. For example, without limitation, a metal mesh could be used in some areas while a fritted/porous non-metallic materials can be used in others. The separators 620, 622, 624, and 626 may include conductive material to improve charge dissipation in the flow path 604.

In operation, the DMS system 600 draws a sample S into the ionization region 608 via the inlet 606. At least a portion of the sample S is ionized into either or both positive and negative ions. Gas flow within the flow path 604 transports the ions to the DMS filter 602. Additionally, gas flow may be introduced into the flow path 604 via inlets 612 and 614 to direct the ions substantially toward the center of the flow path 604 and away from any surface where charge could be deposited by the ions. One or both of the gas inlets 612 and 614 may include separators 620 and 622. In one embodiment, the separators 620 and 622 are gas permeable and assist in defining the flow path 604. The separators may also act as particle filters to reduce the introduction of certain impurities into the flow path 604 or to enable a pressure and/or flow difference in the flow path 604 with respect to an environment external to the flow path 604.

The DMS filter 602 allows selected ions to pass through to the detector 610 for detection. Gas inlets 616 and 618, which are positioned substantially adjacent to and downstream of the DMS filter 602, may introduce gas flow into the flow path 604 to direct the ions substantially toward the center of the flow path 604 and away from any surface where charge could be deposited by the ions exiting the DMS filter 602. One or both of the gas inlets 616 and 618 may include separators 624 and 626. The separators 624 and 626 may include materials that are either or both gas permeable and conductive.

Figure 6C:
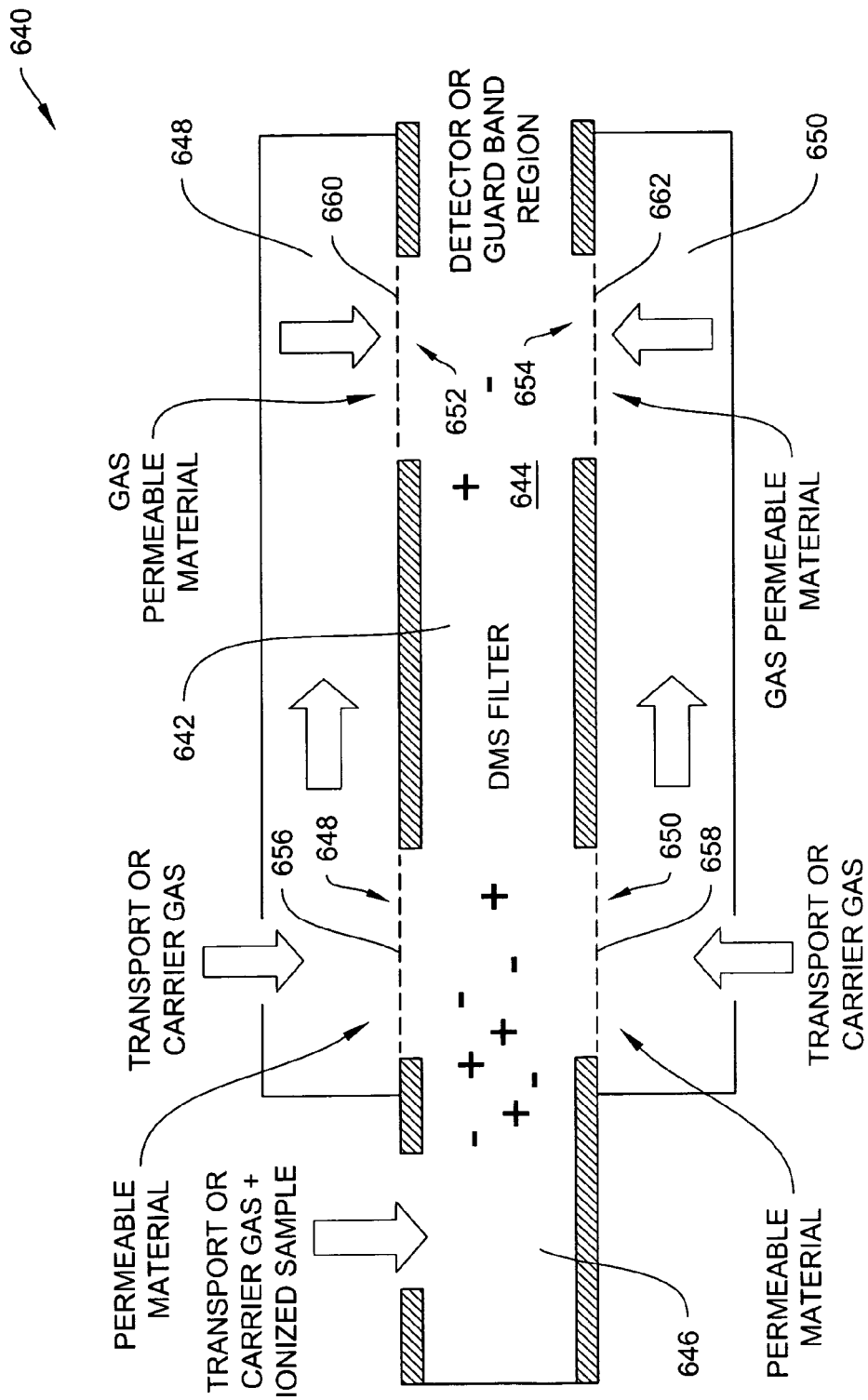
FIG. 6C is a conceptual diagram of a DMS system including permeable substrate materials adjacent to the DMS filter that enable gas flow from an external channel for confining and/or focusing ion in the DMS flow channel according to an illustrative embodiment of the invention.

FIG. 6C is a conceptual diagram of a DMS system 640 including permeable substrate regions and/or materials adjacent to the DMS filter 642 that enable gas flow for confining and/or focusing ion in the DMS flow path 644 according to an illustrative embodiment of the invention. The DMS system 640 includes many of the features of the DMS system 600 and operates in a similar manner. The DMS system 640, however, also includes an inlet region 646 and carrier gas channels 648 and 650. The inlet region 646 may function as a pre-separator for the DMS system 640. The inlet region 646 may include, without limitation, an ion trap, gate, grid, ionization source, gas chromatograph column, an ion mobility based analyzer, and like pre-separator components. The DMS system also includes gas inlets 648, 650, 652, and 654. The gas inlet separators 656, 658, 660, and 662 are included at the gas inlets 648, 650, 652, and 654, respectively.

In operation, the DMS system 640 operates in a similar manner as the DMS system 600. Additionally, the carrier gas channels 648 and 650 deliver gas to the flow path 644 via gas inlets 648, 650, 652, and 654. In one embodiment, the carrier gas channels 648 and 650 may be substantially planar. In another embodiment the carrier gas channels 648 and 650 are combined into one channel that substantially surrounds the flow path 644. One advantage of the DMS systems 600 and 604 is that ions are focused towards the center of the flow path in each system which results in a tighter initial distribution of the ions in the center of the flow path and/or drift tube, producing more narrow DMS spectral peaks.

Charge dissipation approaches and controls may be beneficial for single polarity ion sources such as electrospray, corona discharge, plasma, and sources with high ion fluxes. DMS systems work favorably with, and can benefit from control of, charged surfaces along the flow path.

In one illustrative embodiment, a controller such as controller 40 (See FIG. 1) regulates and/or controls the compensation voltage (Vcomp) applied to the filter electrode 20 and/or 22 to regulate and or control the compensation field generated by the ion filter 24 in the flow path 11 of the DMS system 10.

Because the nature of the Vcomp scan determines changes in the charge state of the DMS system 10, part of the ion filter 24 operating time can be used to control the imbalance of charges. If the DMS system 10 flow path 11 becomes highly charged, intensities can be affected by a factor of 2 or more. Symmetrical Vcomp scans or correctively-offset Vcomp scans can be used to keep charging in balance. For example, a symmetric and/or balanced Vcomp scan may be centered at 0 volts with equals sweep voltages ranges above and below 0 volts, e.g., −1.5 V to +1.5 V. By applying a symmetric Vcomp scan to the filter electrode 20, the controller 40 can neutralize charging and/or charge build up in the flow path 11. While symmetric Vcomp scans may be advantageously used for bi-polar ions sources such as $^{63}$Ni and photo-ionization, this approach may be less effective for monopolar ion sources like some corona sources.

Figure 6D:
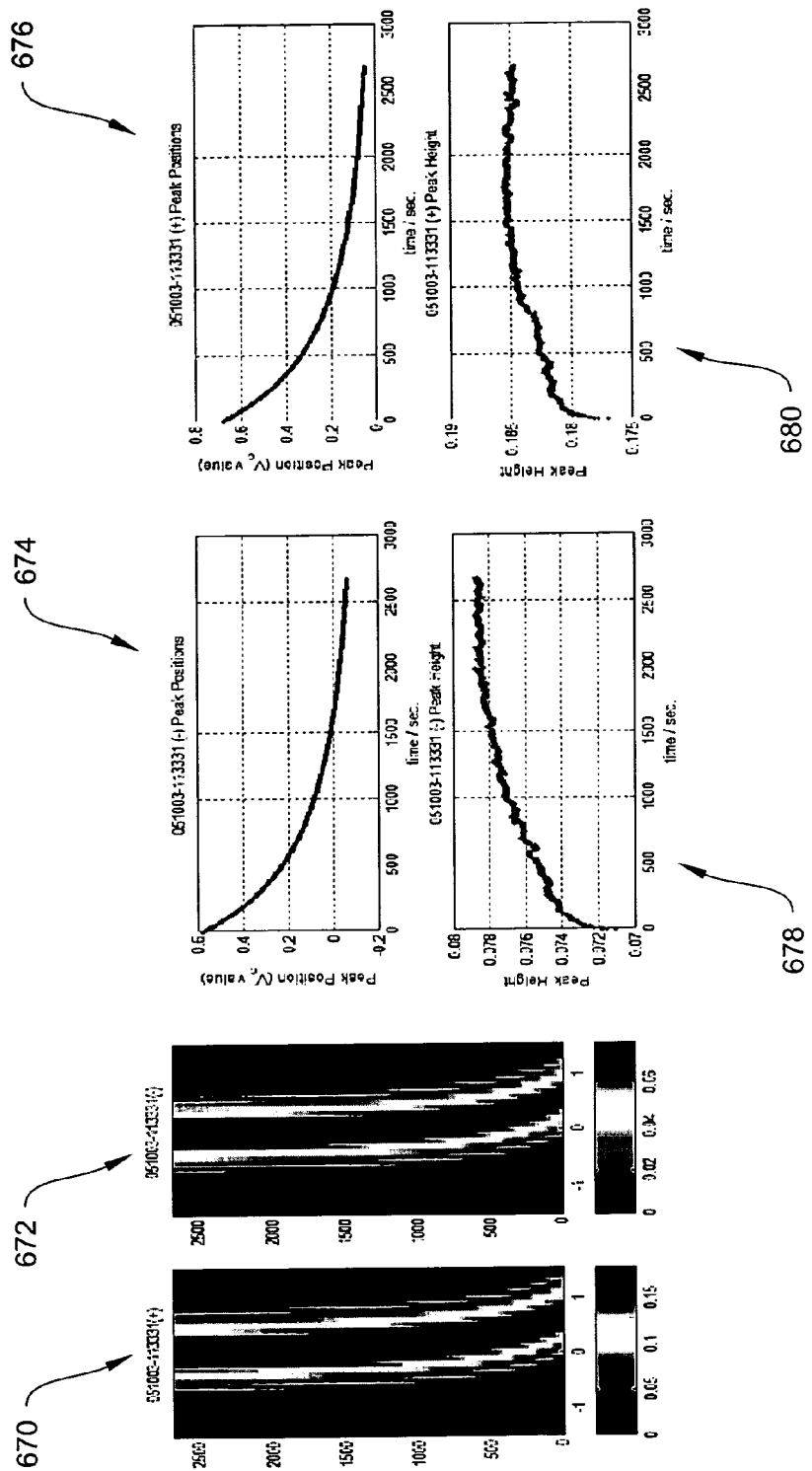
FIG. 6D shows a positive plot and negative plot of the ion intensity spectra of a DMS system for compensation voltage versus time over a period of 2500 seconds according to an illustrative embodiment of the invention.

FIG. 6D shows the positive plot 670 and negative plot 672 of the ion intensity spectra of a DMS system for Vcomp versus time over a period of 2500 seconds. FIG. 6D illustrates the control of charging by a symmetric Vcomp scan of −1.5 V to +1.5 V which may be implemented as an intermittent operation either in software or in firmware within the controller 40. The plots 674 and 676 show Vcomp versus time (seconds) for the positive and negative peak positions respectively. The plots 678 and 680 show the positive and negative ion intensity peaks height versus time (seconds) respectively. A comparison of the plots 674 and 676 illustrate that symmetric Vcomp scan may reduce the charge magnitude to less than about 0.2 volts in a DMS system such as DMS system 10. FIG. 6D also shows that the ion intensities are also stabilized by positioning the zero-peak approximately near 0 volts.

In one embodiment, the DMS system 10 operates using a desired Vcomp bias range for a period of time to detect certain ion species. Periodically, intermittently, and/or at certain intervals, the DMS system 10 operates using a symmetric Vcomp scan to reduce the charging effect in the DMS system 10. The intermittent operation of the Vcomp scan prevents charge buildup by taking advantage of the slow rate of charge buildup in the flow path 11. For example, it may takes 20 minutes or more for charge to build up, so the Vcomp scan correction can be interleaved with signal acquisition and/or filtering/dectection of ion species. The symmetric Vcomp scan may include a range of less than about −1V to +1V, about −1.5V to +1.5V, about −2V to +2V, about −3V to +3V, −5V to +5V, −10V to +10V, and about −15V to +15V.

In another embodiment, the controller 40 employs hardware, firmware, software, or a combination of hardware, firmware, and software to maintain a low level of charge in the flow path 11 of the DMS system 10. The controller 40 may also correct for other charging effects by identifying Vcomp correction and reporting a Vcomp correction with the detected spectra and/or data outputted from the controller 40. In another embodiment, the DMS system 10 designates a variable user selectable and/or automatically assigned Vcomp window for certain ion species filtering and/or detection.

Because the Vcomp encountered by ions in the flow path 11 may be different that the Vcomp applied by the controller 40 to the filter electrode 20 be approximately the value of the zero-peak position, the controller 40 may periodically measure the zero-peak position during DMS system 10 operations. For example, the zero-peak position value and/or offset may be measured every 30 seconds. In one embodiment, the controller 40 records the measured offset and provides this information along other values such a Vrf, Vcomp, and ion intensity, among other values, as an output of the system 10. In another embodiment, the controller 40 uses the measured offsets to interpolate the actual Vcomp and to report the estimated ion intensity at the request Vcomp value.

In another embodiment, the controller 40 controls the zero-peak position such that the position is substantially near zero. The DMS system may also employ shield flow via one of more flow path inlets to focus the ion flow in the flow path. In certain instances, the ion intensity may be increased by about 30% and the ion intensity peak widths reduced by about 15%.

FIG. 6E is a plot 682 of Vcomp versus Vrf (for negative Vcomps) that illustrates how the charging affects RF-on and RF-off peak positions nearly identically. The plot 682 shows that the zero peak offset 684, which is approximately 1.27 volts, can represent the offset in all RF-scan peak positions.

The difference in zero-peak positive positions may be similar. By accounting for the zero-peak offset, a DMS system can eliminate or reduce the certain electronic effects was cause the offset. The offset causes the detected ion intensity peaks to be shifted. If the offset in a various DMS systems are different, are variable, and/or changing, the reliability, accuracy, and sensitivity of the DMS systems may be reduced. In one embodiment, the DMS system 10 employs controller 40 to compensate and/or account for the zero-peak offset effect. For example, because the RF-on and RF-off peak positions shift correspondingly, the controller 40 may subtract the RF-off peak position to reduce the peak position variability to less than about 0.1 V, 0.075 V, or 0.05 V. The subtraction approach may eliminate or reduce the effect of charging on peak positions. The controller 40 may employ hardware, firmware, and/or software to compensate for the offset.

In one illustrative embodiment, a charge field is established along the flow path. In another illustrative embodiment, filter and detector electrodes are isolated from each other to prevent interfering with ion detection. This separation can be achieved by insulating the electrodes, such as by building on insulated substrates.

At times, it may be required to reduce charge buildup on the flow path surfaces (e.g., at least a portion of the surface 110a of substrate 110 of FIG. 3B). The invention provides the option of charge dissipation without interfering with action of the filter and detector electrodes. In one exemplary embodiment, electrospray ionization in DMS is employed while reducing the effect of surface charge buildup on the exposed surfaces of the flow path, which includes exposed surfaces in between the electrodes. The charge-dissipative (e.g., partially conducting) control material of the invention forms a charge dissipation path to reduce charge buildup. The ionized electrospray flows through the DMS filter with regularity. Thus, the control material of the invention is used to form a charge-dissipative surface to replace or augment or cover or cooperate with the filter electrodes and the other surfaces of the flow path.

Figure 7A:
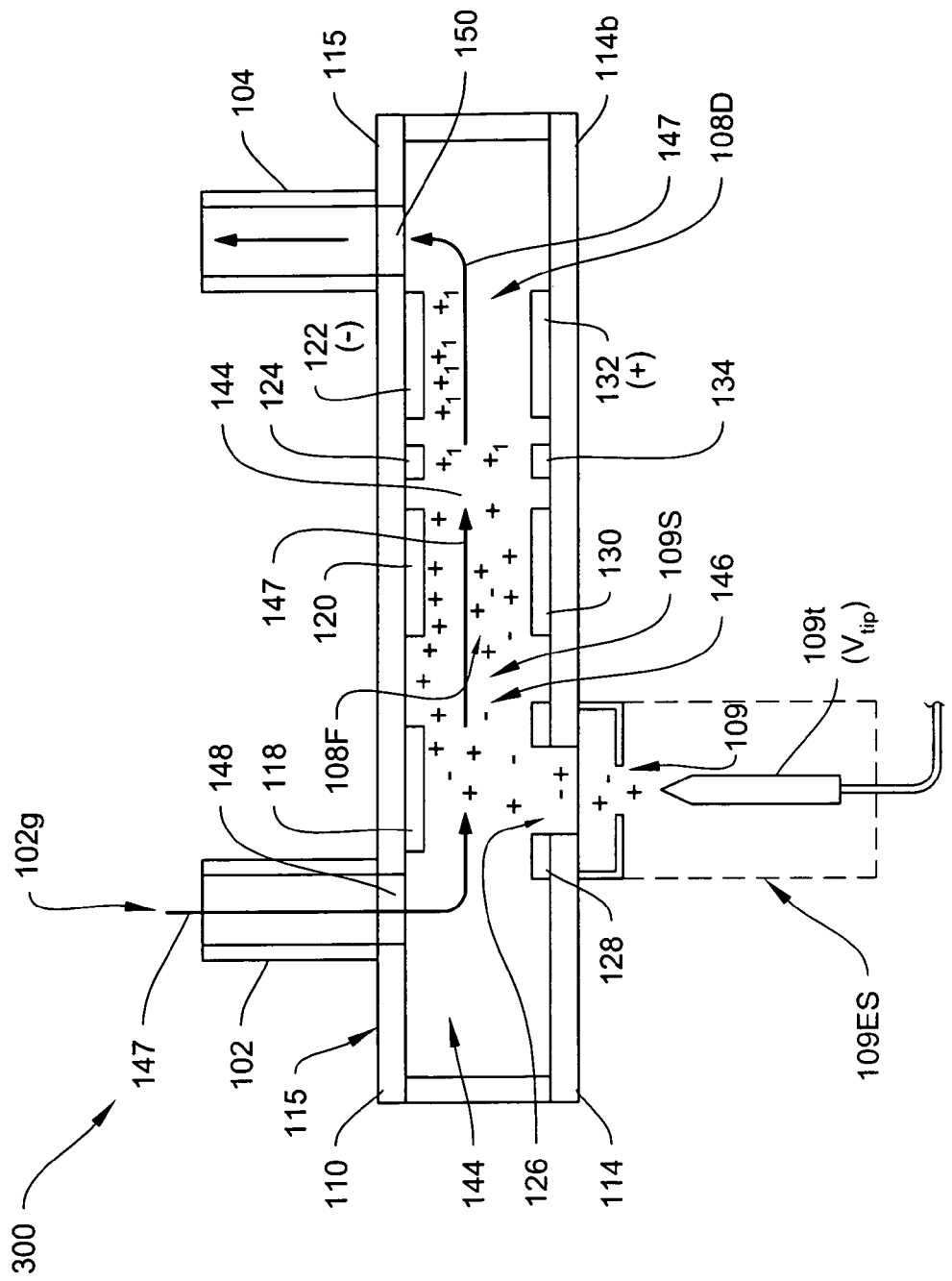
FIG. 7A shows a side schematic view of an alternative DMS chip according to an illustrative embodiment of the invention.

The embodiment of FIG. 3E can be modified according to the invention, as shown in FIG. 7A, to utilize an electrospray head 109ES attached to chip 300, such as at substrate 114. In an ESI-filter assembly 300, carrier gas 102g is introduced via inlet 102 and the sample to be filtered is ionized and introduced via the electrospray head 109ES as ionized sample stream 109s. The electrospray tip 109t is held at a high electrical potential (Vtip) and charges the atomized ionized spray molecules (positive or negative, but shown as +, +, +), which are attracted by oppositely-charged attractor electrode 118 as they flow through ionization access port 126 into flow path 144. The ionized sample 109s is conveyed along the flow path and into in the analytical gap between filter electrodes 120 and 130 of ion filter 108F.

In this illustration, these ions (+, +, +) are subjected to the compensated asymmetric RF field of filter 108F. The species of ions that are returned toward the center of the flow by practice of embodiments of the invention will pass as species $+_1$ into the detector. If these are positively-charged ions, then a positive bias on detector electrode 132 steers the ions toward negatively-biased detector electrode 122 with which these positive ions make contact and where they deposit their charges. (Negatively charged ions can be detected in a similar manner, with opposite polarity biasing.)

The ion species detection and the intensity of detection are correlated with the parameters of the filter environment, which is evaluated against a library of information for identifying detected species. Finally, the ions $+_1$ having lost their charges return to being neutral molecules and they and the rest of the gas flow are carried out of the detector region via outlet 104.

Figure 7B:
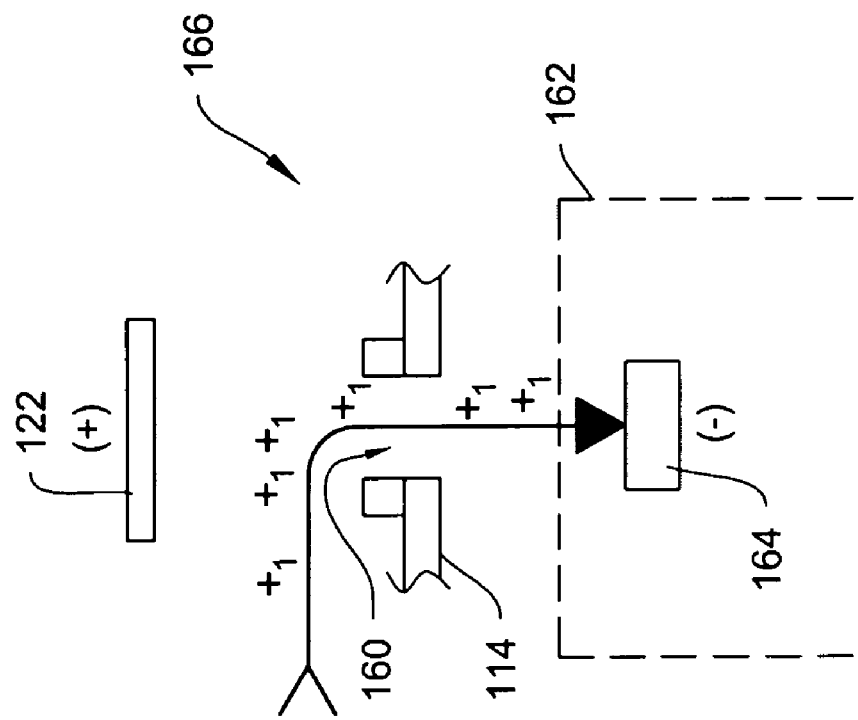
FIG. 7B shows an alternative detector arrangement according to an illustrative embodiment of the invention.

FIG. 7B shows an alternative arrangement, where the separated ions $+_1$, $+_1$, $+_1$ are outputted for external use. In such embodiment, detector electrode 122 is opposite an orifice 160 in substrate 114 and the biased electrode 122 (e.g., positively biased) steers ions $+_1$, $+_1$, $+_1$ toward the orifice where they flow out of the flow channel. In one embodiment, this enables the ions to be delivered to the input of a mass spectrometer 162, which may be assisted by an attraction electrode 164 (in this example negatively biased to attract ions $+_1$, $+_1$, $+_1$). This arrangement may further include an electrode ring 166 which cooperates with orifice 160 for the passage of ions $+_1$, $+_1$, $+_1$ out of the flow channel, while also being capable of being biased to attract a portion of the ion flow $+_1$, $+_1$, $+_1$. Now, feedback and control data may be obtained at electrode ring 166 as a detector, for the operation of the filter system of the invention, while also enabling a desired ion output.

As can be seen from the above discussion, an electrospray head provides a highly ionized sample flow into the flow path. In some illustrative embodiments, the invention combines an electrospray with previously discussed partially-conductive aspects, such as the earlier described partially-conductive layers 211 and 215. These charge-dissipative surfaces carry away the "static" charge build-up and further enable ion analysis in an electrospray-DMS system of the invention.

Control of Ion Motion

In several illustrative embodiments of the invention, controlled voltages are applied to control surfaces and/or control electrodes (which may be formed as arrays) to affect and control local ion behavior, density, or concentration. This may also include control or influencing of ion velocity and/or direction of ion travel, even by species.

Illustratively, in the device 200 of FIG. 4A which includes electrode arrays 211U and 215D facing each other over the flow path 201 and ions flowing through the analytical gap G in between these arrays, several aspects of species-specific ion motion control may be implemented. The ion motion control may include, for example, application of a longitudinal propulsion field for propulsion of ions along the flow path, generation of the DMS RF filter field to affect differential transverse ion motion in the filter, and/or compensation of the DMS filter field to select ion species for passing through the filter field.

Generation of the DMS RF filter field and compensation of the field have been set forth in U.S. Pat. No. 6,459,823, incorporated herein by reference. Electric field propulsion of ions along a DMS flow path has been set forth in U.S. Pat. No. 6,512,224, also incorporated herein by reference. The electrodes in electrode arrays 211U and 215D can be driven to achieve such ion filtering, propulsion and the like.

Figure 8A:
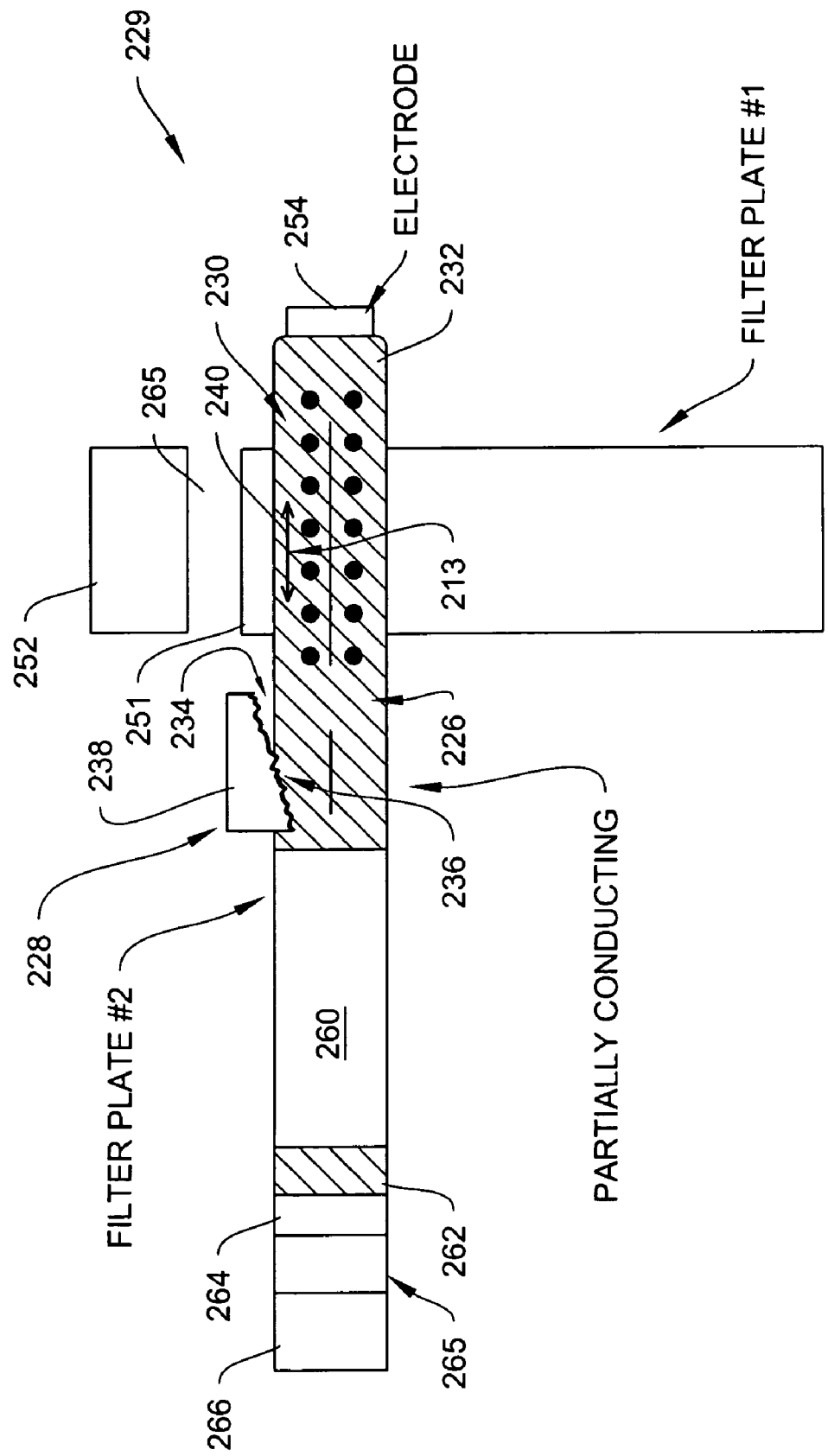
FIGS. 8A-8B are schematic views of alternative illustrative embodiments of the invention having multiple flow paths.

Electrodes or combinations of electrodes of the electrode arrays may be driven to steer, focus, confine or trap the ion flow, as well as to reduce fringing fields or to achieve other field affects. An ion steering illustration is provided in the layout of FIG. 8A, where a DMS filter 228 is formed by facing surfaces (e.g., substrates) 226 and 234 of chip assembly 229. In FIG. 8A, surface 226 and associated components are shown and surface 234 is only partially shown.

Electrode array 230 is formed on partially-conductive material layer 232 associated with surface 226; array 230 operates in cooperation with an array 236 formed on opposed partially-conductive material layer 238 on filter surface 234.

Arrays 230 and 236 are driven to perform ion control functions of the invention as applied along flow path 240. In addition, or alternatively, layers 232 and 238 can include a resistive coating over which a voltage is dropped to create a steering field for steering ions accordingly. Ions flow along flow path 240 into filter 228 and are filtered according to the variously described approaches of the invention.

In one illustrative embodiment, ion species output from an upstream filter (e.g., filter 213 of FIG. 4E) pass across flow path 240, across a guard electrode 251, to reach detector 252 for detection and identification of passed ion species.

However, in a further embodiment, a steering electrode 254 at one end of flow path 240 has a potential applied to steer and propel ions of a polarity (e.g., positive) outputted from filter 213; these ions are carried along flow path 240 so as to be subjected to arrays 230 and 236 of filter 228. The other ions (e.g., negative) are attracted toward electrode 254 and are not flowed to filter 228 at that time.

Figure 8B:
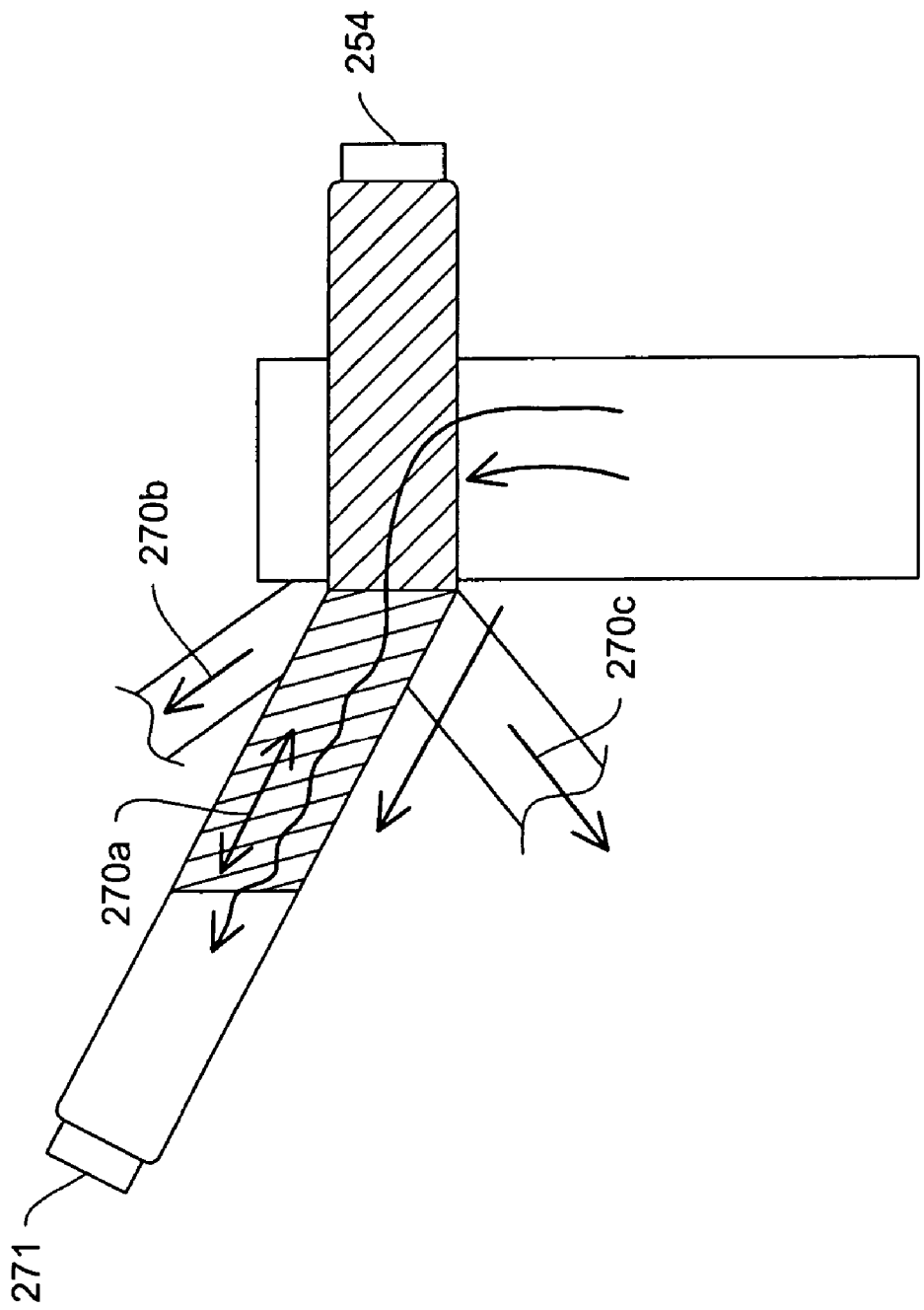

In the embodiment of FIGS. 8A-8B, arrays 230 and 236 enable performance of a number of local functions that impact the local ion flow in the flow path 240 defined between the facing substrates 226 and 234. As well, an additional filter 260 may be added to flow path 240 to enable further sample/species filtering, and it may include further partially-conductive layers 262 to control charge buildup.

A detector electrode 266 can be provided that detects the passed ions. The guard electrode 264 is isolated (such as by insulated land 265) from the detector electrode 266 so as to prevent filter signals from interfering with the detection signal. A similar arrangement is applied to guard electrode 251.

In a further embodiment of the invention, as shown in FIG. 8B, ions that arrive from filter 213 and are steered by electrode 254 may obtain an angular vector that can be anticipated and accommodated by having one or several angled filter path(s) 270a-270c. Appropriately deflected ions flow along flow paths 270a-270c for further processing. Additional collection or attraction electrodes, e.g., electrode 271, may also be provided to further assist ion separation and/or analysis. Thus, ion species having a first characteristic may be deflected into path 270a, while ion species having a second characteristic may be deflected into path 270b, and yet another into path 270c, which may reflect ion mobility, weight, mass, or other characteristics.

Figure 9B:
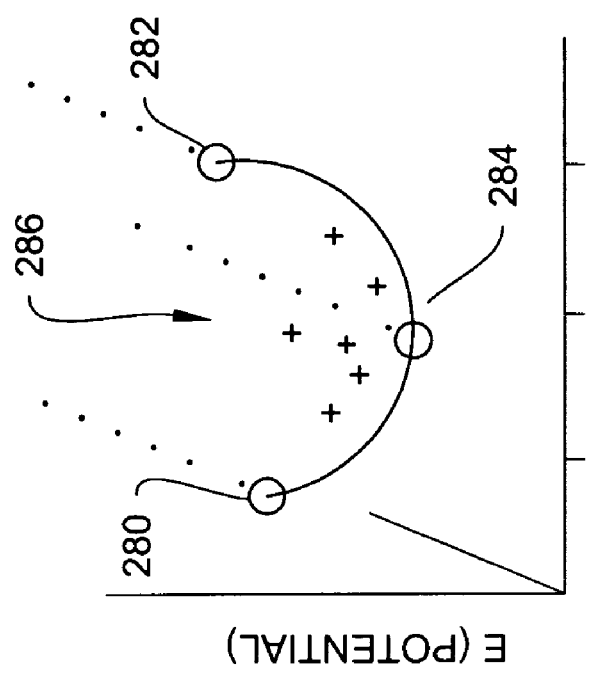
Figure 9A:
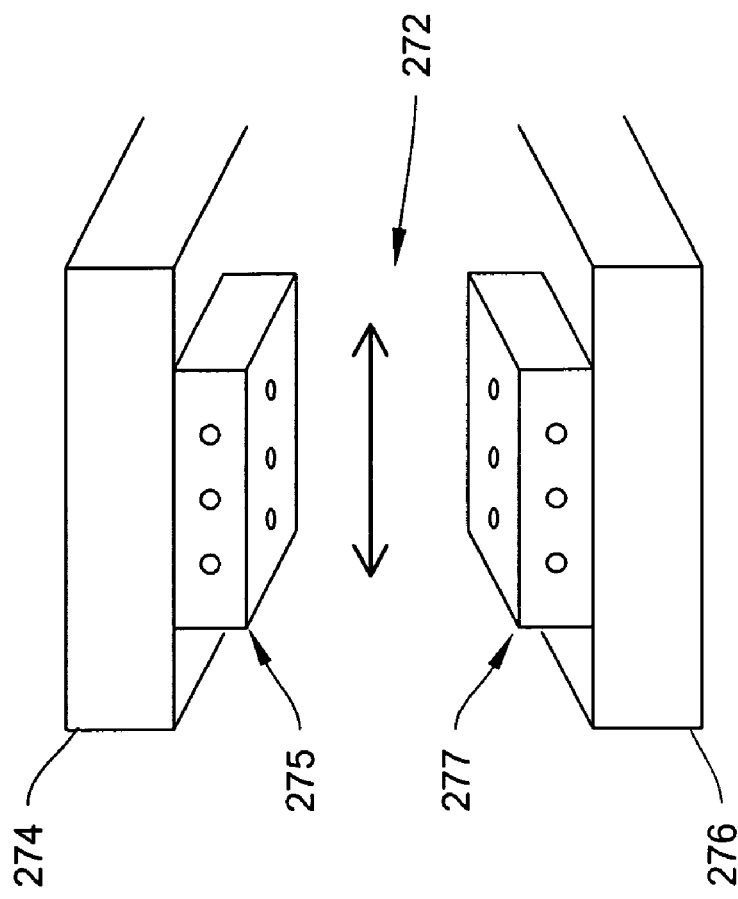

FIG. 9A shows a filter 272 having upper and lower electrode arrays 275 and 277 formed on partially-conductive material layers 274 and 276, respectively, according to another illustrative embodiment of the invention. By appropriately driving various ones of these electrodes, ions of a given polarity can be steered or collected at various locations within the flow path.

Ion control is further described with respect to FIG. 9B, where the effect of having different potentials (varied over time) applied to parallel electrode columns 280, 282 and 284 is to create a potential "well" or "trough" 286 in which ions of a given mobility aspect can collect, producing a condensing or focusing effect. This can be explained with respect to polarity, for example, where electrodes 280 and 284 are positive and electrode 282 is less positive, and therefore positive ions (ions +, +, +, + in FIG. 9B) tend to collect in the trough 286.

Figure 10B:
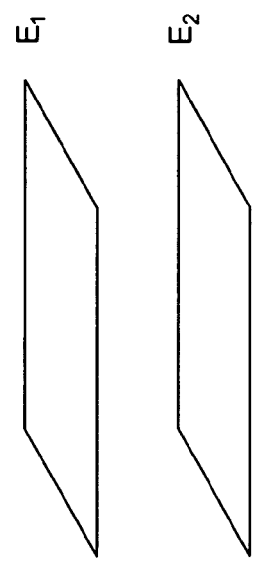
FIGS. 10B-10E show concentrator electrodes and drive signals according to illustrative embodiments of the invention.
Figure 10A:
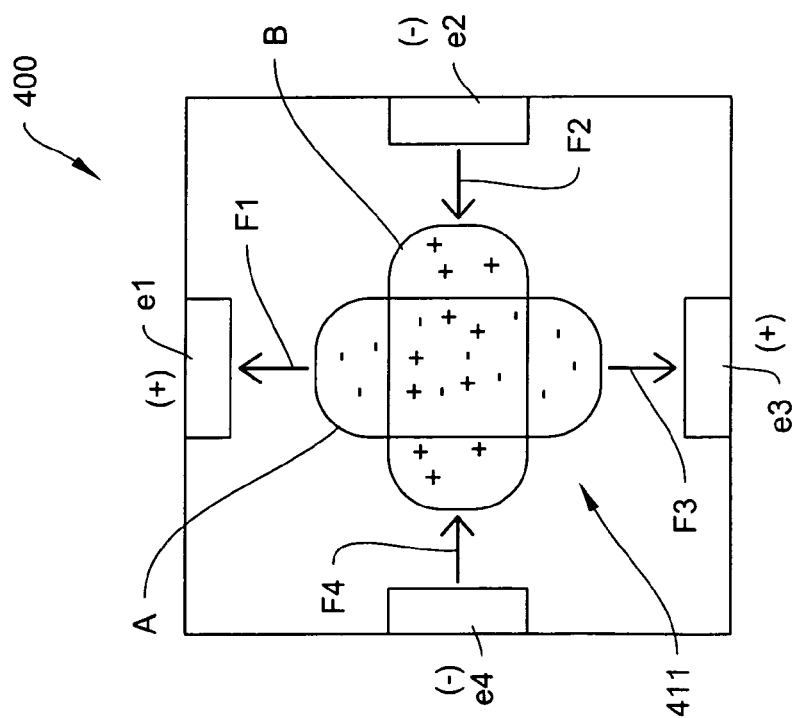
FIG. 10A shows concentrator electrodes according to an illustrative embodiment of the invention.
Figure 10C:
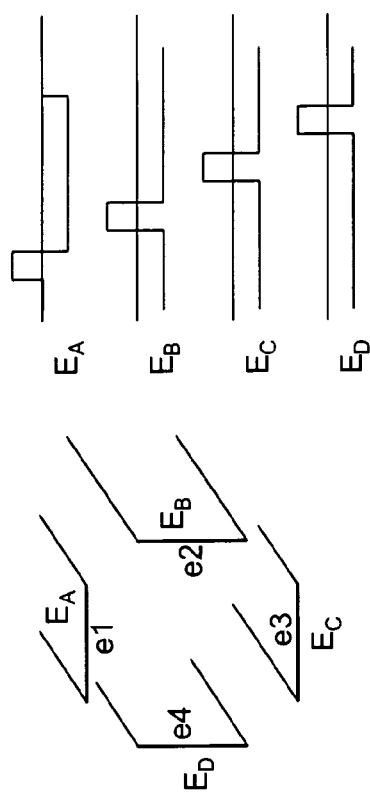
Figure 10E:
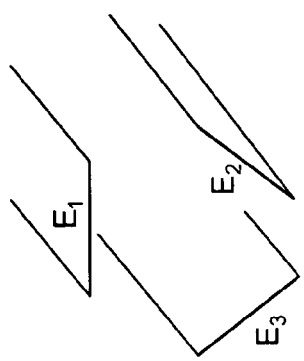
Figure 10D:
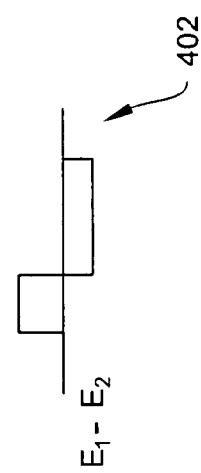

FIG. 10A shows a plurality of ions ++, -- near the center of flow path 411 in an ion-controlling embodiment 400 of the invention. In an illustrative embodiment, electrodes e1 and e3 are biased positively with respect to electrodes e2 and e4. The negative ions typically tend to concentrate as shown in or about cloud A, whereas the positive ions typically tend to concentrate in or about cloud B. The field in the vicinity of each electrode is shown as F1-F4, respectively. These ions are thus segregated and concentrated by action of fields F1-F4 between cooperating concentrator electrodes e1-e4. The concentration field generated between these electrodes concentrates the ions toward the center of the flow path, which may be implemented before, during or after ion filtering.

In a preferred embodiment, the concentrator electrodes are driven sequentially. This phased drive is shown in FIGS. 10B-10E, where impulses $E_A$, $E_B$, $E_C$, and $E_D$ are sequentially applied to respective electrodes e1-e4, by a phased application of asymmetric waveform 402. This is shown in a two-electrode arrangement (FIG. 10B), four-electrode arrangement (FIG. 10C), and alternatively in a three-electrode arrangement (FIG. 10E), but may also be achieved with other numbers of electrodes.

Figure 10G:
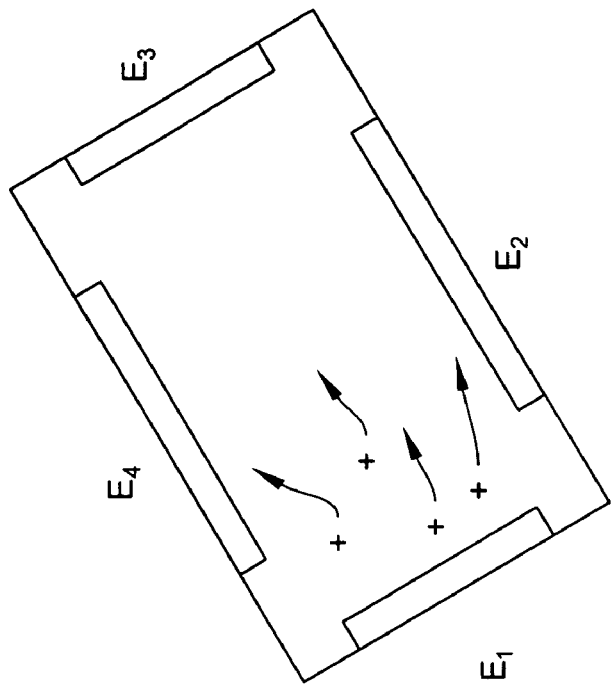
FIGS. 10G-10J show concentrator electrodes and drive signals according to various illustrative embodiments of the invention.
Figure 10F:
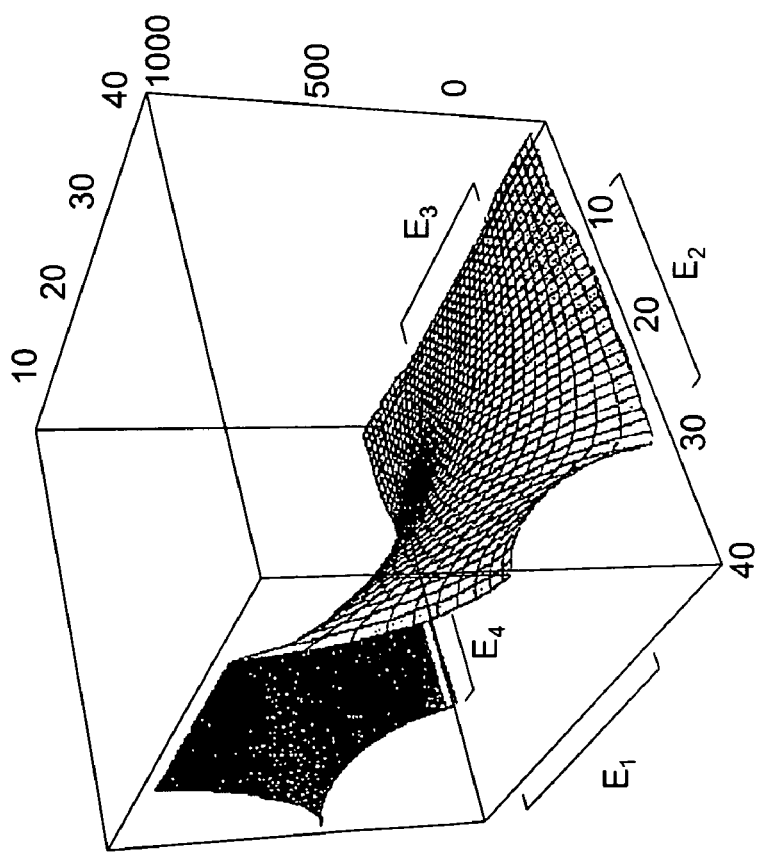
FIG. 10F shows a concentration profile according to an illustrative embodiment of the invention.

The forces in one phase can also be visualized as gradients on a potential energy surface, such as shown in FIG. 10F. In this embodiment, the net effect over all four phases, i.e., one for each electrode, is to concentrate certain ion species into the center of the flow path according to species characteristics. This typically enables ion species separation.

Thus a positive impulse from phased application of drive waveform 402 will drive ion species responsive to that waveform and impulse to be either concentrated or de-concentrated according to their DMS behavioral characteristics. Each waveform will affect various ion species differently. Thus, drive waveform 402 can be selected according to known ion species behaviors to facilitate the analytical process.

As further shown in FIG. 10G, four electrodes are used to generate an inhomogeneous electric field in the space between them (i.e., typically transverse to the ion flow path). In each of the four phases a different voltage is placed on one plate, thus having a different plate in each phase. The net effect on the ions can be a motion towards the center of the channel and away from each electrode. The net forces on some ions in the vicinity of E1 is shown.

Therefore, substantial ion flow control can be imposed in practice of embodiments of the invention. The concentrated ions flow downstream for filtering and detection with improved resolution and better sensitivity. In one illustration, ions are concentrated between arrays of electrodes, and then are filtered downstream. Ion detection is then correlated with the drive signals applied to the array and ion filter, and ion species identification is made, by, for example, referring to a lookup table of stored ion behavior.

Figure 10H:
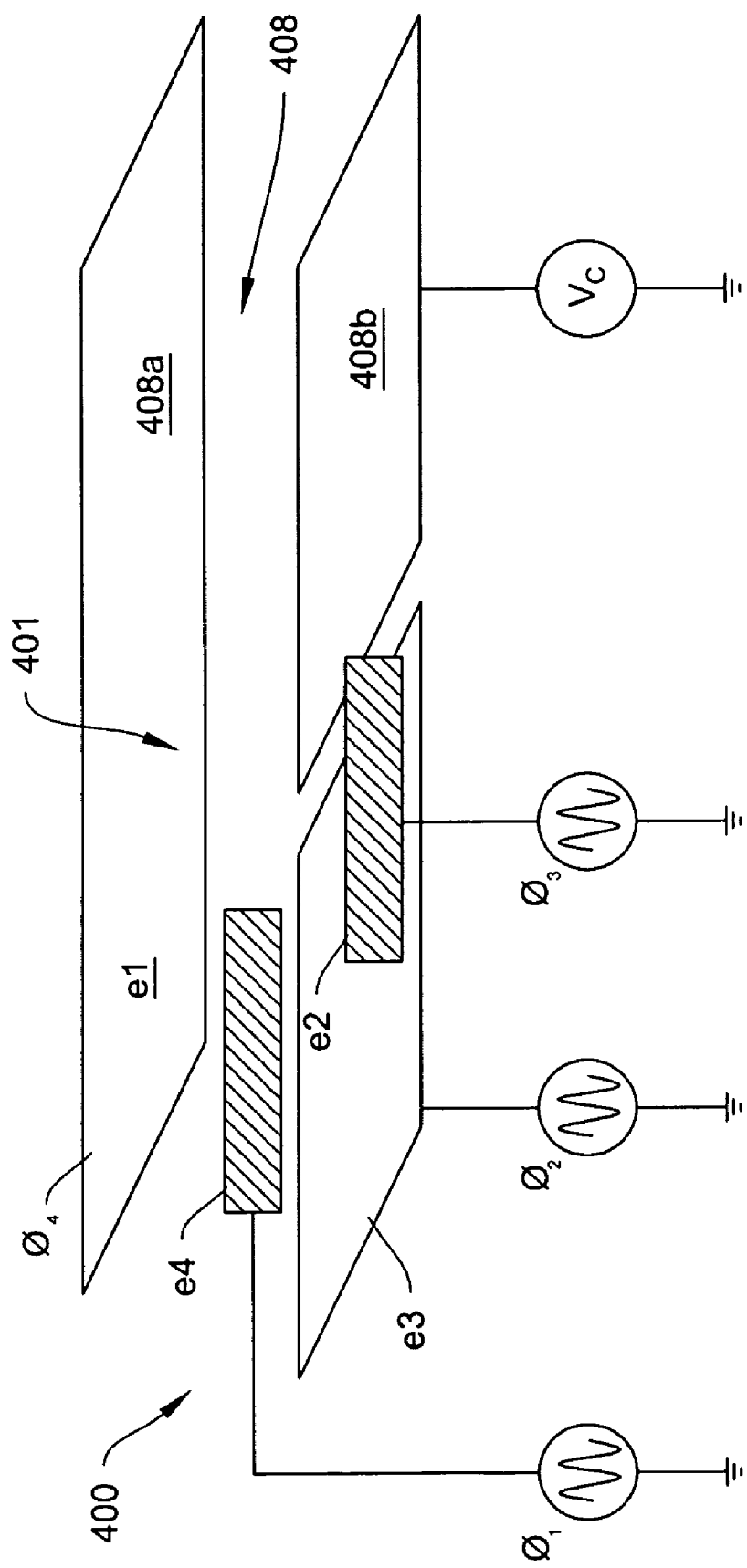

To concentrate ions toward the flow path center, the concentrator electrodes need not be entirely separate from the filter electrodes. As shown in the illustrative embodiment of FIG. 10H, for example, concentrator 401 has concentrator electrodes e1-e4. Adjacent filter 408 has filter electrodes 408a and 408b. One filter electrode 408a is shared as electrode e1 of concentrator 401. Various of these electrodes can be driven as needed, and may be biased DC, grounded, or driven with RF, consistent with the teachings of the invention.

Figures 10I, 10J:
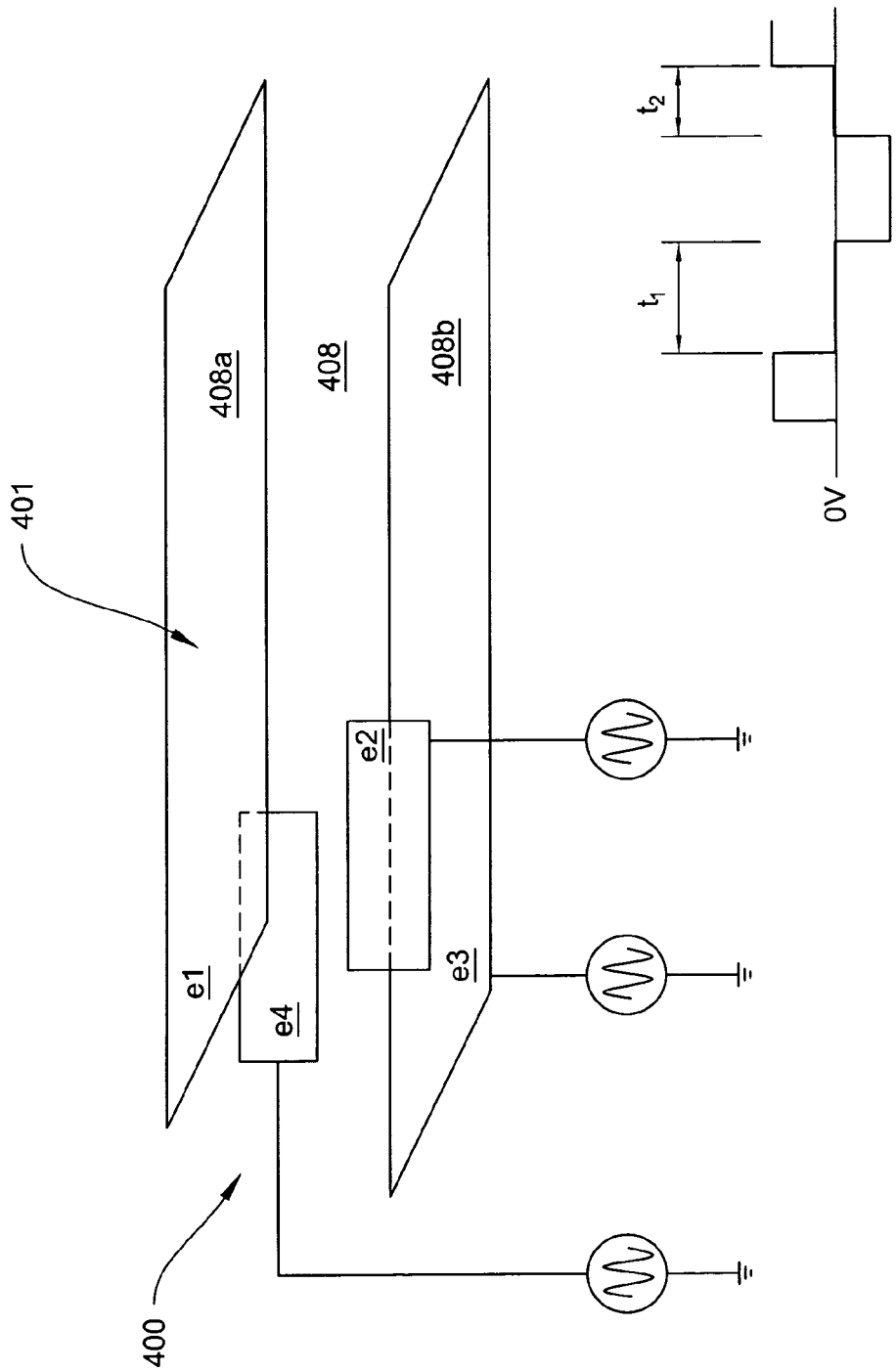

In the illustrative embodiment of FIG. 10I, the two filter electrodes are shared by concentrator 400, i.e., concentrator electrodes e1 and e3 also serve as filter electrodes 408a and 408b. However, in the latter case, the drive waveform has a pause in the filter signal so that the concentrator signal may be applied. This is shown schematically in FIG. 10J, where waveform 404 is provided with a timeout at $t_1$ and/or $t_2$, in the filter signal. For example, signal $E_A$ can be applied during time period $t_1$, and signal $E_B$ can be applied during time period $t_2$, signal $E_C$ can be applied during the next period $t_1$ and signal $E_D$ can be applied during the next time period $t_2$. This illustrative embodiment enables a simplified electrode arrangement to achieve the concentration effect of the invention.

The above embodiments facilitate concentration of selected ions or concentration of ions to the center of the flow path. One objective is to enhance ion species separation and resolution in analyzing the ions.

Facing electrodes of different sizes typically generate a non-uniform field, which can be practiced in an alternative embodiment of the invention for focusing the ion flow. A DMS system including in-homogeneous (or non-homogeneous) fields may be realized in numerous way including the embodiment illustrated in FIGS. 9C and 9D. As shown in FIGS. 9C-9D, a non-uniform field can be generated by driving a different number of the facing electrodes in opposed electrode arrays 275 and 277. For example, electrode $E_5$ of the plurality of electrodes $E_1$-$E_n$ is driven in array 277 and cooperates with a plurality of driven electrodes $E_1$-$E_n$ in array 275. The field F generated between these electrodes is concentrated at the single electrode $E_5$ of array 277, while it is distributed between electrodes $E_1$-$E_n$ (and therefore is at lower field strength) along the face of array 275. This creates a desired condensing or focusing of ions that typically tends to improve system sensitivity. The special non-homogeneous fields illustrated in FIG. 9D may be employed by a DMS to enhance ion separation, resolution, control, and focusing for certain ions.

A result of the non-uniform field is to have the desired focusing effect for collecting or concentrating of ions to assist ion analysis and detection. This on-demand or switchable or controllable ion control feature is useful, since a particular effect (such as ion focusing) has a different impact on different ion species, and therefore may be selectively used to augment species separation. According to further illustrative embodiments of the invention, the foregoing ion control is employed, for example, for texturing, controlling, manipulating, trapping and steering ion flow in the filter field for achieving desired ion behavior.

Reduction of Fringing Fields

The invention may also be applied to reducing the fringing field at the edges of the filter electrodes. In one aspect, the charge dissipation quality of the partially-conducting control material layers of the invention reduces fringing fields. In another aspect, the impact of fringing effects at the edges of the filter electrodes are reduced by appropriately driving electrodes of arrays 211U and 215D to anticipate the fringing effects and to adjust ion behavior.

The DMS filter field generated between the faces of the filter electrodes, such as filter electrodes 20 and 22 of FIG. 1 or electrodes 120 and 130 of FIG. 3E, typically are straight, uniform, and well-defined. A similar result can be achieved between the faces of electrode arrays 211U and 215D of FIG. 4A.

Figure 11A:
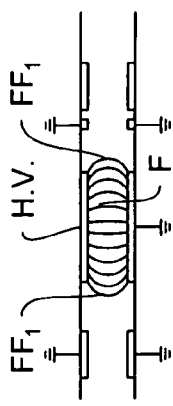
FIGS. 11A-11B show before and after effects on fringing fields according to an illustrative embodiment of the invention.
Figure 11B:
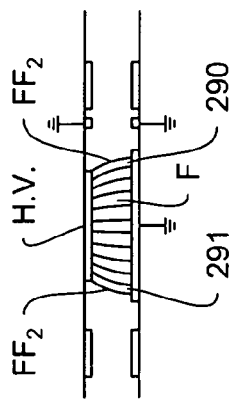

However, the fringing field around the electrode edges can be irregular and can negatively impact ion flow. As shown in FIG. 11A, the fringing field FF1 at the edges of the filter field F has a non-linear shape, which impacts the local ion flow. Nevertheless, formation of the filter arrays 211U and 215D on the partially-conducting control material layers 211 and 215 enables sculpting the fringing field effects. Therefore, as shown in FIG. 11B, in an illustrative embodiment of the invention, the fringing field FF2 that impinges on partially-conducting control material layers 290 and 291, is reduced. The result is to substantially straighten the filter field at its margins. While there still may be a vector associated with the fringing field, it is more uniform and will have more predictable local impact on ion behavior. In a further illustrative embodiment, this remaining vector is neutralized by selectively driving selected electrodes of the array of electrodes.

Figure 12:
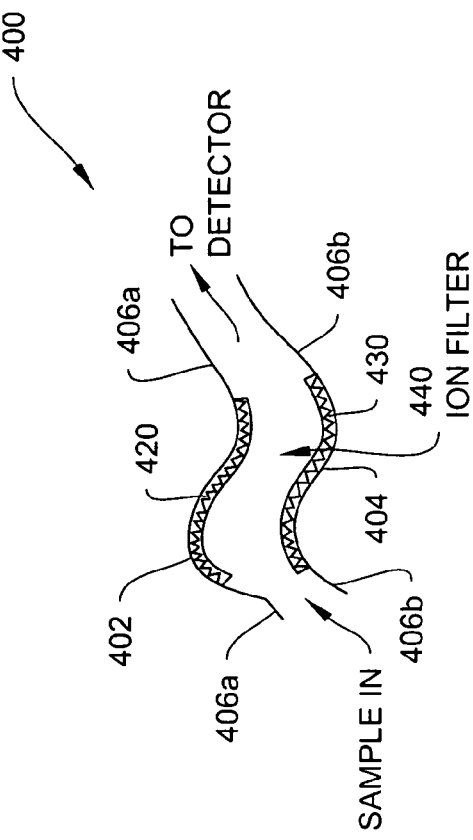
FIG. 12 shows an illustrative embodiment of the invention including a varying flow path.

In the illustrative embodiment of FIG. 12, a non-flat flow path is shown having electrodes 420 and 430 of ion filter 410. The electrodes are formed on substrates 402 and 404. Also provided are charge dissipating surfaces 406a and 406b in an illustrative embodiment of the invention.

While charge dissipation electrodes may reduce the charge that is deposited by ions on the dielectric substrate of an ion based analyzer system, other techniques may be employed to reduce charge build by reducing the amount of ions that are deflected toward the dielectric substrate. Because of the imbalance between the asymmetric field and compensation voltage field at the fringes of DMS filters, ions may be deflected toward adjacent dielectric substrates. Control electrodes, however, may be employed that alter and/or redirect the fringe compensation voltage fields in directions that reduce the amount of ions being adversely deflected toward the dielectric substrates adjacent to a DMS filter.

Figure 13:
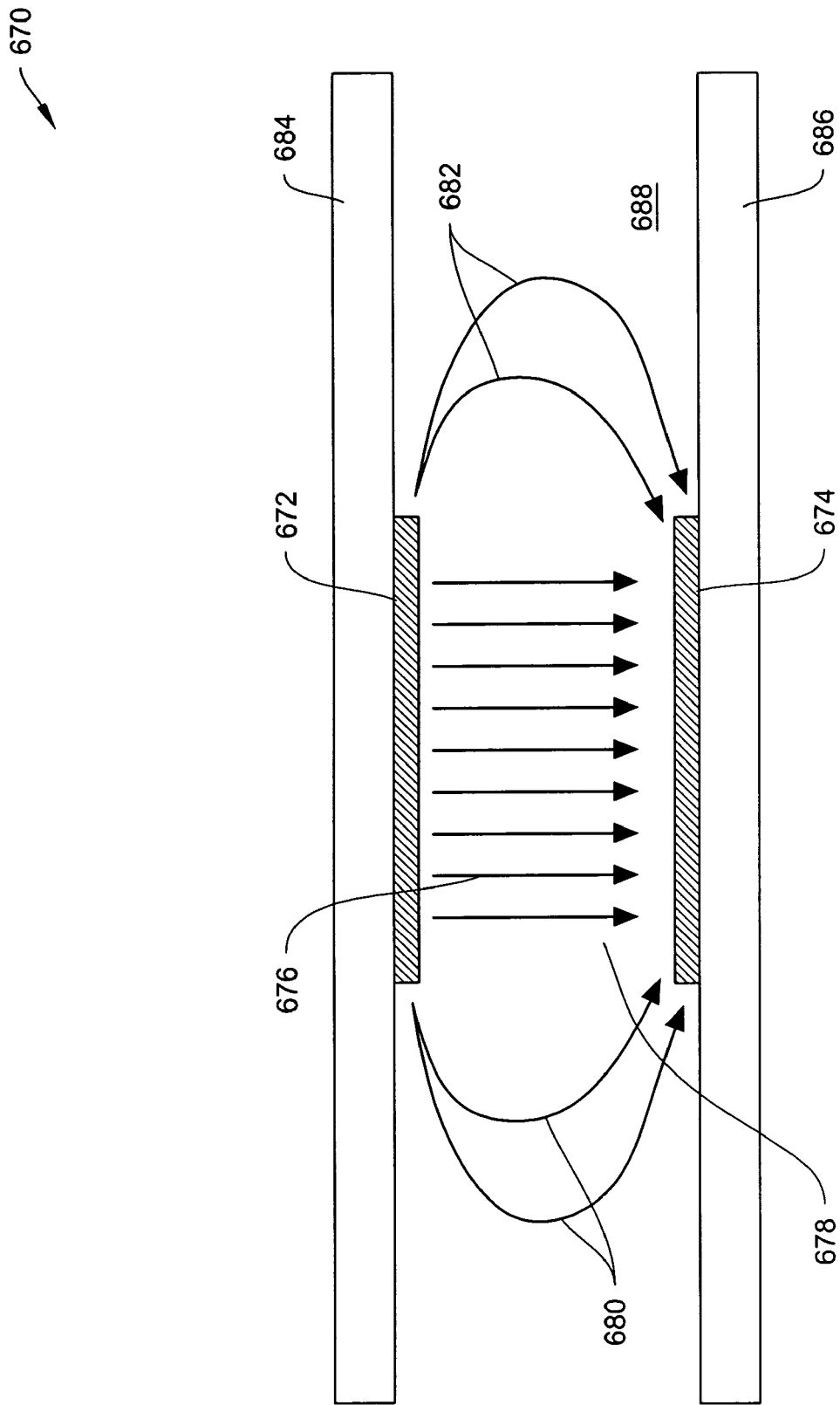
FIG. 13 is a conceptual diagram of the filter region of a DMS system showing the field lines generated between the filter electrodes.

FIG. 13 is a conceptual diagram of the filter region 678 of a DMS system 670 showing the compensation voltage field and/or field lines 676 generated between the filter electrodes 672 and 674. The filter region 678 also includes upstream compensation voltage fringe field lines 680 and downstream compensation voltage fringe field lines 682. Dielectric substrates 684 and 686 define the flow path 688.

FIG. 13 illustrates that the fringe fields and field lines 680 and 682 extend into the flow path 688 beyond the DMS filter electrodes 672 and 674 and beyond the balancing influence of an asymmetric RF field. Thus, the upstream and downstream compensation voltage fringe fields 680 and 682 may direct ions toward one or both of the substrates 684 and 686 which may cause a charge build up on the substrates 684 and/or 686.

Figure 14:
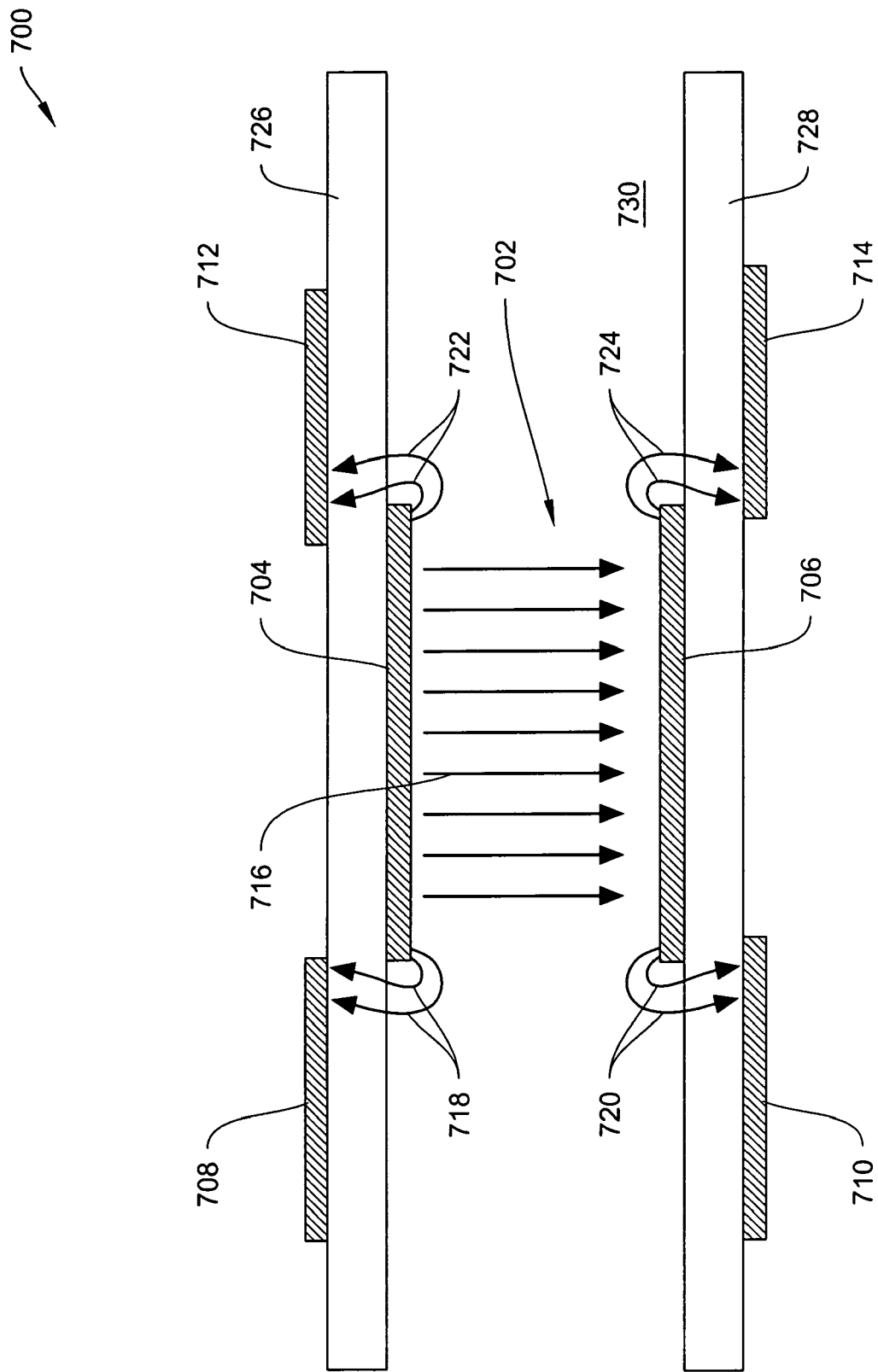
FIG. 14 is a conceptual diagram of the filter region of a DMS system showing the field lines generated between the filter electrodes and the influence of external electrodes adjacent to the DMS filter according to an illustrative embodiment of the invention.

FIG. 14 is a conceptual diagram of the filter region 702 of a DMS system 700 showing the compensation voltage field lines 716 generated between the filter electrodes 704 and 706 and the influence on the fringe field lines 718, 720, 722, and 724 of external control electrodes 708, 710, 712, and 714 adjacent to the DMS filter electrodes 704 and 706 according to an illustrative embodiment of the invention. Dielectric substrates 726 and 728 define the flow path 730.

FIG. 14 illustrates that the fringe fields and/or field lines 718, 720, 722, and 724 are generated by the presence of control electrodes 708, 710, 712, and 714 which may be connected to, biased, and/or controlled by a controller such as the controller 40 of FIG. 1. These fringe fields 718, 720, 722, 724 do not extend beyond the DMS filter electrodes 672 and 674 in the same manner as the fringe field lines 680 and 682 of the DMS system 670. The presence of the control electrodes 708, 710, 712, and 714 effectively bends the fringe field lines 718, 720, 722, and 724 away from a substantial portion of the flow path 730 where ions are entering or exiting the filter region 702. Accordingly, the fringe fields 718, 720, 722, and 724 exert less influence on ions adjacent to the DMS filter electrodes 704 and 706. Therefore, a significantly smaller portion of ions are deflected toward the substrates 726 and/or 728, which reduces charge build up on the substrates 726 and/or 728.

Figure 15:
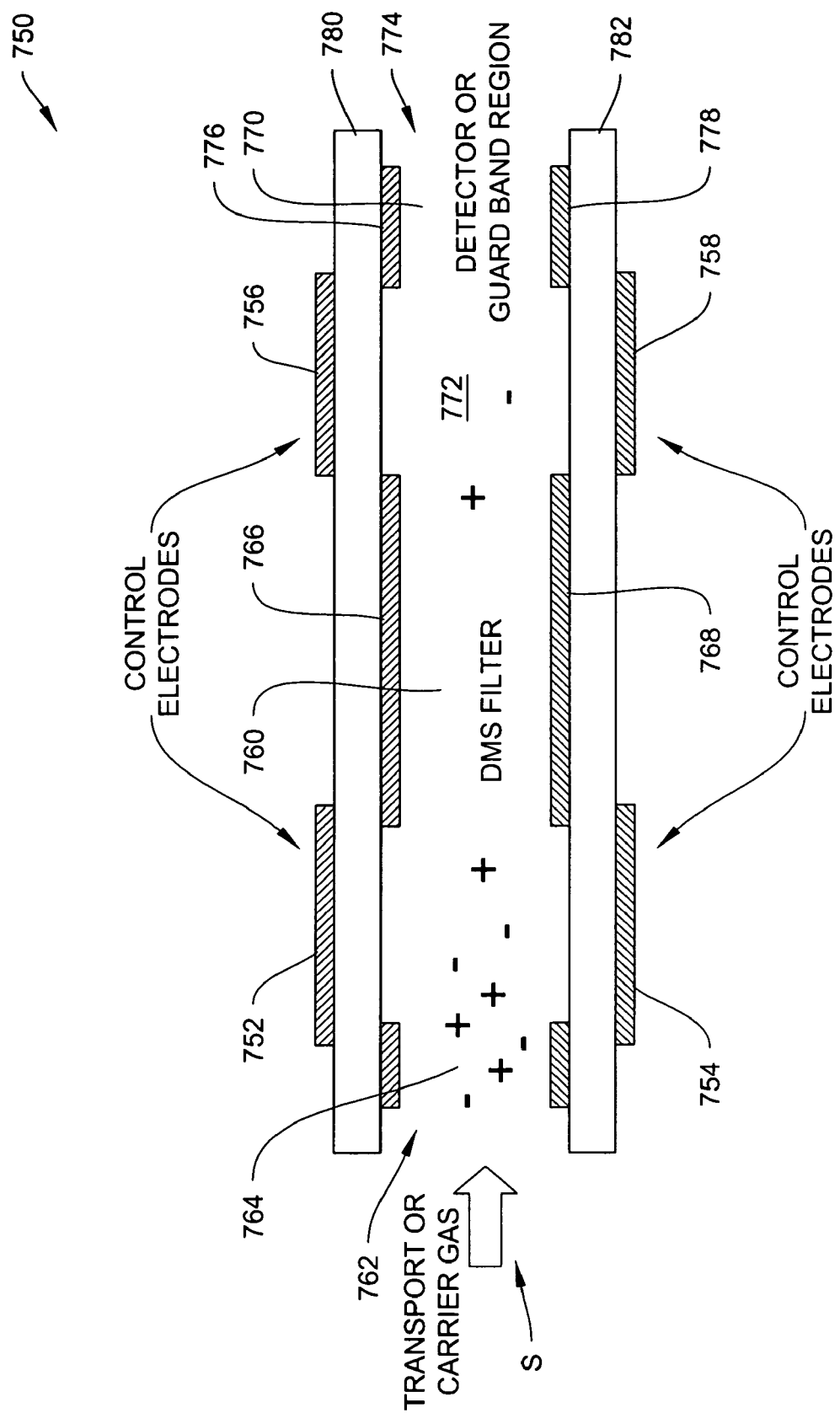
FIG. 15 is a conceptual diagram of a DMS system including external electrodes adjacent to the DMS filter for reducing DMS filter fringing fields according to an illustrative embodiment of the invention.

FIG. 15 is a conceptual diagram of a DMS system 750 including external control electrodes 752, 754, 756, and 758 adjacent to the DMS filter 760 for reducing fringing fields of the DMS filter 760 according to an illustrative embodiment of the invention. The DMS system 750 includes sample S inlet 762, ionization region 764, DMS filter electrodes 766 and 768, detector 770, flow path 772, substrates 780 and 782, and outlet 774. The detector 770 includes detector electrodes 776 and 778.

In one embodiment, the control electrodes 752, 754, 756, and 758 are positioned on the back and/or external surface of the substrates 780 and 782 to localize the compensation voltage fringe field lines proximate to the edge of the DMS filter electrodes 766 and 768. The control electrodes 752, 754, 756, and 758 may be made of and/or include resistive material so that a non-uniform potential may be distributed across the resistive coating. The coating may include ion implanted ceramic. The substrates 780 and 782 may be made of and/or include ceramic. In another embodiment, the control electrodes 752, 754, 756, and 758 are positioned within the substrates 780 an d782, either partially or completely, or some distance from the substrates 780 and 782.

In operation, the DMS system 750 draws a sample S into the ionization region 764 via inlet 762. At least a portion of the sample S is ionized into either or both positive and negative ions. Gas flow within the flow path 772 transports the ions to the DMS filter 760. The controlling electrodes 752 and 754 are biased by, for example, a controller such as controller 40 of FIG. 1, such that the compensation voltage fringe fields at the entrance of the DMS filter 760 are directed toward the controlling electrodes 752 and 754, and substantially away from the ions within the flow path 772. Thus, the influence of the compensation voltage fringe field upstream of the DMS filter 760 is minimized.

The DMS filter 760 then allows selected ions to pass through to the detector 770 for detection. The controlling electrodes 756 and 758 are biased by, for example, a controller such as controller 40 of FIG. 1, such that the compensation voltage fringe fields at the exit of the DMS filter 760 are directed toward the controlling electrodes 756 and 758, and substantially away from the ions within the flow path 772. Thus, the influence of the compensation voltage fringe field downstream of the DMS filter 760 is minimized.

Figures 16A, 16B:
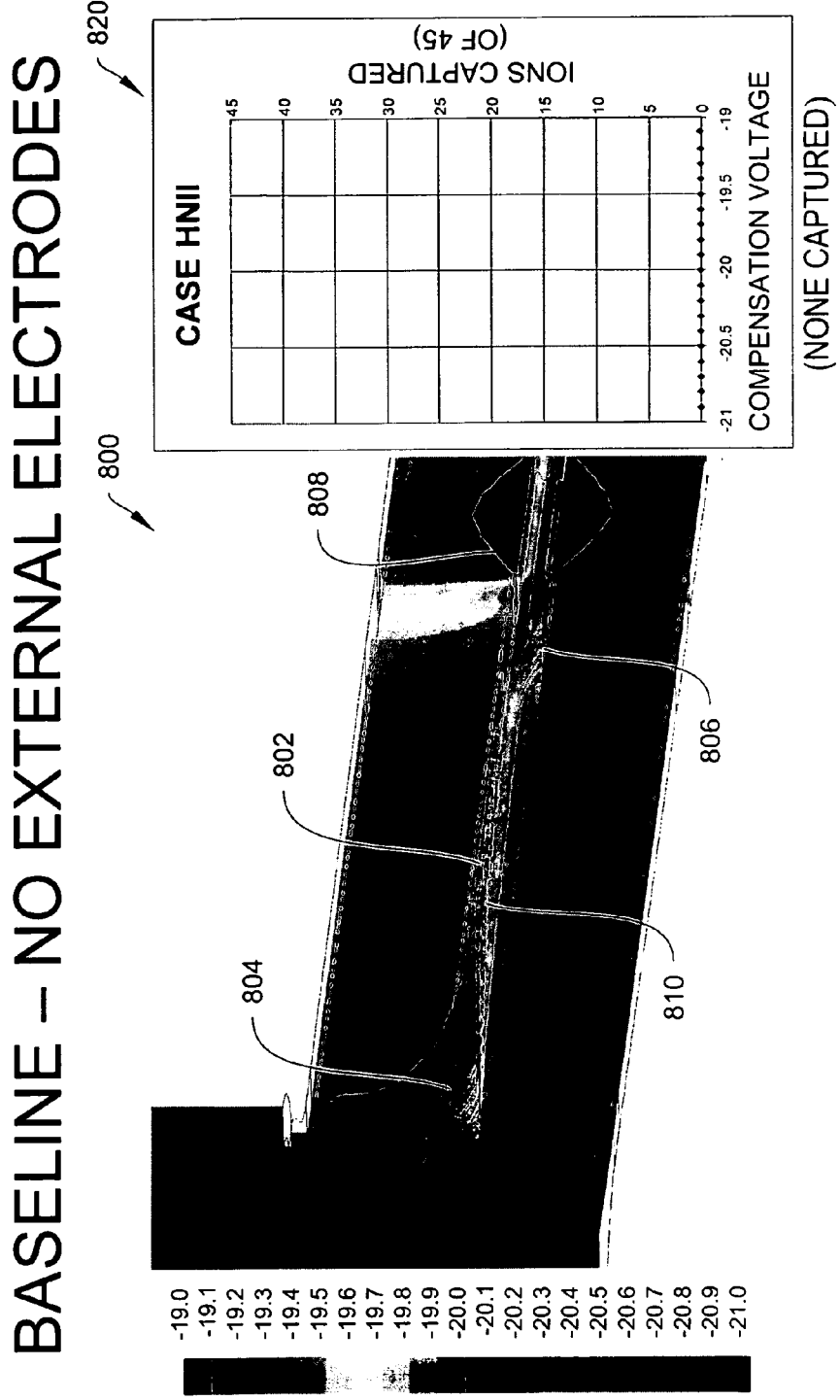
FIG. 16A shows a plot of the modeled trajectory of ions in a DMS system due to unbalanced asymmetric and compensation fields at the DMS filter entrance and exit where no bias voltage is applied to the external electrodes adjacent to the DMS filter.
FIG. 16B is a graph of ion intensity versus compensation voltage based on the plot of modeled trajectory in FIG. 16A.

FIG. 16A shows a plot 800 of the modeled trajectory of ions 810 in a DMS system due to unbalanced asymmetric and compensation fields at the DMS filter 802 entrance and exit where no bias voltage is applied to the external control electrodes adjacent to the DMS filter 802. Because the plot 800 of the model trajectory of ions 810 does not include biasing from at least one control electrode, the ions 810 are deflected toward the upstream and downstream dielectric substrates 804 and 806. Therefore, most ions do not reach and are not detected by the detector 808. The plot 800 of the modeled trajectory illustrates that, without control electrodes to alter the direction of fringe fields of the filter 802, the fringe field created by unbalanced asymmetric and compensation voltage fields directs the ions towards the upstream and/or downstream substrates 804 and 806, preventing the ions 810 from being detected at the detector 808.

FIG. 16B is a graph 820 of ion intensity versus compensation voltage based on the plot 800 of modeled trajectory in FIG. 16A. FIG. 16B illustrates that, without the influence of the control electrodes on the compensation voltage fringe fields, no substantial amount of ions 810 are detected at the detector 808.

Figures 17A, 17B:
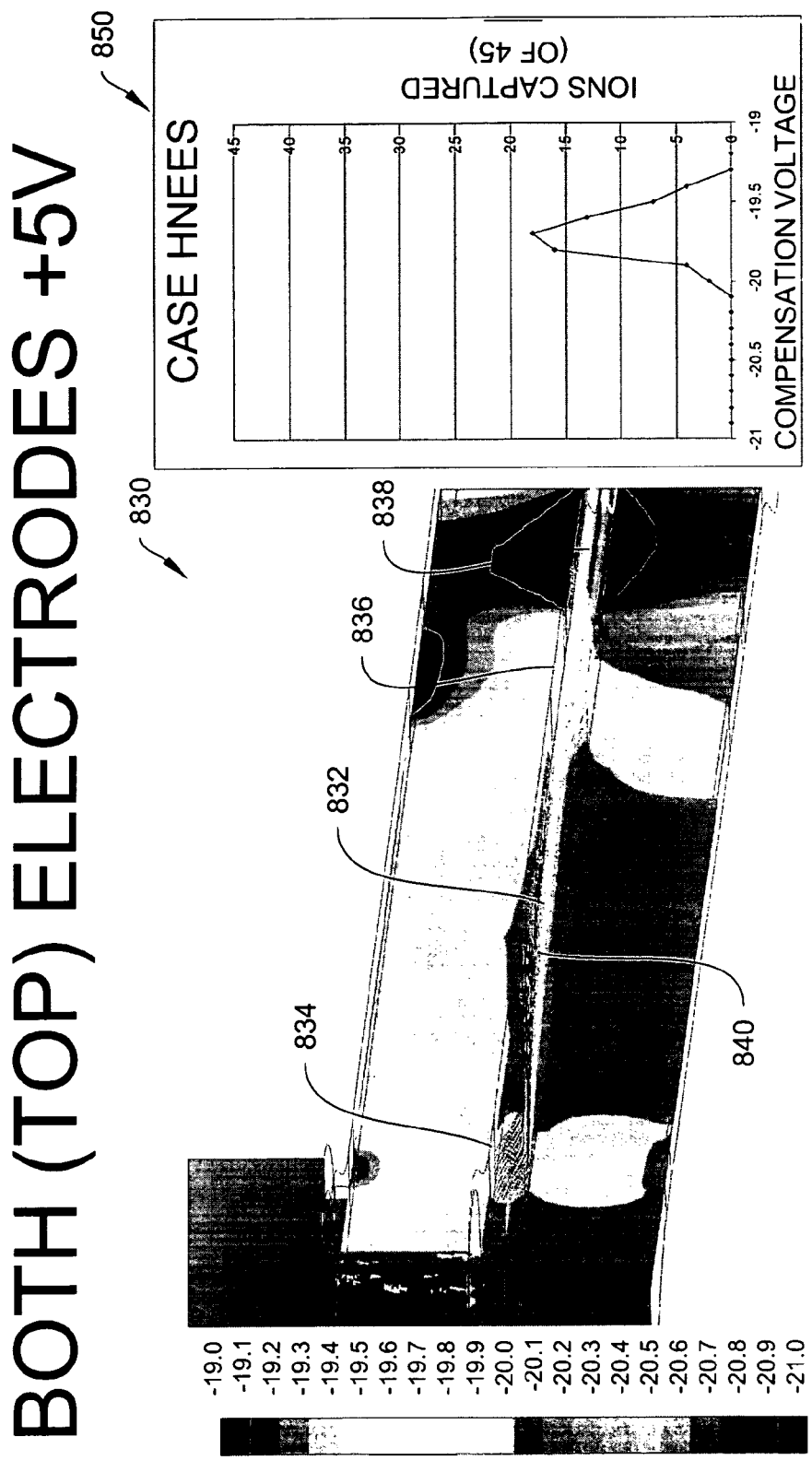
FIG. 17A shows a plot of the modeled trajectory of ions in a DMS system when the external electrodes compensate the unbalanced asymmetric and compensation fields at the DMS filter entrance and exit according to an illustrative embodiment of the invention.
FIG. 17B is a graph of ion intensity versus compensation voltage based on the plot of modeled trajectory in FIG. 17A.

FIG. 17A shows a plot 830 of the modeled trajectory of ions 840 in a DMS system when the control electrodes compensate for the unbalanced asymmetric and compensation fields at the DMS filter 832 entrance and exit according to an illustrative embodiment of the invention. Because the plot 830 of the model trajectory of ions 840 does include biasing from at least one control electrode, the ions 840 are not deflected toward the upstream and downstream dielectric substrates 834 and 836. Therefore, most ions do reach and are detected by the detector 838. The plot 830 of the modeled trajectory illustrates that, with the influence of control electrodes that alter the direction of fringe fields of the filter 832, the fringe field is minimized, allowing the ions 840 to be detected at the detector 838.

FIG. 17B is a graph 850 of ion intensity versus compensation voltage based on the plot 830 of modeled trajectory in FIG. 17A. FIG. 17B illustrates that the influence of control electrodes such as control electrodes 752, 754, 756, and 758 minimizes the effect of fringe fields on the ions 840 upstream and downstream of the filter 832. Thus, the control electrodes advantageous improve the sensitivity of a DMS system.

Any combination of control electrodes, gas inlets, substrate recesses, dissipation electrodes may be employed to facilitate ion control and to compensate for, counteract, and/or direct DMS filter fringe fields or other fields within an ion mobility based analyzer.

It should be noted that that the terms spectrometer, apparatus, assembly and system may include and refer to a filter, detector, sensor, separator, and the like, interchangeably for purposes within the spirit and scope of the invention. The terms drift tube, flow path, and flow channel may be used interchangeably and remain within the spirit and scope of the invention. The terms upper, lower, inner, and outer are relative, and are used by way of illustration and not by way of limitation. Additionally, the invention is operable with gas and liquid samples, even though for convenience the illustrative examples above refer to samples in a gas flow. Further, the invention may be employed with planar, cylindrical, radial and other device configurations.

While this invention has been particularly shown and described with references to illustrative embodiments thereof, various changes in form and details may be made, without departing from the scope of the invention encompassed by the appended claims.

What is claimed is:

1. A system for analyzing ions of a sample comprising:
a flow path for flowing ions of a sample,
an ion filter for generating an asymmetric field and a compensation field in said flow path to pass through selected ions in the flow path, and
a controller for counteracting a charge buildup within the flow path.

2. The system of claim 1, wherein the counteracting includes applying a set of compensation voltages to the ion filter to generate a set of compensation fields.

3. The system of claim 2, wherein a first portion of the compensation voltages are positive and a second portion of the compensation voltages are negative.

4. The system of claim 3, wherein the first portion and second portion of the compensation voltages are substantially equal.

5. The system of claim 3, wherein the first portion and second portion of the compensation voltages are not substantially equal.

6. The system of claim 1 comprising a detector for collecting a portion of the ions in the flow path.

7. The system of claim 6, wherein the counteracting includes:
measuring a first compensation voltage associated with a first ion intensity peak of ions collected at the detector for a selected ion species when a first asymmetric RF voltage is applied to the ion filter,
measuring a second compensation voltage associated with a second ion intensity peak of the ions collected at the detector for a selected ion species when the an asymmetric RF voltage is substantially not applied to the ion filter, and determining a zero-peak offset by subtracting the second compensation voltage from the first compensation voltage.

8. The system of claim 7, wherein the counteracting includes reporting the zero-peak offset.

9. The system of claim 7, wherein the counteracting includes correcting the position of an ion intensity peak with respect to a compensation voltage value based on the zero-peak offset.

10. The system of claim 1 comprising at least one control electrode, the at least one control electrode being positioned outside the flow path.

11. The system of claim 10, wherein the counteracting includes applying a bias voltage to the at least one control electrode to direct a portion of the compensation field substantially away from the flow path.

12. The system of claim 1 comprising at least one recess along the flow path, the at least one recess being substantially adjacent to the ion filter.

13. The system of claim 12 comprising at least one dissipation electrode within the at least one recess, wherein the counteracting includes applying a bias voltage to the at least one dissipation electrode for removing charge build up within the recess.

14. The system of claim 1 comprising at least one gas inlet located substantially adjacent to the ion filter, wherein the counteracting includes introducing a gas flow into the flow path to direct the ion flow within the flow path.

15. The system of claim 14, wherein the gas inlet includes a separator.

16. The system of claim 15, wherein the separator includes a porous material.

17. The system of claim 15, wherein the separator includes a permeable material.

18. A method for analyzing ions of a sample comprising:
flowing ions of a sample within a flow path,
filtering ions within the flow path by applying an asymmetric field and compensation field, and
counteracting a charge buildup within the flow path.

19. The method of claim 18, wherein the counteracting includes applying a set of compensation voltages to an ion filter to generate a set of compensation fields.

20. The method of claim 19, wherein a first portion of the compensation voltages are positive and a second portion of the compensation voltages are negative.

21. The method of claim 20, wherein the first portion and second portion of the compensation voltages are substantially equal.

22. The method of claim 20, wherein the first portion and second portion of the compensation voltages are not substantially equal.

23. The method of claim 18 comprising collecting a portion of the ions in the flow path.

24. The method of claim 23, wherein the counteracting includes:
measuring a first compensation voltage associated with a first ion intensity peak of ions collected for a selected ion species when a first asymmetric RF voltage is applied to the flow path,
measuring a second compensation voltage associated with a second ion intensity peak of the ions collected for a selected ion species when the an asymmetric RF voltage is substantially not applied to the flow path, and
determining a zero-peak offset by subtracting the second compensation voltage from the first compensation voltage.

25. The method of claim 24, wherein the counteracting includes reporting the zero-peak offset.

26. The method of claim 24, wherein the counteracting includes correcting the position of an ion intensity peak with respect to a compensation voltage value based on the zero-peak offset.

27. The method of claim 18, wherein the counteracting includes direct a portion of the compensation field substantially away from the flow path.

28. The method of claim 18 comprising providing at least one recess along the flow path.

29. The method of claim 28, wherein the counteracting includes removing charge build up within the recess.

30. The method of claim 1, wherein the counteracting includes introducing a gas flow into the flow path to direct the ion flow within the flow path.

* * * * *